(12) United States Patent
Fujimura et al.

(10) Patent No.: US 8,137,821 B2
(45) Date of Patent: *Mar. 20, 2012

(54) SUBSTITUTED ETHYNYL GOLD-NITROGEN CONTAINING HETEROCYCLIC CARBENE COMPLEX AND ORGANIC ELECTROLUMINESCENT DEVICE USING THE SAME

(75) Inventors: Osamu Fujimura, Ube (JP); Kenji Fukunaga, Ichihara (JP); Takashi Honma, Ube (JP); Toshikazu Machida, Ichihara (JP); Takeshi Takahashi, Ube (JP)

(73) Assignee: UBE Industries, Ltd., Ube-Shi, Yamaguchi (JP)

( * ) Notice: Subject to any disclaimer, the term of this patent is extended or adjusted under 35 U.S.C. 154(b) by 881 days.

This patent is subject to a terminal disclaimer.

(21) Appl. No.: 11/883,320

(22) PCT Filed: Jan. 31, 2006

(86) PCT No.: PCT/JP2006/301504
§ 371 (c)(1),
(2), (4) Date: Jul. 30, 2007

(87) PCT Pub. No.: WO2006/080515
PCT Pub. Date: Aug. 3, 2006

(65) Prior Publication Data
US 2009/0091243 A1    Apr. 9, 2009

(30) Foreign Application Priority Data

Jan. 31, 2005 (JP) ................................ 2005-022390
Apr. 14, 2005 (JP) ................................ 2005-116449
Sep. 16, 2005 (JP) ................................ 2005-270082

(51) Int. Cl.
H01L 51/54      (2006.01)
C09K 11/06      (2006.01)
C07F 1/12       (2006.01)

(52) U.S. Cl. ........ 428/690; 428/917; 548/103; 556/112; 313/504; 313/506; 252/301.16; 257/40; 257/E51.044

(58) Field of Classification Search .................... None
See application file for complete search history.

(56) References Cited

U.S. PATENT DOCUMENTS

| | | | |
|---|---|---|---|
| 5,728,839 A | 3/1998 | Herrmann et al. | |
| 7,932,398 B2 * | 4/2011 | Fujimura et al. | 548/103 |
| 2002/0050786 A1 * | 5/2002 | Yamazaki et al. | 313/504 |
| 2002/0068192 A1 * | 6/2002 | Moriyama et al. | 428/690 |
| 2003/0119660 A1 | 6/2003 | Herrmann et al. | |
| 2003/0149273 A1 | 8/2003 | Militzer et al. | |

FOREIGN PATENT DOCUMENTS

| | | |
|---|---|---|
| JP | 8-231571 A | 9/1996 |
| JP | 2003-113191 A | 4/2003 |
| JP | 2003-183187 A | 7/2003 |
| JP | 2004-175799 A | 6/2004 |
| WO | WO-98/27064 A1 | 6/1998 |
| WO | WO-03/079737 A2 | 9/2003 |

OTHER PUBLICATIONS

Singh et al. "A facile one-step synthesis of a lipophilic gold(I) carbine complex-x-ray crystal structure of LAuCCH (L=1,3-di-tert-butyl imidazol-2-ylidene." Eur. J. Inorg. Chem. 2005, vol. 15, pp. 3057-2062.*
Bourissou et al. "Stable Carbenes" Chem. Rev. 2000, vol. 100 pp. 39-91.*
Cross et al., "Preparation and Ligand-exchange Reactions of Phosphinegold Ethynyl Complexes," J. Chem. Soc., Dalton Trans., 1986, pp. 411.
Jikken Kagaku Koza, 4th ed., Maruzen, vol. 18, 1991, pp. 455-468.
Echavarren et al., "Palladium-Catalyzed Coupling of Aryl Inflates with Organostannanes," J. Am. Chem. Soc., vol. 109, 1987, pp. 5478-5486.
Arduengo et al., "Electronic Stabilization of Nucleophilic Carbenes," J. Am. Chem. Soc., vol. 114, 1992, pp. 5530-5534.
Office Action issued on May 11, 2010 in Japanese Application No. 2007-500643.
Wang, Harrison M. J., et al. "Synthesis, Structure, and Spectroscopic Properties of Gold(I)-Carbene Complexes," Organometallics, vol. 18, pp. 1216-1223, Feb. 27, 1999.

* cited by examiner

*Primary Examiner* — Jennifer A Chriss
*Assistant Examiner* — Michael H Wilson
(74) *Attorney, Agent, or Firm* — Birch, Stewart, Kolasch & Birch, LLP

(57) ABSTRACT

A substituted ethynyl gold-nitrogen containing heterocyclic carbene complex of formula (1):

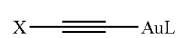

(1)

wherein L represents a nitrogen containing heterocyclic carbene ligand; X represents an alkyl, a cycloalkyl, an aryl, an aralkyl or a heterocyclic group; in which one or more hydrogen atoms on the carbon atom(s) of X may be replaced by a halogen atom, an alkyl, a cycloalkyl, an alkenyl, an aryl, an aralkyl, an alkoxy, an aryloxy, a dialkylamino, an acyl or an arylcarbonyl group; and, when more than one hydrogen atom on the carbon atom(s) of X is replaced by the alkyl, the alkenyl, the aryl, the aralkyl, the alkoxy, the aryloxy, the dialkylamino, the acyl or the arylcarbonyl group, the adjacent groups may be bonded together to form a ring, a method for preparing the same, and an organic electroluminescent device containing the same in at least one organic compound thin layer.

10 Claims, 1 Drawing Sheet

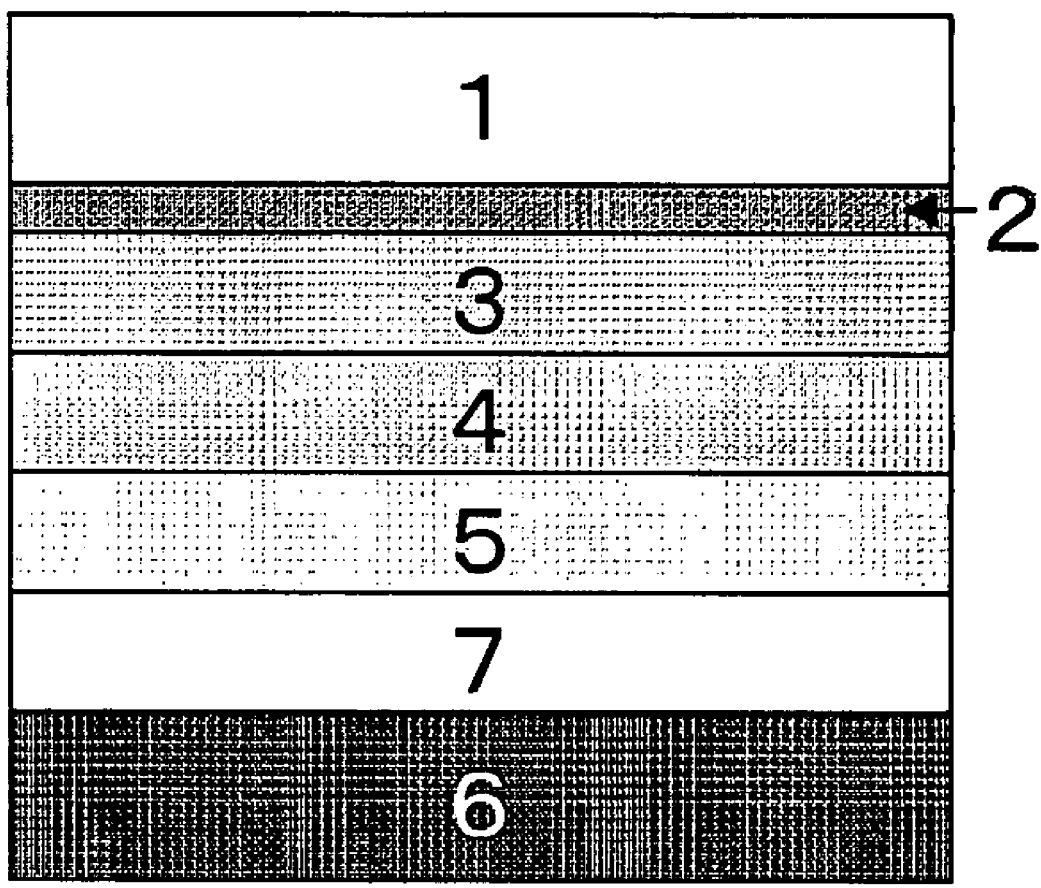

SUBSTITUTED ETHYNYL GOLD-NITROGEN CONTAINING HETEROCYCLIC CARBENE COMPLEX AND ORGANIC ELECTROLUMINESCENT DEVICE USING THE SAME

FIELD OF THE INVENTION

The present invention relates to a substituted ethynyl gold-nitrogen containing heterocyclic carbene complex useful as, e.g., a luminescent material for electroluminescent devices (organic electroluminescent devices) and an organic electroluminescent device using the same.

BACKGROUND ART

Conventionally, the substituted ethynyl gold-nitrogen containing heterocyclic carbene complex of the present invention and an organic luminescent device using said complex as a luminescent material have not been known.
Non-patent document 1: Journal of Chemical Society, Dalton Trans., 1986, 411
Non-patent document 2: Lecture on Experimental Chemistry, Fourth edition, published by Maruzen Co., Ltd., page 455, Vol. 18 (1991)
Non-patent document 3: J. Am. Chem. Soc., 109, 5478 (1987)
Non-patent document 4: J. Am. Chem. Soc., 114, 5530 (1992)
Patent document 1: WO98/27064

DISCLOSURE OF THE INVENTION

Problems to be Solved by the Invention

Accordingly, the object of the present invention is to provide an organic electroluminescent device that emits blue to green light when a voltage is applied and a substituted ethynyl gold-nitrogen containing heterocyclic carbene complex useful as, e.g., a luminescent material for the organic luminescent device.

Means to Solve the Problems

The present invention is directed to a substituted ethynyl gold-nitrogen containing heterocyclic carbene complex represented by the general formula (1):

(1)

wherein:
L represents a nitrogen containing heterocyclic carbene ligand; and
X represents an alkyl group, a cycloalkyl group, an aryl group, an aralkyl group or a heterocyclic group; in which one or more hydrogen atoms on the carbon atom(s) of X may be replaced by a halogen atom, an alkyl group, a cycloalkyl group, an alkenyl group, an aryl group, an aralkyl group, an alkoxy group, an aryloxy group, a dialkylamino group, an acyl group or an arylcarbonyl group; and, when more than one hydrogen atom on the carbon atom(s) of X is replaced by the alkyl group, the alkenyl group, the aryl group, the aralkyl group, the alkoxy group, the aryloxy group, the dialkylamino group, the acyl group or the arylcarbonyl group, the adjacent groups may be bonded together to form a ring.

Effect of the Invention

In the present invention, there can be provided an organic electroluminescent device that emits blue to green light when a voltage is applied and a substituted ethynyl gold-nitrogen containing heterocyclic carbene complex useful as, e.g., a luminescent material for the organic luminescent device.

BRIEF DESCRIPTION OF THE DRAWING

FIG. 1 is a diagrammatic view of the electroluminescent device in Example 49, and, in the FIGURE, reference numeral 1 designates glass substrate, 2 designates ITO film (positive electrode), 3 designates hole transport layer, 4 designates light emitting layer, 5 designates hole block layer, 6 designates Al electrode, and 7 designates electron transport layer.

BEST MODE FOR CARRYING OUT THE INVENTION

The substituted ethynyl gold-nitrogen containing heterocyclic carbene complex of the present invention is represented by the general formula (1) above. In the general formula (1), L represents a nitrogen containing heterocyclic carbene ligand. X represents an alkyl group, a cycloalkyl group, an aryl group, an aralkyl group or a heterocyclic group.

Preferred examples of the alkyl groups include alkyl groups having 1 to 10 carbon atoms, such as a methyl group, an ethyl group, a propyl group, a butyl group, a pentyl group, a hexyl group, a heptyl group, an octyl group, a nonyl group and a decyl group. These substituents include their isomers.

Preferred examples of the cycloalkyl groups include cycloalkyl groups having 3 to 12 carbon atoms, such as a cyclopropyl group, a cyclobutyl group, a cyclopentyl group, a cyclohexyl group, a cycloheptyl group, a cyclooctyl group, a cyclononyl group, a cyclodecyl group, a cycloundecyl group and a cyclododecyl group.

Preferred examples of the aryl groups include aryl groups having 6 to 18 carbon atoms, such as a phenyl group, a tolyl group, a xylyl group, a naphthyl group, a dimethylnaphthyl group, an anthryl group, a phenanthryl group, a chrysenyl group, a tetraphenyl group and a naphthacenyl group. These substituents include their isomers.

Preferred examples of the aralkyl groups include aralkyl groups having 7 to 20 carbon atoms, such as a benzyl group, a naphthylmethyl group, an indenylmethyl group and a biphenylmethyl group.

Examples of the heterocyclic groups include a pyrrolyl group, a furanyl group, a thiophenyl group, an indolyl group, a benzofuranyl group, a benzothiophenyl group, a pyridyl group, a pyrazyl group, a pyrimidyl group, a pyridazyl group, a quinolyl group, an isoquinolyl group, a quinazolyl group, a quinoxalyl group and the like.

One or more hydrogen atoms on the carbon atom(s) of X may be replaced by a halogen atom, an alkyl group, a cycloalkyl group, an alkenyl group, an aryl group, an aralkyl group, an alkoxy group, an aryloxy group or a dialkylamino group.

Examples of the halogen atoms include a fluorine atom, a chlorine atom, a bromine atom and an iodine atom.

Preferred examples of the alkyl groups include alkyl groups having 1 to 20 carbon atoms, especially preferably having 1 to 12 carbon atoms, such as a methyl group, an ethyl group, a propyl group, a butyl group, a pentyl group, a hexyl group, a heptyl group, an octyl group, a nonyl group, a decyl group, an undecyl group and a dodecyl group. An isopropyl group or a tert-butyl group is preferably used. These substituents include their isomers.

Especially preferred examples of the cycloalkyl groups include cycloalkyl groups having 3 to 7 carbon atoms, such as a cyclopropyl group, a cyclobutyl group, a cyclopentyl group, a cyclohexyl group, a cyclopentyl group, a cyclohexyl group and a cycloheptyl group.

Preferred examples of the alkenyl groups include alkenyl groups having 2 to 20 carbon atoms, especially preferably having 2 to 12 carbon atoms, such as a vinyl group, a propenyl group, a butenyl group, a pentenyl group, a hexenyl group, a heptenyl group, an octenyl group, a nonenyl group, a decenyl group, an undecenyl group and a dodecenyl group. These substituents include their isomers.

Preferred examples of the aryl groups include aryl groups having 6 to 20 carbon atoms, especially preferably having 6 to 16 carbon atoms, such as a phenyl group, a tolyl group, a xylyl group, a naphthyl group, a dimethylnaphthyl group, an anthryl group, a phenanthryl group, a fluorenyl group and a pyrenyl group. These substituents include their isomers.

Preferred examples of the aralkyl groups include aralkyl groups having 7 to 20 carbon atoms, such as a benzyl group, a naphthylmethyl group, an indenylmethyl group and a biphenylmethyl group.

Especially preferred examples of the alkoxy groups include alkoxy groups having 1 to 10 carbon atoms, such as a methoxy group, an ethoxy group, a propoxy group, a butoxy group, a pentanoxy group, a hexanoxy group, a heptanoxy group, an octanoxy group, a nonanoxy group and a decanoxy group. These substituents include their isomers.

Especially preferred examples of the aryloxy groups include aryloxy groups having 6 to 14 carbon atoms, such as a phenoxy group, a tolyloxy group, a xylyloxy group, a naphthoxy group and a dimethylnaphthoxy group. These substituents include their isomers.

Especially preferred examples of the dialkylamino groups include dialkylamino groups having 2 to 10 carbon atoms, such as a dimethylamino group, a diethylamino group and a dipropylamino group. These substituents include their isomers.

Especially preferred examples of the acyl groups include acyl groups having 2 to 10 carbon atoms, such as an acetyl group, a propanoyl group and a butanoyl group. These substituents include their isomers.

Especially preferred examples of the arylcarbonyl groups include arylcarbonyl groups having 7 to 11 carbon atoms, such as a benzoyl group, a fluorobenzoyl group and a naphthylcarbonyl group. These substituents include their isomers.

When more than one hydrogen atom on the carbon atom(s) of X is replaced by the alkyl group, the alkenyl group, the aryl group, the aralkyl group, the alkoxy group, the aryloxy group, the dialkylamino group, the acyl group or the arylcarbonyl group, the adjacent groups may be bonded together to form a ring.

When the adjacent groups are bonded together to form a ring, examples of the rings formed include a cyclopentene ring, a cyclohexene ring, a cycloheptene ring, a benzene ring, a naphthalene ring, a tetrahydrofuran ring, a benzopyran ring, an N-methylpyrrolidine ring, an N-methylpiperidine ring and the like.

The nitrogen containing heterocyclic carbene ligand is represented by the general formula (2) or (3):

(2)

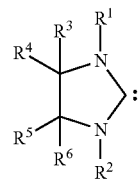

(3)

wherein $R^1$ and $R^2$, which may be identical or different from each other, represent an alkyl group, a cycloalkyl group, a polycycloalkyl group or an aryl group, and $R^3$, $R^4$, $R^5$ and $R^6$, which may be identical or different from each other, represent a hydrogen atom, a halogen atom, an alkyl group, an alkenyl group, an aryl group, an aralkyl group, an alkoxy group, an aryloxy group, a nitro group, a cyano group or a dialkylamino group; the adjacent groups may be bonded together to form a ring; and any hydrogen atom(s) in $R^1$ to $R^6$ may be replaced by a halogen atom, an alkyl group, a cycloalkyl group, an alkenyl group, an aryl group, an aralkyl group, an alkoxy group or an aryloxy group.

$R^1$ and $R^2$ represent an alkyl group, a cycloalkyl group, a polycycloalkyl group or an aryl group, wherein the alkyl group, the cycloalkyl group and the aryl group are as defined above for X.

Preferred examples of the polycycloalkyl groups include polycycloalkyl groups having 6 to 10 carbon atoms, such as a bicyclo-[2.1.1]-hexyl group, a bicyclo-[2.2.1]-heptyl group, a bicyclo-[2.2.2]-octyl group, a bicyclo-[3.3.0]-octyl group, a bicyclo-[4.3.0]-nonyl group, a bicyclo-[4.4.0]-decyl group and an adamantyl group.

$R^3$, $R^4$, $R^5$ and $R^6$ represent a hydrogen atom, a halogen atom, an alkyl group, an alkenyl group, an aryl group, an aralkyl group, an alkoxy group, an aryloxy group, a nitro group, a cyano group or a dialkylamino group, wherein the alkyl group, the alkenyl group, the aryl group, the aralkyl group, the alkoxy group, the aryloxy group and the dialkylamino group are as defined above for X.

Any hydrogen atom(s) in $R^1$, $R^2$, $R^3$, $R^4$, $R^5$ and $R^6$ may be replaced by a halogen atom, an alkyl group, a cycloalkyl group, an alkenyl group, an aryl group, an aralkyl group, an alkoxy group, or an aryloxy group, and these groups are as defined above for X. Particularly, with respect to $R^1$ and $R^2$, a tert-butyl group, a 2,6-diisopropylphenyl group, a 2,4,6-trimethylphenyl group or an adamantyl group is preferred, and, with respect to $R^3$, $R^4$, $R^5$ and $R^6$, a hydrogen atom or a halogen atom is preferred, and a chlorine atom is especially preferred.

For instance, ligands represented by the formulae (4) to (13):

(4)

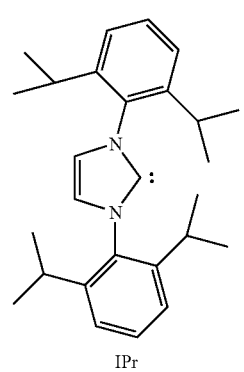

IPr (5)
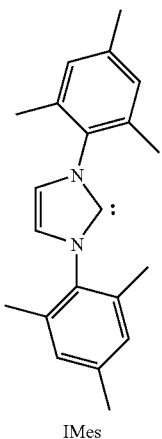
IMes
(6)
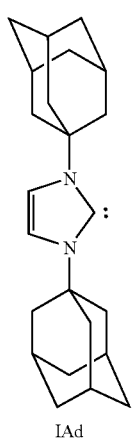
IAd
(7)
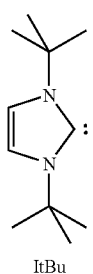
ItBu
(8)
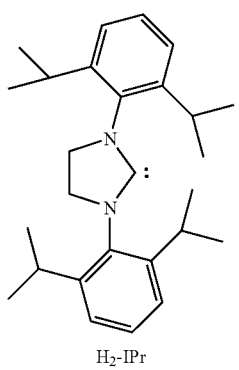
H₂-IPr
(9)
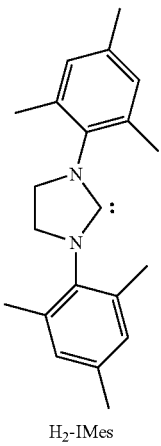
H₂-IMes
(10)
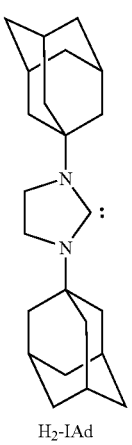
H₂-IAd
(11)
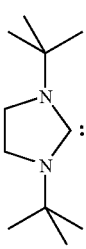
H₂-ItBu
(12)
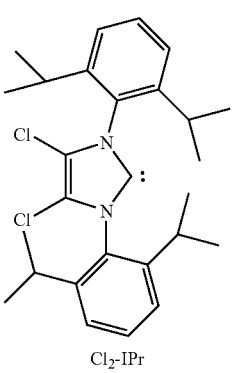
Cl₂-IPr

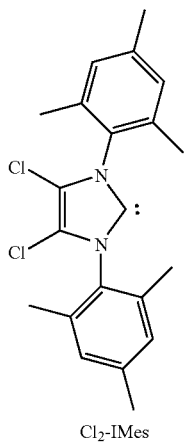

Cl₂-IMes are specific examples of the nitrogen containing heterocyclic carbene ligands (L) in the present invention.

The substituted ethynyl gold-nitrogen containing heterocyclic carbene complex represented by the general formula (1) of the present invention is obtained as shown in, for example, the reaction scheme (1):

Reaction scheme (1)

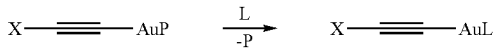

wherein X and L are as defined above, and P represents a monodentate phosphine ligand
by reacting a substituted ethynyl gold phosphine complex with a nitrogen containing heterocyclic carbene ligand (L).

Examples of the monodentate phosphine ligands (P) include bis(pentafluorophenyl)phenylphosphine, (4-bromophenyl)diphenylphosphine, diallylphenylphosphine, dicyclohexylphenylphosphine, diethylphenylphosphine, 4-(dimethylamino)phenyldiphenylphosphine, dimethylphenylphosphine, diphenyl(2-methoxyphenyl)phosphine, diphenyl(pentafluorophenyl)phosphine, diphenylpropylphosphine, diphenyl-2-pyridylphosphine, diphenyl(p-tolyl)phosphine, diphenylvinylphosphine, ethyldiphenylphosphine, isopropyldiphenylphosphine, methyldiphenylphosphine, tribenzylphosphine, tributylphosphine, tri-t-butylphosphine, tricyclohexylphosphine, tricyclopentylphosphine, triethylphosphine, tri-2-furylphosphine, triisobutylphosphine, triisopropylphosphine, tripropylphosphine, trimethylphosphine, trioctylphosphine, triphenylphosphine, tris(4-chlorophenyl)phosphine, tris(3-chlorophenyl)phosphine, tris(2,6-dimethoxyphenyl)phosphine, tris(4-fluorophenyl)phosphine, tris(3-fluorophenylphosphine), tris(4-methoxyphenyl)phosphine, tris(3-methoxyphenyl)phosphine, tris(2-methoxyphenyl)phosphine, tris(4-trifluoromethylphenyl)phosphine, tris(pentafluorophenyl)phosphine, tris(2,4,6-trimethoxyphenyl)phosphine, tris(2,4,6-trimethylphenyl)phosphine, tri-m-tolylphosphine, tri-o-tolylphosphine, tri-p-tolylphosphine, benzyldiphenylphosphine, bis(2-methoxyphenyl)phenylphosphine, diphenylcyclohexylphosphine, 2-(di-t-butylphosphino)biphenyl, 2-(dicyclohexylphosphino)biphenyl, neomenthyldiphenylphosphine, p-tolyldiphenylphosphine, triallylphosphine, 2,4,4-trimethylpentylphosphine, tri(1-naphthyl)phosphine, tris(hydroxymethyl)phosphine, tris(hydroxypropyl)phosphine and the like. With respect to the monodentate phosphine ligand, a product commercially available can be directly used.

The substituted ethynyl gold phosphine complex is obtained as shown in, for example, the reaction scheme (2):

Reaction scheme (2)

wherein X and P are as defined above, and Y represents a halogen atom
by reacting a gold halogenophosphine complex with a substituted ethyne (see, for example, Non-patent document 1).

The gold halogenophosphine complex can be synthesized by a known method (see, for example, Non-patent document 2).

With respect to the substituted ethyne, a product commercially available may be directly used, but, when the substituted ethyne is an ethynyl group-substituted fused heterocyclic compound represented by the general formula (14):

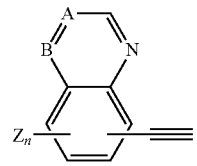

wherein Z represents a halogen atom, an alkyl group, an alkenyl group, an aryl group, an aralkyl group, an alkoxy group, an aryloxy group, a nitro group, a cyano group or a dialkylamino group, and n is an integer of 0 to 6; more than one Z, which may be identical or different from each other, represents the alkyl group, the alkenyl group, the aryl group, the aralkyl group, the alkoxy group, the aryloxy group or the dialkylamino group, the adjacent groups may be bonded together to form a ring; and each of A and B represents a methine group or a nitrogen atom, and when A or B, or both A and B are a methine group, a hydrogen atom thereof may be replaced by a group represented by Z or an ethynyl group,
namely, an ethynyl group-substituted fused heterocyclic compound substituted by a quinolyl group, a quinazolyl group or a quinoxalyl group, the compound is obtained as shown in the reaction scheme (3):

Reaction scheme (3)

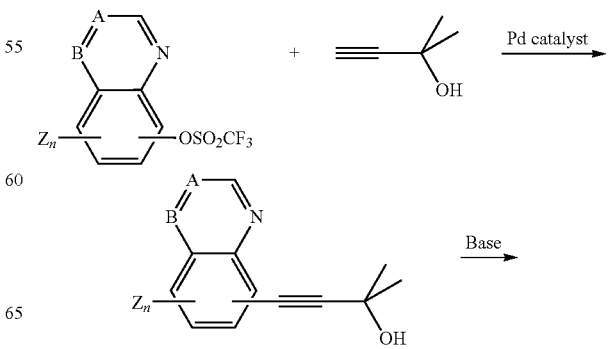

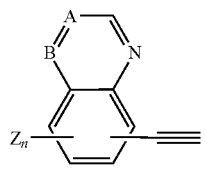

wherein Z, n, A and B are as defined above
by reacting a fused heterocyclic compound substituted by a trifluoromethanesulfonyloxy group with 2-methyl-3-butyn-2-ol in the presence of a palladium catalyst to yield a 1-dimethylhydroxymethyl-fused heterocyclic acetylene compound, and then reacting the resulting compound with a base.

The fused heterocyclic compound substituted by a trifluoromethanesulfonyloxy group is obtained as shown in, for example, the reaction scheme (4):

Reaction scheme (4)

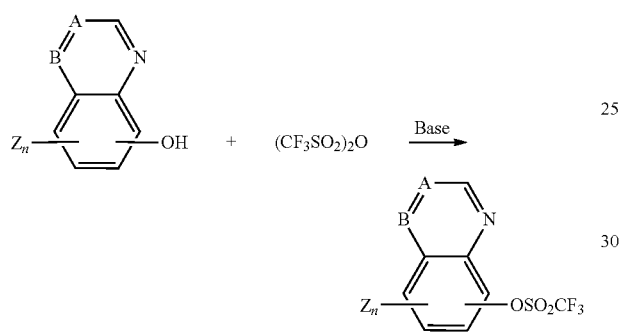

by reacting a fused heterocyclic compound substituted by a hydroxyl group with trifluoromethanesulfonic anhydride in the presence of a base (see, for example, Non-patent document 3).

Specific examples of the ethynyl group-substituted fused heterocyclic compounds include 8-quinolylethyne, 7-quinolylethyne, 6-quinolylethyne, 5-quinolylethyne, 4-quinolylethyne, 3-quinolylethyne, 2-quinolylethyne, 8-quinazolylethyne, 7-quinazolylethyne, 6-quinazolylethyne, 5-quinazolylethyne, 8-quinoxalylethyne, 7-quinoxalylethyne, 6-quinoxalylethyne, 5-quinoxalylethyne, 5-fluoro-8-quinolylethyne, 5-chloro-8-quinolylethyne, 5-fluoro-8-quinazolylethyne, 5-chloro-8-quinazolylethyne, 5-fluoro-8-quinoxalylethyne, 5-chloro-8-quinoxalylethyne and the like.

With respect to the nitrogen-containing heterocyclic carbene ligand, a product commercially available may be directly used, or a product synthesized by, for example, a known method may be used (see, for example, Non-patent document 4 and Patent document 1).

In the synthesis of the substituted ethynyl gold-nitrogen containing heterocyclic carbene complex of the present invention, the amount of the nitrogen-containing heterocyclic carbene ligand used is preferably 1 to 3 mol, further preferably 1 to 1.5 mol, relative to 1 mol of the substituted ethynyl gold phosphine complex.

With respect to the solvent used in the synthesis of the substituted ethynyl gold-nitrogen containing heterocyclic carbene complex of the present invention, there is no particular limitation as long as the solvent does not inhibit the reaction, and there is used, for example, an ether such as tetrahydrofuran, furan, dioxane, tetrahydropyran, diethyl ether, diisopropyl ether or dibutyl ether; an aliphatic hydrocarbon such as pentane, hexane, heptane or octane; an aromatic hydrocarbon such as benzene, toluene or xylene; a halogenated aliphatic hydrocarbon such as dichloromethane, dichloroethane or dichloropropane; or a halogenated aromatic hydrocarbon such as chlorobenzene. These solvents may be used alone or in combination with each other.

The amount of the solvent used is appropriately adjusted depending on homogeneity or stirred state of the reaction solution, but the amount is preferably 1 to 30 L, further preferably 5 to 20 L, relative to 1 mol of the substituted ethynyl gold phosphine complex.

The substituted ethynyl gold-nitrogen containing heterocyclic carbene complex of the present invention is synthesized by, for example, a method in which a substituted ethynyl gold phosphine complex, a nitrogen containing heterocyclic carbene ligand (formed by reacting a nitrogen containing heterocyclic hydrohalide with a base) and a solvent are mixed to effect a reaction while stirring. In this method, the reaction temperature is preferably 0 to 120° C., further preferably 20 to 100° C., and with respect to the reaction pressure, there is no particular limitation.

After completion of the reaction, the substituted ethynyl gold-nitrogen containing heterocyclic carbene complex of the present invention is isolated and purified by a known method, such as neutralization, extraction, filtration, concentration, distillation, recrystallization, sublimation, or chromatography.

Examples of the substituted ethynyl gold-nitrogen containing heterocyclic carbene complexes of the present invention include the following formulae (15) to (62):

(15)

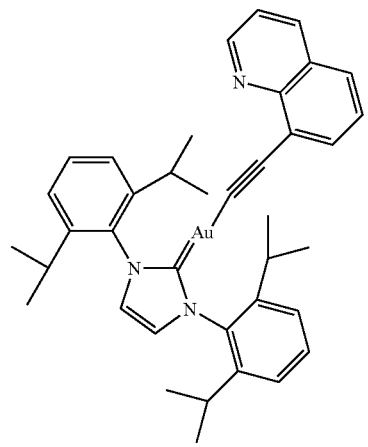

Au(IPr)(8QE)

(16)

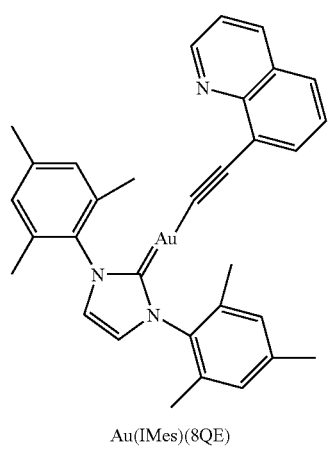

Au(IMes)(8QE)

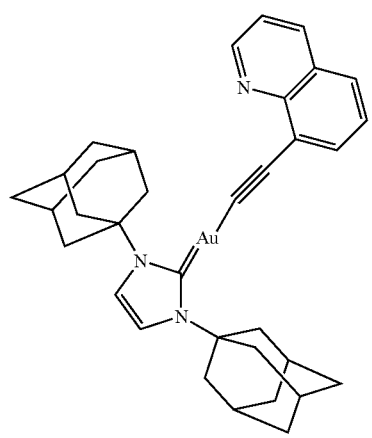
Au(IAd)(8QE)  (17)
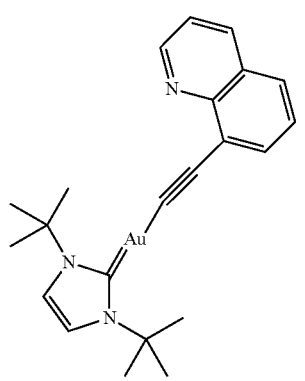
Au(ItBu)(8QE)  (18)
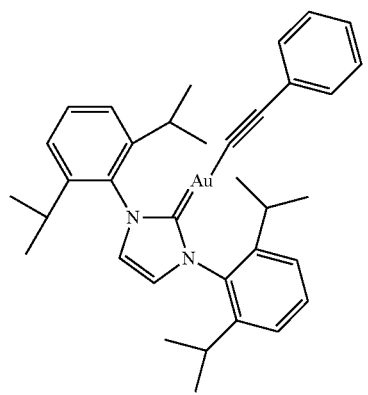
Au(IPr)(PE)  (19)
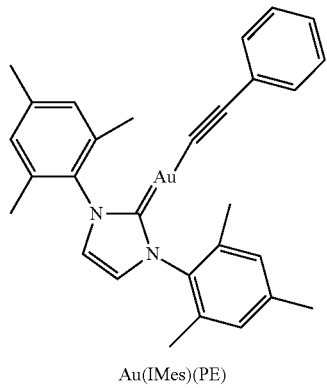
Au(IMes)(PE)  (20)
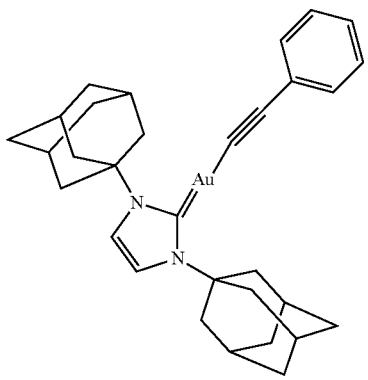
Au(IAd)(PE)  (21)
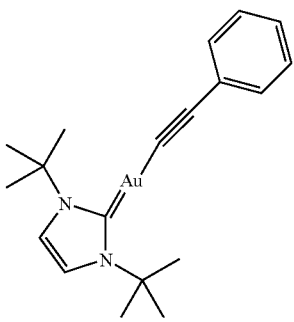
Au(ItBu)(PE)  (22)
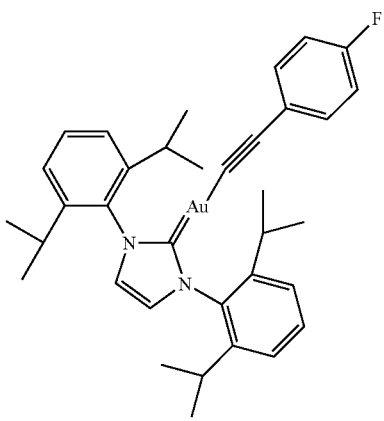
Au(IPr)(4F-PE)  (23)
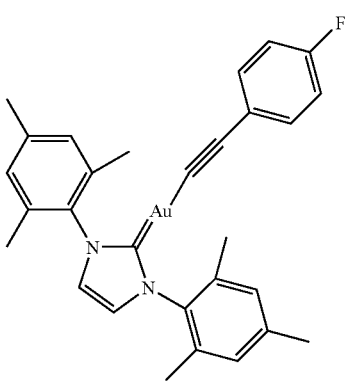
Au(IMes)(4F-PE)  (24)

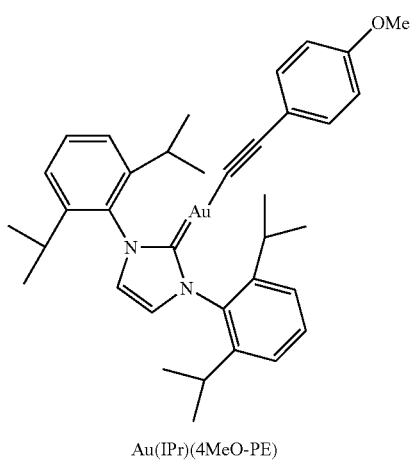
Au(IPr)(4MeO-PE)
(25)
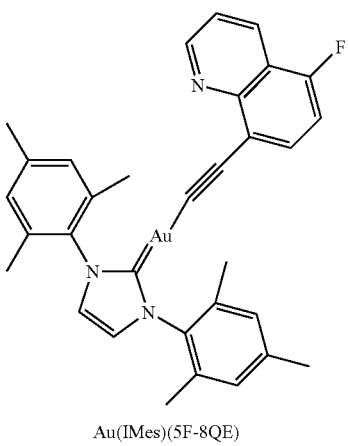
Au(IMes)(5F-8QE)
(28)
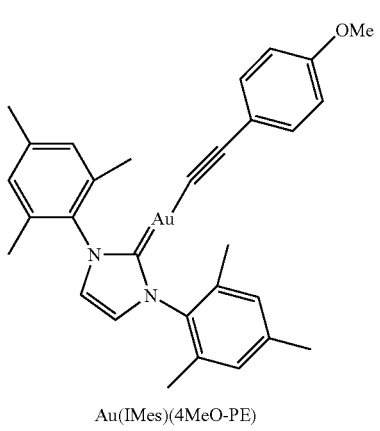
Au(IMes)(4MeO-PE)
(26)
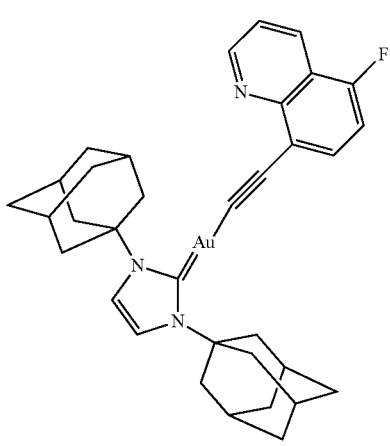
Au(IAd)(5F-8QE)
(29)
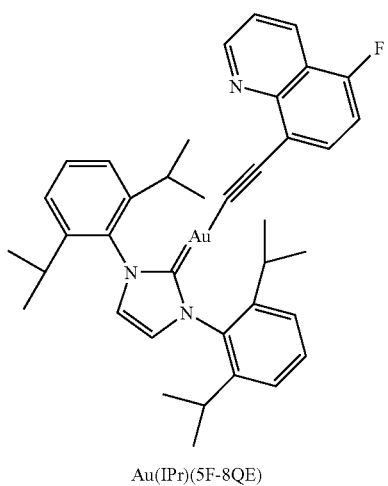
Au(IPr)(5F-8QE)
(27)
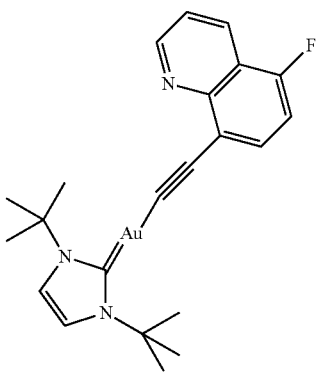
Au(ItBu)(5F-8QE)
(30)

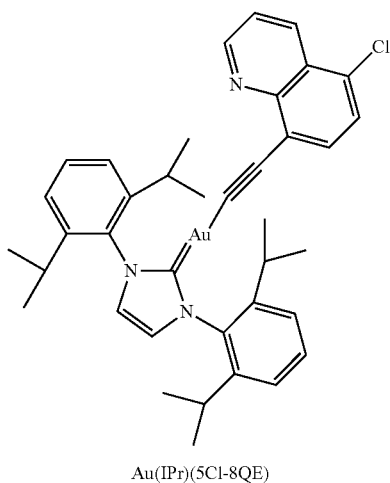
Au(IPr)(5Cl-8QE) (31)
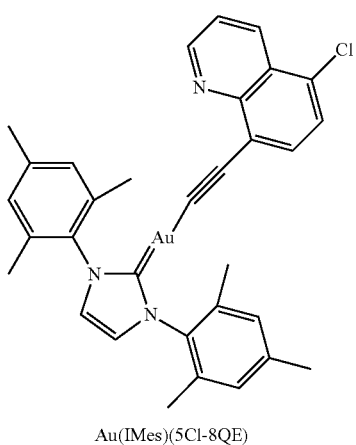
Au(IMes)(5Cl-8QE) (32)
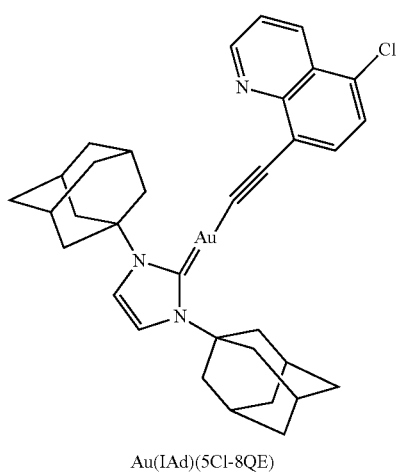
Au(IAd)(5Cl-8QE) (33)
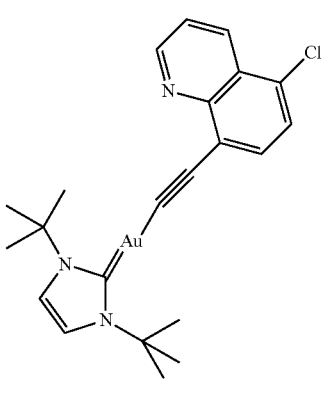
Au(ItBu)(5Cl-8QE) (34)
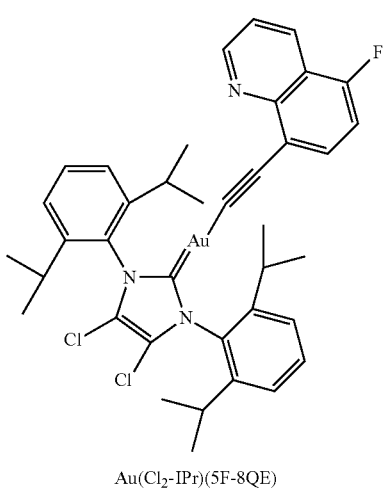
Au(Cl$_2$-IPr)(5F-8QE) (35)
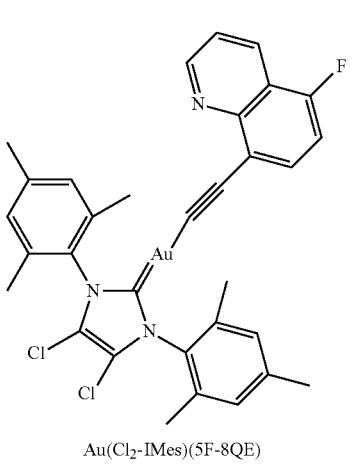
Au(Cl$_2$-IMes)(5F-8QE) (36)

(37)
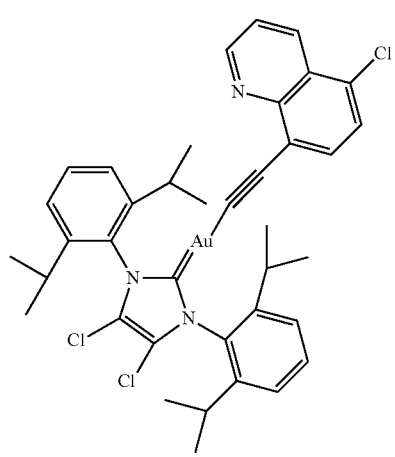
Au(Cl₂-IPr)(5Cl-8QE)
(38)
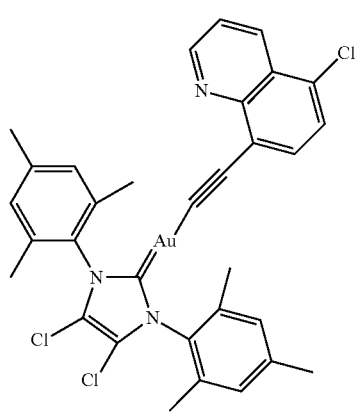
Au(Cl₂-IMes)(5Cl-8QE)
(39)
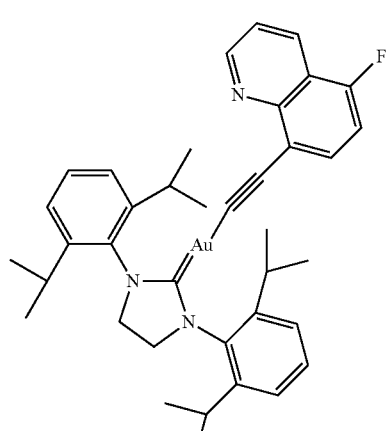
Au(H₂-IPr)(5F-8QE)
(40)
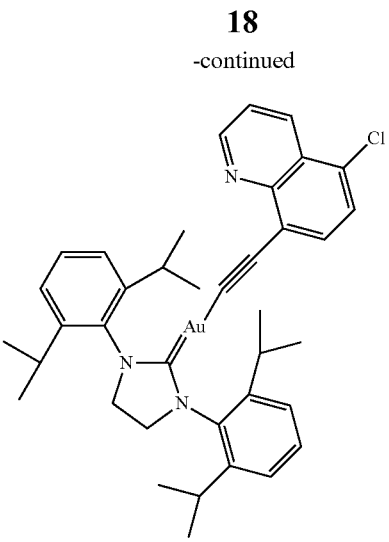
Au(H₂-IPr)(5Cl-8QE)
(41)
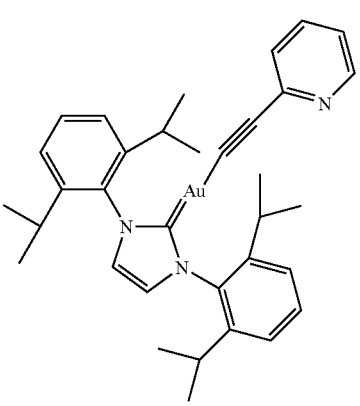
Au(IPr)(2PyE)
(42)
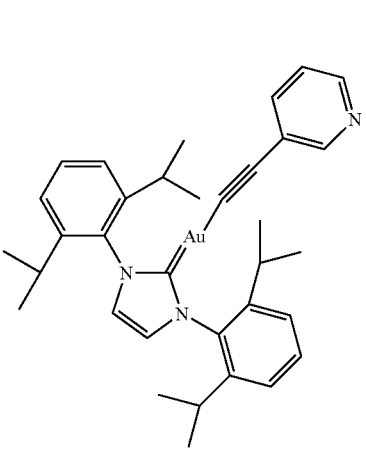
Au(IPr)(3PyE)

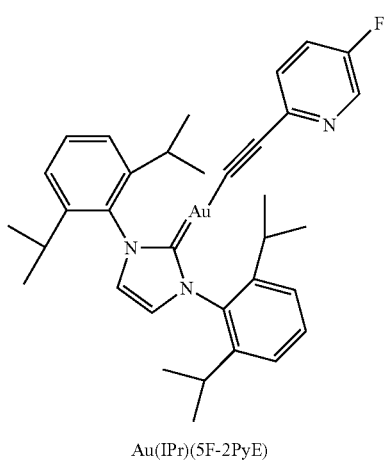
Au(IPr)(5F-2PyE)
(43)
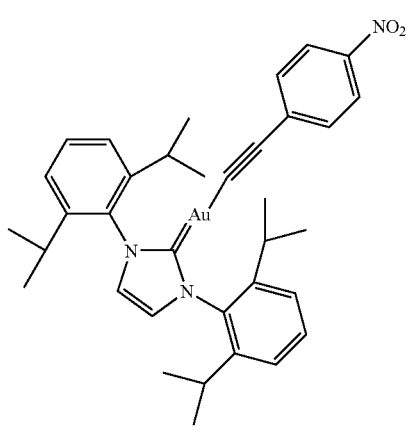
Au(IPr)(4NO₂-PE)
(46)
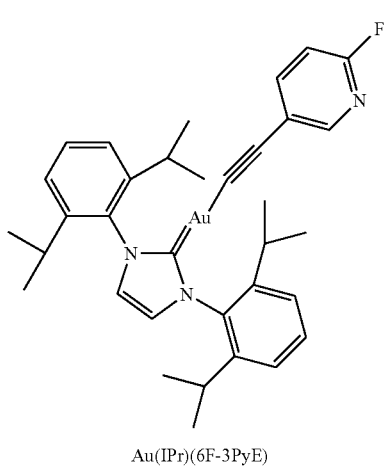
Au(IPr)(6F-3PyE)
(44)
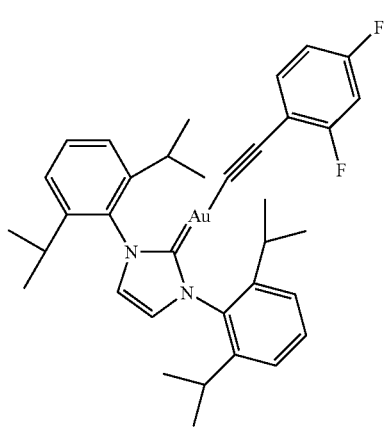
Au(IPr)(2,4-F₂-PE)
(47)
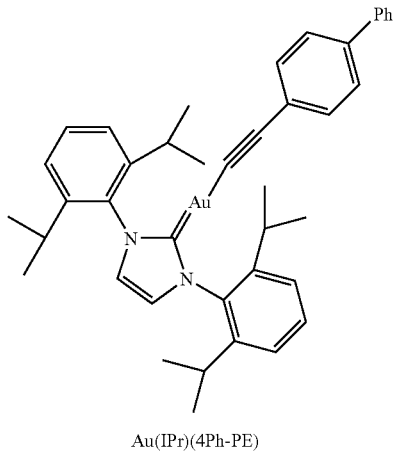
Au(IPr)(4Ph-PE)
(45)
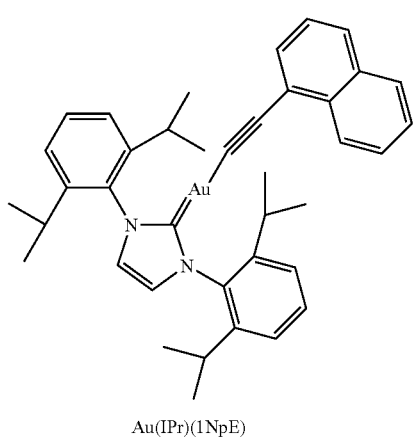
Au(IPr)(1NpE)
(48)

-continued
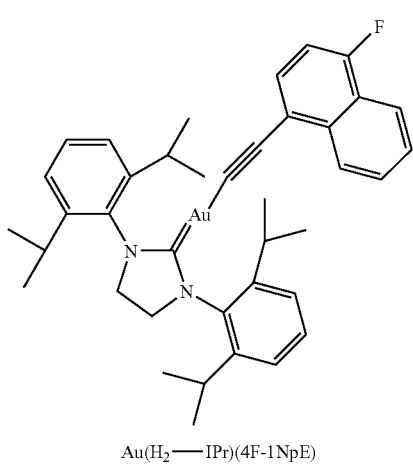
Au(H₂—IPr)(4F-1NpE)
(49)
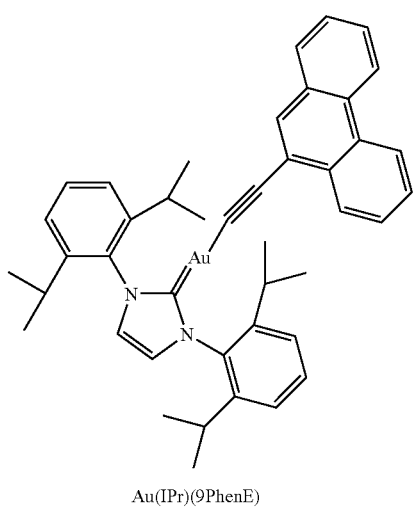
Au(IPr)(9PhenE)
(52)
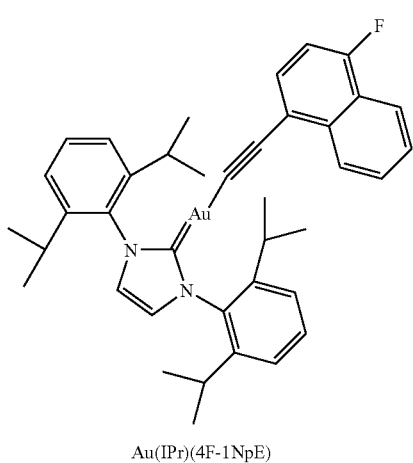
Au(IPr)(4F-1NpE)
(50)
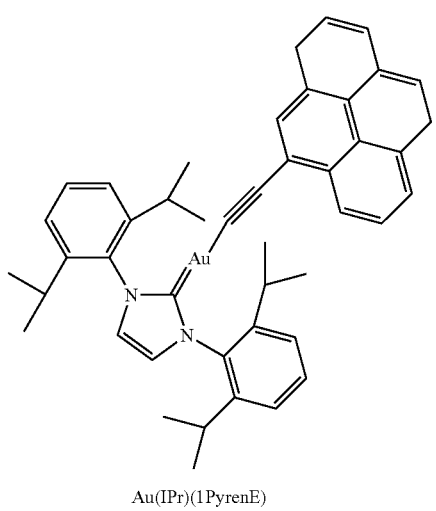
Au(IPr)(1PyrenE)
(53)
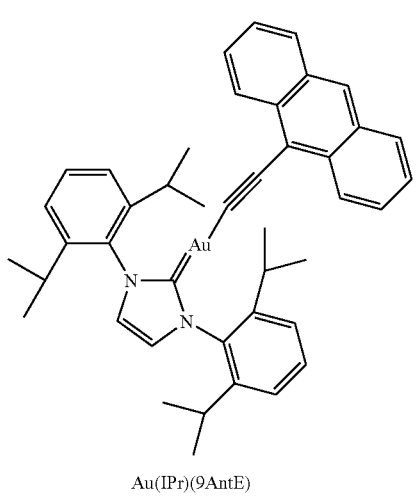
Au(IPr)(9AntE)
(51)
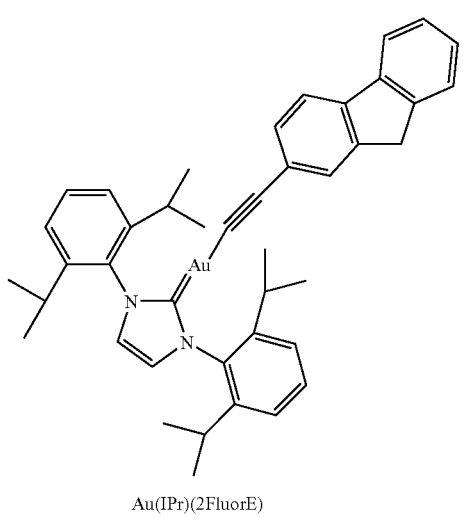
Au(IPr)(2FluorE)
(54)

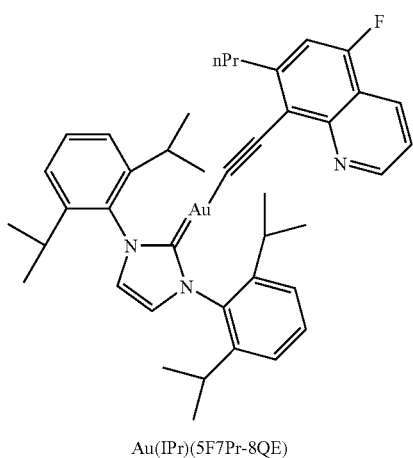
Au(IPr)(5F7Pr-8QE)
(55)
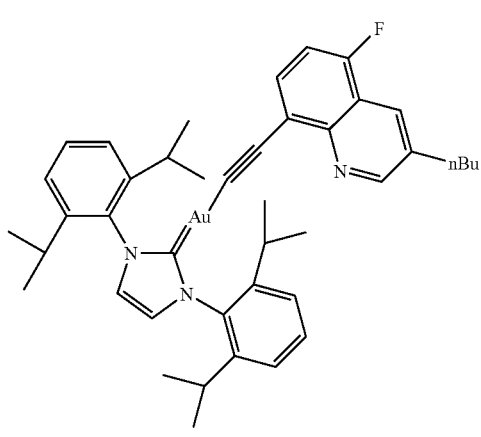
Au(IPr)(5F3Bu-8QE)
(56)
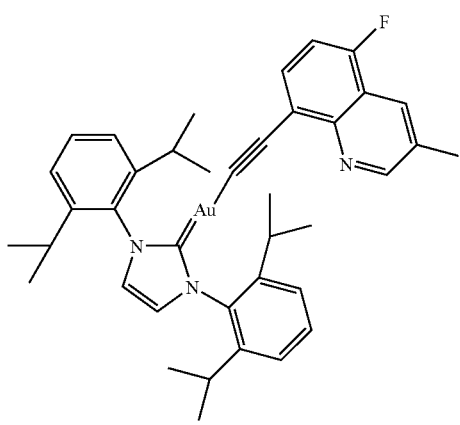
Au(IPr)(5F3Me-8QE)
(57)
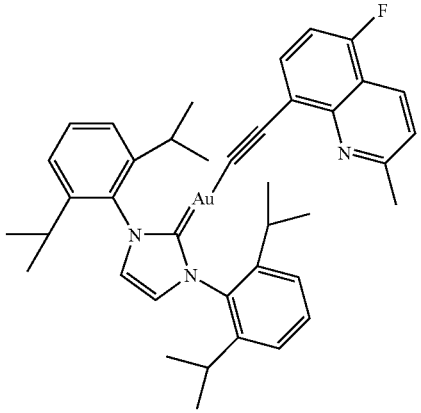
Au(IPr)(5F2Me-8QE)
(58)
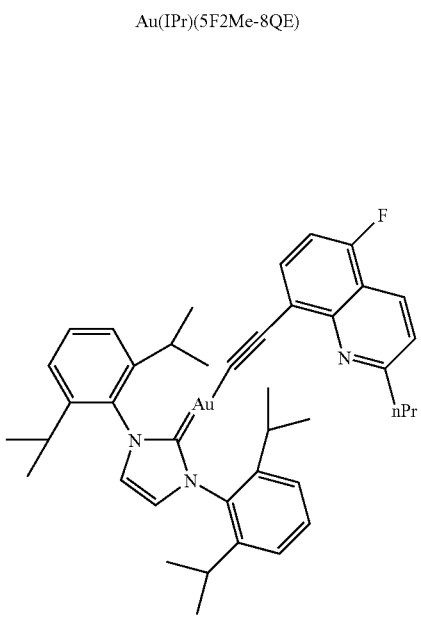
Au(IPr)(5F2Pr-8QE)
(59)
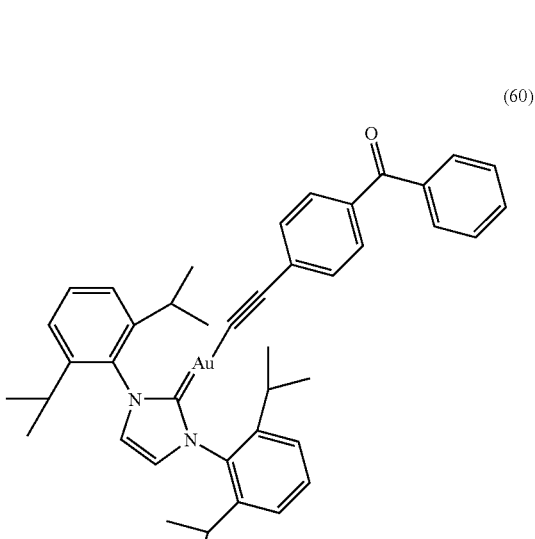
Au(IPr)(4Bz-PE)
(60)

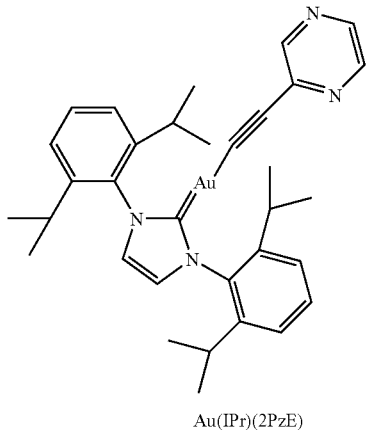

Au(IPr)(2PzE)

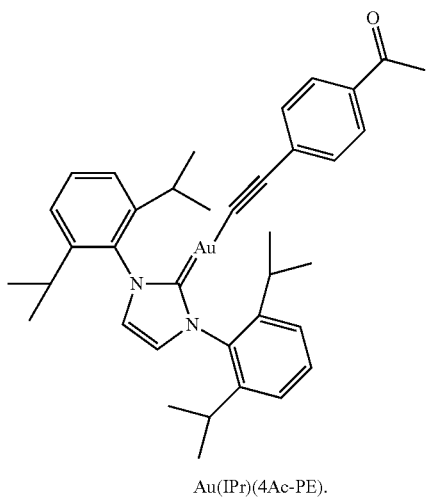

Au(IPr)(4Ac-PE).

The substituted ethynyl gold-nitrogen containing heterocyclic carbene complex of the present invention emits blue light with the CIE chromaticity coordinates (0.150, 0.060) to (0.218, 0.385) and green light with the coordinates (0.187, 0.452) to (0.324, 0.554) in chloroform at a temperature of 77 K (kelvin) under ultraviolet light radiation, which suggests that the complex is advantageously used as an organic electroluminescent device.

With respect to the substituted ethynyl gold-nitrogen containing heterocyclic carbene complex of the present invention, examples of complexes emitting light in a blue region include after-mentioned compounds Nos. 15 to 44, 47, 51, 53, 55 to 59 and 61, and examples of complexes emitting light in a green region include after-mentioned compounds Nos. 45, 46, 48, 49, 50, 52, 54, 60 and 62.

Next, an embodiment of the organic electroluminescent device according to the present invention is described.

In the organic electroluminescent device of the present invention, at least one organic compound thin layer contains the substituted ethynyl gold-nitrogen containing heterocyclic carbene complex, and the organic electroluminescent device is preferably an organic electroluminescent device having a single organic compound layer or a plurality of organic compound layers between a pair of electrodes. The organic compound layer means a light emitting layer, an electron injection layer or a hole transport layer.

The organic electroluminescent device of a single layer type has a light emitting layer between an anode and a cathode. The light emitting layer contains a luminescent material, and may further contain a hole injection material or an electron injection material for transporting to the luminescent material holes injected from the anode or electrons injected from the cathode.

Examples of the organic electroluminescent devices of a multilayer type include those having a multilayer stacked structure, such as (anode/hole injection layer/light emitting layer/cathode), (anode/light emitting layer/electron injection layer/cathode) or (anode/hole injection layer/light emitting layer/electron injection layer/cathode).

The light emitting layer contains the substituted ethynyl gold-nitrogen containing heterocyclic carbene complex represented by the formula (1), and may further contain, for example, at least one material selected from the group consisting of a known light emitting material, a doping material, a hole injection material (e.g., a phthalocyanine derivative, a naphthalocyanine derivative, a porphyrin derivative, oxazole, oxadiazole, triazole, imidazole, imidazolone, imidazolethione, pyrazoline, pyrazolone, tetrahydroimidazole, oxazole, oxadiazole, hydrazone, acylhydrazone, polyarylalkane, stilbene, butadiene, benzidine-type triphenylamine, styrylamine-type triphenylamine, diamine-type triphenylamine or derivatives thereof, or a polymer material, such as polyvinylcarbazole, polysilane or a conductive polymer) and an electron injection material (e.g., fluorenone, anthraquinodimethane, diphenoquinone, thiopyran dioxide, oxazole, oxadiazole, triazole, imidazole, perylenetetracarboxylic acid, fluorenylidenemethane, anthraquinodimethane, anthrone, or derivatives thereof).

The amount of the substituted ethynyl gold-nitrogen containing heterocyclic carbene complex added to the organic compound layer is 0.005 to 1 g, relative to 1 g of the organic compound layer.

In the organic electroluminescent device, the light emitting materials, other doping materials, hole injection materials and electron injection materials can be used in combination. Further, the hole injection layer, light emitting layer and electron injection layer may be individually formed by a layer construction comprised of two or more layers. In this case, with respect to the hole injection layer, a layer which injects holes from an electrode is called a hole injection layer, and a layer which receives holes from the hole injection layer and transports the holes to a light emitting layer is called a hole transport layer. Similarly, with respect to the electron injection layer, a layer which injects electrons from an electrode is called an electron injection layer, and a layer which receives electrons from the electron injection layer and transports the electrons to a light emitting layer is called an electron transport layer. These layers are appropriately selected and used depending on factors, such as an energy level or heat resistance of the material or adhesion to the organic compound layer or metal electrode.

Examples of luminescent materials or host materials usable in the organic compound layer, together with the substituted ethynyl gold-nitrogen containing heterocyclic carbene complex, include fused polycyclic aromatic compounds (e.g., anthracene, naphthalene, phenanthrene, pyrene, tetracene, pentacene, coronene, chrysene, fluorescein, perylene, rubrene and derivatives thereof), aromatic silicon compounds (e.g., phthaloperylene, naphthaloperylene, perynone, phthaloperynone, naphthaloperynone, diphenylbutadiene, tetraphenylbutadiene, coumarin, oxadiazole, aldazine, bisbenzoxazoline, bisstyryl, pyrazine, cyclopentadiene, quinoline metal complexes, aminoquinoline metal complexes, benzoquinoline metal complexes, imine, diphenylethylene, vinylanthracene, diaminocarbazole, pyran, thiopyran, polymethine, merocyanine, imidazole chelated oxinoid compounds, quinacridone, rubrene, stilbene based derivatives, and tetraphenylsilane), aromatic germanium compounds (e.g., tetraphenylgermanium), fluorescent dyes and the like.

Among the known hole injection materials usable in the organic electroluminescent device of the present invention, a further effective hole injection material is an aromatic tertiary amine derivative or a phthalocyanine derivative, and specific examples include, but are not limited to, aromatic tertiary amine derivatives, such as triphenylamine, tritolylamine, tolyldiphenylamine, N,N'-diphenyl-N,N'-(3-methylphenyl)-1,1'-biphenyl-4,4'-diamine (hereinafter, referred to as "TPD"), N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-di-α-naphthyl-1,1'-biphenyl-4,4'-diamine (hereinafter, referred to as "α-NPD"), N,N'-(methylphenyl)-N,N'-(4-n-butylphenyl)-phenanthrene-9,10-diamine, N,N-bis(4-di-4-tolylaminophenyl)-4-phenyl-cyclohexane, and oligomers or polymers having the above aromatic tertiary amine skeleton; and phthalocyanine derivatives and naphthalocyanine derivatives, such as $H_2PC$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, and GaPc-O—GaPc.

In the organic electroluminescent device of the present invention, a further effective, known electron injection material is a metal complex compound or a nitrogen-containing five-membered ring derivative (preferably oxazole, thiazole, oxadiazole, thiadiazole or triazole derivatives), examples thereof include, but are not limited to, metal complex compounds, such as 8-hydroxyquinolinatolithium, bis(8-hydroxyquinolinato)zinc, bis(8-hydroxyquinolinato)copper, bis(8-hydroxyquinolinato)manganese, tris(8-hydroxyquinolinato)aluminum (hereinafter, referred to as "$Alq_3$"), tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum and bis(2-methyl-8-quinolinato)(2-naphtholato)gallium; and nitrogen-containing five-membered ring derivatives, such as 2,5-bis(1-phenyl)-1,3,4-oxazole, dimethyl POPOP {wherein POPOP represents 1,4-bis(5-phenyloxazole-2-yl)benzene}, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole and 1,4-bis[2-(5-phenyltriazolyl)]benzene.

In the organic electroluminescent device of the present invention, for improving the electron injection properties, an inorganic compound layer can be formed between the light emitting layer and the electrode.

As an inorganic compound layer, an alkali metal fluoride, such as LiF; an alkaline earth metal fluoride, such as $BaF_2$ or $SrF_2$; an alkali metal oxide, such as $Li_2O$; or an alkaline earth metal oxide, such as RaO or SrO, can be used.

As a conductive material for the anode in the organic electroluminescent device of the present invention, there can be used a conductive material having a work function larger than around 4 eV, for example, carbon atom, aluminum, vanadium, iron, cobalt, nickel, tungsten, silver, gold, platinum, palladium, or an alloy thereof, an ITO (substance comprising indium oxide containing tin oxide in an amount of 5 to 10%) substrate, a metal oxide used in an NESA substrate, such as tin oxide or indium oxide, or an organic conductive resin, such as polythiophene or polypyrrole. It is desired to use in the anode a conductive material having a work function larger by 0.1 eV or more than the work function of the conductive material used in the cathode of the device.

As a conductive material for the cathode, a conductive substance having a work function smaller than around 4 eV, for example, magnesium, calcium, tin, lead, titanium, yttrium, lithium, ruthenium, manganese, aluminum, or an alloy thereof can be used. Examples of the alloys include magnesium/silver, magnesium/indium, lithium/aluminum and the like. With respect to the metal ratio in the alloy, there is no particular limitation, and it is controlled by changing the temperature of the deposition source, the atmosphere, the degree of vacuum or the like. It is desired to use in the cathode a conductive material having a work function smaller by 0.1 eV or more than the work function of the conductive material used in the anode of the device.

The anode and cathode may be individually formed by a layer construction comprised of two or more layers, if necessary.

In the organic electroluminescent device of the present invention, it is desired that at least one surface is transparent in the wavelength region of the light emitted by the device. Further, the substrate is desirably transparent.

The transparent electrode is obtained using the above conductive material by a vapor deposition or sputtering process under conditions such that the electrode surely has predetermined light transmission properties.

The electrode on the emission side desirably has a transmittance of 10% or more.

With respect to the substrate, there is no particular limitation as long as it has mechanical and thermal strength and transparency, but a glass substrate or a transparent resin film can be used.

Examples of transparent resin films include polyethylene, ethylene-vinyl acetate copolymers, ethylene-vinyl alcohol copolymers, polypropylene, polystyrene, polymethyl methacrylate, polyvinyl chloride, polyvinyl alcohol, polyvinyl butyral, nylon, polyether ether ketone, polysulfone, polyether sulfone, tetrafluoroethylene-perfluoroalkyl vinyl ether copolymers, polyvinyl fluoride, tetrafluoroethylene-ethylene copolymers, tetrafluoroethylene-hexafluoropropylene copolymers, polychlorotrifluoroethylene, polyvinylidene fluoride, polyesters, polycarbonates, polyurethanes, polyimides, polyether imides, polyimides, polypropylene and the like.

In the organic electroluminescent device of the present invention, for improving the stability with respect to the temperature, humidity or atmosphere, a protective layer may be formed on the surface of the device, or the whole of the device may be protected by silicone oil, a resin or the like.

Each layer in the organic electroluminescent device can be formed by a dry film formation process, such as vacuum deposition, sputtering, plasma or ion plating, or a wet film formation process, such as spin coating, dipping or flow coating. With respect to the thickness of the layer, there is no particular limitation, but the thickness is preferably 5 nm to 10 μm, further preferably 10 nm to 0.2 μm.

When using a wet film formation process, the substituted ethynyl gold-nitrogen containing heterocyclic carbene complex is dissolved or dispersed in a solvent, such as ethanol, chloroform, tetrahydrofuran, or dioxane, thus forming a thin film on each layer.

As a dry film formation process, preferred is vapor deposition, and, using a vapor deposition machine at a degree of vacuum of $2\times10^{-3}$ Pa or less and at a substrate temperature of room temperature, the substituted ethynyl gold-nitrogen containing heterocyclic carbene complex of the present invention placed in a deposition cell is heated and evaporated, thus forming a thin film. In this instance, for controlling the temperature of the deposition source, a thermocouple in contact with the deposition cell or a non-contact infrared thermometer can be preferably used. For controlling the deposition rate, a deposition film thickness meter can be preferably used.

As a deposition film thickness meter, there can be preferably used a thickness meter in a system such that, using a quartz crystal oscillator disposed opposite the deposition source, a weight of the film deposited on the surface of the quartz crystal oscillator is measured from a change of the oscillation frequency of the oscillator and a film thickness is determined in real time from the weight measured.

Co-deposition of a host material, such as CBP, and the substituted ethynyl gold-nitrogen containing heterocyclic carbene complex of the present invention can be performed by using individual deposition sources and independently controlling the individual temperatures.

In each organic thin film layer, for improving the film forming properties or for preventing pinholes from being caused in the film, a resin, e.g., an insulating resin, such as polystyrene, polycarbonate, polyacrylate, polyester, polyamide, polyurethane, polysulfone, polymethyl methacrylate, polymethyl acrylate, cellulose, or a copolymer thereof, a photoconductive resin, such as poly-N-vinylcarbazole or polysilane, or a conductive resin, such as polythiophene or polypyrrole, or an additive, such as an antioxidant, an ultraviolet absorber, or a plasticizer, may be used.

The organic electroluminescent device of the present invention can be used in a flat luminescent object, such as a flat panel display for wall television or mobile phone, a backlight for copy machine, printer or liquid crystal display, a light source for instruments, a display board, a sign lamp or the like.

EXAMPLE

Nextly, the present invention is specifically explained by listing Examples but a scope of the present invention is not limited to these.

Example 1

Synthesis of Au(IPr)(8QE)[(8-quinolylethynyl)[1,3-bis(2,6-diisopropylphenyl)imidazol-2-ylidene]gold]

Under an argon atmosphere, 1,3-bis(2,6-diisopropylphenyl)imidazolium chloride (IPrH$^+$Cl$^-$; 0.21 g, 0.05 mmol), potassium tert-butoxide (85 mass % article, 83 mg, 0.63 mmol) and tetrahydrofuran (5.0 ml) were added to a 25 ml Schlenk tube and the mixture was stirred at room temperature for 20 minutes. After tetrahydrofuran was distilled off under reduced pressure, toluene (7.5 ml) was added thereto. After the mixture was stirred at 70° C. for 5 minutes, the reaction mixture was filtered. The filtrate was added dropwise to the other 25 ml Schlenk tube added with 8-quinolylethynyl(triphenylphosphine)gold (229 mg, 0.375 mmol) and 7.5 ml of toluene. After completion of the dropwise addition, the reaction mixture was heated at 70° C. for 4 hours. The reaction mixture was cooled to room temperature, and then toluene was distilled off under reduced pressure. The resulting residue was extracted with ether (20 ml), the insolubles were filtered off, and the ether extract was concentrated and recrystallized in a n-hexane-diethyl ether system to give 0.21 g of the desired compound as a white solid (yield: 73%).

$^1$H-NMR (300 MHz, CDCl$_3$) δ: 8.91 (dd, 1H), 8.01 (dd, 1H), 7.79 (dd, 1H), 7.53-7.48 (m, 3H), 7.33-7.25 (m, 6H), 7.12 (s, 2H), 2.64 (sept, 4H), 1.40 (d, 12H), 1.22 (d, 12H)

FAB-MS (M/Z): 738 (M+H)$^+$

Luminescence analysis: (CHCl$_3$, 77K, Ex250 nm) λ (nm): 387 (max), 533,571

Elemental Analysis:

| Found | C: 62.13, H: 5.83, N: 5.65 |
|---|---|
| Theoretical | C: 61.87, H: 5.74, N: 5.70 |

Example 2

Synthesis of Au(IMes)(8QE)[(8-quinolylethynyl)[1,3-bis(2,4,6-trimethylphenyl)imidazol-2-ylidene]gold]

Under an argon atmosphere, 1,3-bis(2,4,6-trimethylphenyl)imidazolium chloride (IMesH$^+$Cl$^-$; 0.19 g, 0.53 mmol), potassium tert-butoxide (85 mass % article, 83 mg, 0.63 mmol) and tetrahydrofuran (5.0 ml) were added to a 25 ml Schlenk tube, and the mixture was stirred at room temperature for 20 minutes. After tetrahydrofuran was distilled off under reduced pressure, toluene (7.5 ml) was added thereto and the mixture was stirred at 70° C. for 5 minutes. The reaction mixture was filtered and the filtrate was added dropwise to the other 25 ml Schlenk tube added with 8-quinolylethynyl(triphenylphosphine)gold (229 mg, 0.375 mmol) and toluene (7.5 ml). After completion of the dropwise addition, the reaction mixture was heated at 70° C. for 8 hours. The reaction mixture was cooled to room temperature, and then the precipitate was collected by filtration and washed with toluene (20 ml). The precipitate was dried under reduced pressure to give 0.22 g of the desired compound as a bluish white solid (yield: 91%).

$^1$H-NMR (300 MHz, CDCl$_3$) δ: 8.95 (dd, 1H), 8.03 (dd, 1H), 7.81 (dd, 1H), 7.54 (dd, 1H), 7.34-7.25 (m, 2H), 7.05 (s, 2H), 6.98 (s, 4H), 2.34 (s, 6H), 2.13 (s, 12H)

FAB-MS (M/Z): 654 (M+H)$^+$

Luminescence analysis: (CHCl$_3$, 77K, Ex250 nm) λ (nm): 385 (max), 530, 570

Elemental Analysis:

| Found | C: 59.06, H: 4.52, N: 6.31 |
|---|---|
| Theoretical | C: 58.81, H: 4.63, N: 6.43 |

Example 3

Synthesis of Au(IAd)(8QE)[8-quinolylethynyl][1,3-diadamantylimidazol-2-ylidene]gold))

Under an argon atmosphere, 1,3-diadamantylimidazolium chloride (IAdH$^+$Cl$^-$; 0.053 g, 0.14 mmol), potassium tert-butoxide (85 mass % article, 24 mg, 0.19 mmol) and tetrahydrofuran (2.0 ml) were added to a 25 ml Schlenk tube, and the mixture was stirred at room temperature for 20 minutes. After tetrahydrofuran was distilled off under reduced pressure, toluene (3 ml) was added thereto and the mixture was stirred at 70° C. for 5 minutes. The reaction mixture was filtered and the filtrate was added dropwise to the other 25 ml Schlenk tube added with 8-quinolylethynyl(triphenylphosphine)gold (67 mg, 0.11 mmol) and 3 ml of toluene. After completion of the dropwise addition, the reaction mixture was heated at 70° C. for 2.5 hours. The reaction mixture was cooled to room temperature, and then toluene was distilled off under reduced pressure and the resulting white solid was washed with diethyl ether (20 ml) to give 0.065 g of the desired compound as a white solid (yield: 87%).

$^1$H-NMR (300 MHz, CDCl$_3$) δ: 9.04 (dd, 1H), 8.09 (dd, 1H), 8.00 (dd, 1H), 7.60 (dd, 1H), 7.44-7.33 (m, 2H), 7.07 (s, 2H), 2.65-2.59 (m, 12H), 2.28 (m, 6H), 1.87-1.72 (m, 12H)

[FAB-MS] (M/Z): 686 (M+H)$^+$

Luminescence analysis: (CHCl$_3$, 77K, Ex250 nm) λ (nm): 387 (max)

Elemental Analysis:

| | |
|---|---|
| Found | C: 59.64, H: 5.48, N: 5.99 |
| Theoretical | C: 59.56, H: 5.59, N: 6.13 |

Example 4

Synthesis of Au(ItBu) (8QE) [(8-quinolylethynyl)[-1,3-di-tert-butylimidazol-2-ylidene]gold]

Under an argon atmosphere, 1,3-di-tert-butylimidazolium chloride (ItBuH$^+$Cl$^-$; 0.087 g, 0.40 mmol), potassium tert-butoxide (85 mass % article, 69 mg, 0.52 mmol) and tetrahydrofuran (6.5 ml) were added to a 25 ml Schlenk tube, and the mixture was stirred at room temperature for 20 minutes. After tetrahydrofuran was distilled off under reduced pressure, toluene (6.5 ml) was added thereto and the mixture was stirred at 70° C. for 5 minutes. The reaction mixture was filtered and the filtrate was added dropwise to the other 50 ml Schlenk tube added with 8-quinolylethynyl (triphenylphosphine) gold (188 mg, 0.31 mmol) and 6.5 ml of toluene. After completion of the dropwise addition, the reaction mixture was heated at 70° C. for 4 hours. The reaction mixture was cooled to room temperature, and then toluene was distilled off under reduced pressure and the resulting white solid was washed with diethyl ether (20 ml) to give 0.108 g of the desired compound as a white solid (yield: 66%).

$^1$H-NMR (300 MHz, CDCl$_3$) δ: 9.05 (dd, 1H), 8.09 (dd, 1H), 8.00 (dd, 1H), 7.62 (dd, 1H), 7.44-7.30 (m, 2H), 7.06 (s, 2H), 1.90 (s, 18H)

FAB-MS (M/Z): 530 (M+H)$^+$

Luminescence analysis: (CHCl$_3$, 77K, Ex240 nm) λ (nm): 387 (max)

Elemental Analysis:

| | |
|---|---|
| Found | C: 51.51, H: 4.85, N: 5.55 |
| Theoretical | C: 49.91, H: 4.95, N: 7.94 |

Example 5

Synthesis of Au(IPr)(PE)[(phenylethynyl)[1,3-bis(2,6-diisopropylphenyl)imidazol-2-ylidene]gold]

Under an argon atmosphere, 1,3-bis(2,6-diisopropylphenyl)imidazolium chloride (IPrH$^+$Cl$^-$; 0.053 g, 0.125 mmol), potassium tert-butoxide (85 mass % article, 21.5 mg, 0.16 mmol) and tetrahydrofuran (2.0 ml) were added to a 25 ml Schlenk tube and the mixture was stirred at room temperature for 20 minutes. After tetrahydrofuran was distilled off under reduced pressure, toluene (3 ml) was added thereto and the mixture was stirred at 70° C. for 5 minutes. The reaction mixture was filtered and the filtrate was added dropwise to the other 25 ml Schlenk tube added with phenylethynyl(triphenylphosphine)gold (54 mg, 0.096 mmol) and 3 ml of toluene. After completion of the dropwise addition, the reaction mixture was heated at 70° C. for 4 hours. The reaction mixture was cooled to room temperature, and then toluene was distilled off under reduced pressure. The resulting residue was extracted with diethyl ether (20 ml) and the insolubles were filtered off. The diethyl ether extract was concentrated and recrystallized in a n-hexane-diethyl ether system to give 0.047 g of the desired compound as a white solid (yield: 71%).

$^1$H-NMR (300 MHz, CDCl$_3$) δ: 7.49 (dd, 2H), 7.31-7.28 (m, 6H), 7.12 (s, 2H), 7.10-7.00 (m, 3H), 2.61 (sept, 4H), 1.38 (d, 12H), 1.21 (d, 12H)

FAB-MS (M/Z): 687 (M+H)$^+$

Luminescence analysis: (CHCl$_3$, 77K, Ex250 nm) λ (nm): 414 (max), 434, 454

Elemental Analysis:

| | |
|---|---|
| Found | C: 60.95, H: 5.92, N: 4.02 |
| Theoretical | C: 61.22, H: 6.02, N: 4.08 |

Example 6

Synthesis of Au(IMes)(PE)[(phenylethynyl)[1,3-bis(2,4,6-trimethylphenyl)imidazol-2-ylidene]gold]

Under an argon atmosphere, 1,3-bis(2,4,6-trimethylphenyl)imidazolium chloride (IMesH$^+$Cl$^-$; 0.158 g, 0.464 mmol), potassium tert-butoxide (85 mass % article, 80.0 mg, 0.60 mmol) and tetrahydrofuran (7.5 ml) were added to a 25 ml Schlenk tube, and the mixture was stirred at room temperature for 20 minutes. After tetrahydrofuran was distilled off under reduced pressure, toluene (7.5 ml) was added thereto and the mixture was stirred at 70° C. for 5 minutes. The reaction mixture was filtered and the filtrate was added dropwise to the other 50 ml Schlenk tube added with phenylethynyl(triphenylphosphine)gold (200 mg, 0.357 mmol) and 7.5 ml of toluene. After completion of the dropwise addition, the reaction mixture was heated at 70° C. for 2.5 hours. The reaction mixture was cooled to room temperature, and then toluene was distilled off under reduced pressure. The resulting residue was extracted with diethyl ether (20 ml) and the insolubles were filtered off. The diethyl ether extract was concentrated and recrystallized in a n-hexane-diethyl ether system to give 0.183 g of the desired compound as a white solid.

$^1$H-NMR (300 MHz, CDCl$_3$) δ: 7.35-7.32 (m, 2H), 7.15-7.07 (m, 3H), 7.06 (s, 2H), 6.99 (s, 4H), 2.35 (s, 6H), 2.12 (s, 12H)

FAB-MS (M/Z): 603 (M+H)$^+$

Luminescence analysis: (CHCl$_3$, 77K, Ex240 nm) λ (nm): 414 (max), 434, 453

Elemental Analysis:

| | |
|---|---|
| Found | C: 57.65, H: 4.74, N: 4.48 |
| Theoretical | C: 57.81, H: 4.85, N: 4.65 |

Example 7

Synthesis of Au(IAd)(PE)[(phenylethynyl)[1,3-di-adamantylimidazol-2-ylidene]gold]

Under an argon atmosphere, 1,3-diadamantylimidazolium chloride (IAdH$^+$Cl$^-$; 0.108 g, 0.29 mmol), potassium tert-butoxide (85 mass % article, 50.0 mg, 0.38 mmol) and tetrahydrofuran (4.5 ml) were added to a 25 ml Schlenk tube, and the mixture was stirred at room temperature for 20 minutes. After tetrahydrofuran was distilled off under reduced pressure, toluene (4.5 ml) was added thereto and the mixture was stirred at 70° C. for 5 minutes. The reaction mixture was filtered and the filtrate was added dropwise to the other 50 ml Schlenk tube added with phenylethynyl(triphenylphosphine)gold (123 mg, 0.22 mmol) and 4.5 ml of toluene. After completion of the dropwise addition, the reaction mixture was heated at 70° C. for 2.5 hours. The reaction mixture was cooled to room temperature, and then toluene was distilled off under reduced pressure. The resulting residue was recrystallized in a methylene chloride-diethyl ether system to give 0.117 g of the desired compound as a white solid (yield: 84%).

$^1$H-NMR (300 MHz, CDCl$_3$) δ: 7.53-7.49 (m, 2H), 7.25-7.08 (m, 3H), 7.07 (s, 2H), 2.58-2.56 (m, 12H), 2.34-2.28 (m, 6H), 1.85-1.72 (m, 12H)

FAB-MS (M/Z): 635 (M+H)$^+$

Luminescence analysis: (CHCl$_3$, 77K, Ex240 nm) λ (nm): 415 (max), 435, 455

Elemental Analysis:

| | |
|---|---|
| Found | C: 58.71, H: 5.76, N: 4.44 |
| Theoretical | C: 58.67, H: 5.88, N: 4.41 |

Example 8

Synthesis of Au(ItBu)(PE)[(phenylethynyl)[1,3-di-tert-butylimidazol-2-ylidene]gold]

Under an argon atmosphere, 1,3-di-tert-butylimidazolium chloride (ItBuH$^+$Cl$^-$; 0.082 g, 0.38 mmol), potassium tert-butoxide (85 mass % article, 65 mg, 0.49 mmol) and tetrahydrofuran (6.0 ml) were added to a 25 ml Schlenk tube, and the mixture was stirred at room temperature for 20 minutes. After tetrahydrofuran was distilled off under reduced pressure, toluene (6.0 ml) was added thereto and the mixture was stirred at 70° C. for 5 minutes. The reaction mixture was filtered and the filtrate was added dropwise to the other 25 ml Schlenk tube added with phenylethynyl(triphenylphosphine)gold (168 mg, 0.30 mmol) and 6.0 ml of toluene. After completion of the dropwise addition, the reaction mixture was heated at 70° C. for 2.5 hours. The reaction mixture was cooled to room temperature, and then toluene was distilled off under reduced pressure. The resulting white solid was recrystallized in a methylene chloride-diethyl ether-hexane system to give 0.127 g of the desired compound as a white solid (yield: 89%).

$^1$H-NMR (300 MHz, CDCl$_3$) δ: 7.53-7.49 (m, 2H), 7.29-7.06 (m, 3H), 7.03 (s, 2H), 1.89 (s, 18H)

FAB-MS (M/Z): 479 (M+H)$^+$

Luminescence analysis: (CHCl$_3$, 77K, Ex240 nm) λ (nm): 414 (max) 434, 454

Elemental Analysis:

| | |
|---|---|
| Found | C: 47.30, H: 5.11, N: 5.76 |
| Theoretical | C: 47.70, H: 5.27, N: 5.86 |

Example 9

Synthesis of Au(IPr)(4F-PE)[(4-fluorophenylethynyl)[1,3-bis(2,6-diisopropylphenyl)imidazol-2-ylidene]gold]

Under an argon atmosphere, 1,3-bis(2,6-diisopropylphenyl)imidazolium chloride (IPrH$^+$Cl$^-$; 0.166 g, 0.39 mmol), potassium tert-butoxide (85 wt % article, 67 mg, 0.51 mmol) and tetrahydrofuran (6.0 ml) were added to a 25 ml Schlenk tube, and the mixture was stirred at room temperature for 20 minutes. After tetrahydrofuran was distilled off under reduced pressure, toluene (6.0 ml) was added thereto and the mixture was stirred at 70° C. for 5 minutes. The reaction mixture was filtered and the filtrate was added dropwise to the other 25 ml Schlenk tube added with 4-fluorophenylethynyl(triphenylphosphine)gold (174 mg, 0.30 mmol) and 6.0 ml of toluene. After completion of the dropwise addition, the reaction mixture was heated at 70° C. for 2.5 hours. The reaction mixture was cooled to room temperature, and then toluene was distilled off under reduced pressure. The resulting white solid was recrystallized in a n-hexane-diethyl ether-methylene chloride system to give 0.187 g of the desired compound as a white solid (yield: 88%).

$^1$H-NMR (300 MHz, CDCl$_3$) δ: 7.49 (dd, 2H), 7.30-7.22 (m, 8H), 7.12 (s, 2H), 6.82-6.75 (m, 2H), 2.60 (sept, 4H), 1.38 (d, 12H), 1.21 (d, 12H)

FAB-MS (M/Z): 705 (M+H)$^+$

Luminescence analysis: (CHCl$_3$, 77K, Ex250 nm) λ (nm): 412 (max), 430, 451

Elemental Analysis:

| | |
|---|---|
| Found | C: 59.32, H: 5.68, N: 3.95 |
| Theoretical | C: 59.66, H: 5.72, N: 3.98 |

Example 10

Synthesis of Au(IMes)(4F-PE)[(4-fluorophenylethynyl)[1,3-bis(2,4,6-trimethylphenyl)imidazol-2-ylidene]gold]

Under an argon atmosphere, 1,3-bis(2,4,6-trimethylphenyl)imidazolium chloride (IMesH$^+$Cl$^-$; 0.142 g, 0.416 mmol) and potassium tert-butoxide (85 mass % article, 71.0 mg, 0.541 mmol) and tetrahydrofuran (6.7 ml) were added to a 25 ml Schlenk tube, and the mixture was stirred at room temperature for 20 minutes. After tetrahydrofuran was distilled off under reduced pressure, toluene (6.7 ml) was added thereto and the mixture was stirred at 70° C. for 5 minutes. The reaction mixture was filtered and the filtrate was added dropwise to the other 50 ml Schlenk tube added with 4-fluorophenylethynyl(triphenylphosphine)gold (185 mg, 0.32 mmol) and 6.7 ml of toluene. After completion of the dropwise addition, the reaction mixture was heated at 70° C. for 2.5 hours. The reaction mixture was cooled to room temperature, and then toluene was distilled off under reduced pressure. The resulting white solid was recrystallized in a n-hexane-diethyl ether-methylene chloride system to give 0.150 g of the desired compound as a white solid (yield: 75%).

$^1$H-NMR (300 MHz, CDCl$_3$) δ: 7.32-7.26 (m, 2H), 7.06 (s, 2H), 6.99 (s, 4H), 6.81-6.78 (m, 2H), 2.35 (s, 6H), 2.12 (s, 12H)

FAB-MS (M/Z): 621 (M+H)$^+$

Luminescence analysis: (CHCl$_3$, 77K, Ex240 nm) λ (nm): 411 (max), 430, 450

Elemental Analysis:

| | |
|---|---|
| Found | C: 55.85, H: 4.52, N: 4.60 |
| Theoretical | C: 56.13, H: 4.55, N: 4.51 |

Example 11

Synthesis of Au(IPr)(4Meo-PE)[(4-methoxyphenylethynyl)[1,3-bis(2,6-diisopropylphenyl)imidazol-2-ylidene]gold]

Under an argon atmosphere, 1,3-bis(2,6-diisopropylphenyl)imidazolium chloride (IPrH$^+$Cl$^-$; 0.170 g, 0.40 mmol), potassium tert-butoxide (85 mass % article, 69 mg, 0.52 mmol) and tetrahydrofuran (6.2 ml) were added to a 25 ml Schlenk tube, and the mixture was stirred at room temperature for 20 minutes. After tetrahydrofuran was distilled off under reduced pressure, toluene (6.2 ml) was added thereto and the mixture was stirred at 70° C. for 5 minutes. The reaction mixture was filtered and the filtrate was added dropwise to the other 25 ml Schlenk tube added with 4-methoxyphenylethynyl(triphenylphosphine)gold (183 mg, 0.31 mmol) and 6.2 ml of toluene. After completion of the dropwise addition, the reaction mixture was heated at 70° C. for 2.5 hours. The reaction mixture was cooled to room temperature, and then toluene was distilled off under reduced pressure. The resulting white solid was recrystallized in a n-hexane-diethyl ether-methylene chloride system to give 0.180 g of the desired compound as a white solid (yield: 81%).

$^1$H-NMR (300 MHz, CDCl$_3$) δ: 7.49 (dd, 2H), 7.30-7.22 (m, 6H), 7.11 (s, 2H), 6.67-6.62 (m, 2H), 3.71 (s, 3H), 2.61 (sept, 4H), 1.38 (d, 12H), 1.21 (d, 12H)

FAB-MS (M/Z): 716 (M+H)$^+$

Luminescence analysis: (CHCl$_3$, 77K, Ex250 nm) λ (nm): 420 (max), 440

Elemental Analysis:

| | |
|---|---|
| Found | C: 59.98, H: 6.01, N: 3.87 |
| Theoretical | C: 60.33, H: 6.05, N: 3.91 |

Example 12

Synthesis of Au(IMes)(4Meo-PE)[(4-methoxyphenylethynyl)[1,3-bis(2,4,6-trimethylphenyl)imidazol-2-ylidene]gold]

Under an argon atmosphere, 1,3-bis(2,4,6-trimethylphenyl)imidazolium chloride (IMesH$^+$Cl$^-$; 0.155 g, 0.455 mmol), potassium tert-butoxide (85 mass % article, 78.0 mg, 0.59 mmol) and tetrahydrofuran (7.0 ml) were added to a 25 ml Schlenk tube, and the mixture was stirred at room temperature for 20 minutes. After tetrahydrofuran was distilled off under reduced pressure, toluene (7.0 ml) was added thereto and the mixture was stirred at 70° C. for 5 minutes. The reaction mixture was filtered and the filtrate was added dropwise to the other 50 ml Schlenk tube added with 4-methoxyphenylethynyl(triphenylphosphine)gold (207 mg, 0.35 mmol) and 7.0 ml of toluene. After completion of the dropwise addition, the reaction mixture was heated at 70° C. for 2.5 hours. The reaction mixture was cooled to room temperature, and then toluene was distilled off under reduced pressure. The resulting white solid was recrystallized in a n-hexane-diethyl ether-methylene chloride system to give 0.189 g of the desired compound as a white solid (yield: 85%).

$^1$H-NMR (300 MHz, CDCl$_3$) δ: 7.31-7.25 (m, 2H), 7.05 (s, 2H), 6.99 (s, 4H), 6.69-6.64 (m, 2H), 3.72 (s, 3H), 2.34 (s, 0.6H), 2.12 (s, 12H)

FAB-MS (M/Z): 633 (M+H)$^+$

Luminescence analysis: (CHCl$_3$, 77K, Ex240 nm) λ (nm): 419 (max), 440, 459

Elemental Analysis:

| | |
|---|---|
| Found | C: 55.75, H: 4.92, N: 4.29 |
| Theoretical | C: 56.96, H: 4.94, N: 4.43 |

Example 13

Synthesis of Au(IPr)(5F-8QE)[(5-fluoro-8-quinolylethynyl)[1,3-bis(2,6-diisopropylphenyl)imidazol-2-ylidene]gold]

Under an argon atmosphere, 1,3-bis(2,6-diisopropylphenyl)imidazolium chloride (IPrH$^+$Cl$^-$; 0.166 g, 0.39 mmol), potassium tert-butoxide (85 mass % article, 67 mg, 0.51 mmol) and tetrahydrofuran (6.0 ml) were added to a 25 ml Schlenk tube, and the mixture was stirred at room temperature for 20 minutes. After tetrahydrofuran was distilled off under reduced pressure, toluene (6.0 ml) was added thereto and the mixture was stirred at 70° C. for 5 minutes. The reaction mixture was filtered and the filtrate was added dropwise to the other 25 ml Schlenk tube added with 5-fluoro-8-quinolylethynyl(triphenylphosphine)gold (189 mg, 0.300 mmol) and 6.0 ml of toluene. After completion of the dropwise addition, the reaction mixture was heated at 70° C. for 2.5 hours. The reaction mixture was cooled to room temperature, and then toluene was distilled off under reduced pressure. The resulting residue was extracted with ether (20 ml) and the insolubles were filtered off. The ether extract was concentrated and recrystallized in a n-hexane-diethyl ether system to give 0.21 g of the desired compound as a white solid (yield: 87%).

$^1$H-NMR (300 MHz, CDCl$_3$) δ: 8.96 (dd, 1H), 8.29 (dd, 1H), 7.71 (dd, 1H), 7.50 (dd, 2H), 7.35-7.29 (m, 5H), 7.12 (s, 2H), 7.12-6.96 (m, 1H), 2.64 (sept, 4H), 1.40 (d, 12H), 1.22 (d, 12H)

FAB-MS (M/Z): 756 (M+H)$^+$

Luminescence analysis: (CHCl$_3$, 77K, Ex250 nm) λ (nm): 404 (max), 543

Elemental Analysis:

| Found | C: 60.77, H: 5.78, N: 5.34 |
|---|---|
| Theoretical | C: 60.39, H: 5.47, N: 5.56 |

Example 14

Synthesis of Au(IMes)(5F-8QE)[(5-fluoro-8-quinolylethynyl)[1,3-bis(2,4,6-trimethylphenyl)imidazol-2-ylidene]gold]

Under an argon atmosphere, 1,3-bis(2,4,6-trimethylphenyl)imidazolium chloride (IMesH$^+$Cl$^-$; 0.17 g, 0.49 mmol), potassium tert-butoxide (85 mass % article, 84 mg, 0.64 mmol) and tetrahydrofuran (7.5 ml) were added to a 25 ml Schlenk tube, and the mixture was stirred at room temperature for 20 minutes. After tetrahydrofuran was distilled off under reduced pressure, toluene (7.5 ml) was added thereto and the mixture was stirred at 70° C. for 5 minutes. The reaction mixture was filtered and the filtrate was added dropwise to the other 50 ml Schlenk tube added with 5-fluoro-8-quinolylethynyl(triphenylphosphine)gold (229 mg, 0.375 mmol) and 7.5 ml of toluene. After completion of the dropwise addition, the reaction mixture was heated at 70° C. for 8 hours. The reaction mixture was filtered under heating, toluene was distilled off under reduced pressure, and then the resulting solid was recrystallized in a n-hexane-diethyl ether-methylene chloride system to give 0.20 g of the desired compound as a white solid (yield: 78%).

$^1$H-NMR (300 MHz, CDCl$_3$) δ: 8.99 (dd, 1H), 8.31 (dd, 1H), 7.73 (dd, 1H), 7.06 (s, 2H), 7.06-6.98 (m, 1H), 6.98 (s, 4H); 2.34 (s, 6H), 2.13 (s, 12H)

FAB-MS (M/Z): 672 (M+H)$^+$

Luminescence analysis: (CHCl$_3$, 77K, Ex250 nm) λ (nm): 401 (max), 541

Elemental Analysis:

| Found | C: 57.13, H: 4.25, N: 6.16 |
|---|---|
| Theoretical | C: 57.23, H: 4.35, N: 6.23 |

Example 15

Synthesis of Au(IAd)(5F-8QE)[(5-fluoro-8-quinolylethynyl)[1,3-diadamantylimidazol-2-ylidene]gold]

Under an argon atmosphere, 1,3-diadamantylimidazolium chloride (IAdH$^+$Cl$^-$; 0.194 g, 0.52 mmol), potassium tert-butoxide (85 mass % article, 89 mg, 0.68 mmol) and tetrahydrofuran (8.0 ml) were added to a 25 ml Schlenk tube, and the mixture was stirred at room temperature for 20 minutes. After tetrahydrofuran was distilled off under reduced pressure, toluene (8 ml) was added thereto and the mixture was stirred at 70° C. for 5 minutes. The reaction mixture was filtered and the filtrate was added dropwise to the other 50 ml Schlenk tube added with 5-fluoro-8-quinolylethynyl(triphenylphosphine)gold (252 mg, 0.40 mmol) and 8 ml of toluene. After completion of the dropwise addition, the reaction mixture was heated at 70° C. for 3 hours. The reaction mixture was cooled to room temperature, and then toluene was distilled off under reduced pressure. The resulting white solid was recrystallized in a n-hexane-diethyl ether-methylene chloride system to give 0.21 g of the desired compound as a white solid (yield: 73%).

$^1$H-NMR (300 MHz, CDCl$_3$) δ: 9.09 (dd, 1H), 8.37 (dd, 1H), 7.91 (dd, 1H), 7.42 (dd, 1H), 7.22-7.08 (m, 1H), 7.08 (s, 2H), 2.60-2.59 (m, 12H), 2.29 (m, 6H), 1.86-1.72 (m, 12H)

FAB-MS (M/Z): 704 (M+H)$^+$

Luminescence analysis: (CHCl$_3$, 77K, Ex250 nm) λ (nm): 401 (max), 544

Elemental Analysis:

| Found | C: 58.10, H: 5.22, N: 6.00 |
|---|---|
| Theoretical | C: 58.04, H: 5.30, N: 5.97 |

Example 16

Synthesis of Au(ItBu)(5F-8QE)[(5-fluoro-8-quinolylethynyl)[1,3-di-tert-butylimidazol-2-ylidene]gold]

Under an argon atmosphere, 1,3-di-tert-butylimidazolium chloride (ItBuH$^+$Cl$^-$; 0.113 g, 0.52 mmol), potassium tert-butoxide (85 mass % article, 90 mg, 0.68 mmol) and tetrahydrofuran (6.5 ml) were added to a 25 ml Schlenk tube, and the mixture was stirred at room temperature for 20 minutes. After tetrahydrofuran was distilled off under reduced pressure, toluene (8 ml) was added thereto and the mixture was stirred at 70° C. for 5 minutes. The reaction mixture was filtered and the filtrate was added dropwise to the other 50 ml Schlenk tube added with 5-fluoro-8-quinolylethynyl(triphenylphosphine)gold (252 mg, 0.40 mmol) and 8 ml of toluene. After completion of the dropwise addition, the reaction mixture was heated at 70° C. for 2.5 hours. The reaction mixture was cooled to room temperature, and then toluene was distilled off under reduced pressure. The resulting white solid was recrystallized in a n-hexane-methylene chloride system to give 0.15 g of the desired compound as a white solid (yield: 70%).

$^1$H-NMR (300 MHz, CDCl$_3$) δ: 9.09 (dd, 1H), 8.38 (dd, 1H), 7.92 (dd, 1H), 7.42 (dd, 1H), 7.11 (dd, 1H), 7.06 (s, 2H), 1.90 (s, 18H)

FAB-MS (M/Z): 548 (M+H)$^+$

Luminescence analysis: (CHCl$_3$, 77K, Ex240 nm) % (nm): 404 (max)

Elemental Analysis:

| Found | C: 48.30, H: 4.53, N: 7.69 |
|---|---|
| Theoretical | C: 48.27, H: 4.60, N: 7.68 |

Example 17

Synthesis of Au(IPr)(5Cl-8QE)[(5-chloro-8-quinolylethynyl)[1,3-bis(2,6-diisopropylphenyl)imidazol-2-ylidene]gold]

Under an argon atmosphere, 1,3-bis(2,6-diisopropylphenyl)imidazolium chloride (IPrH$^+$Cl$^-$; 213 mg, 0.50 mmol), potassium tert-butoxide (85 mass % article, 86 mg, 0.65 mmol) and tetrahydrofuran (7.5 ml) were added to a 15 ml Schlenk tube, and the mixture was stirred at room temperature for 20 minutes. After tetrahydrofuran was distilled off under reduced pressure, toluene (7.5 ml) was added thereto and the mixture was stirred at 70° C. for 5 minutes. The reaction mixture was filtered and the filtrate was added dropwise to the other 20 ml Schlenk tube added with 5-chloro-8-quinolylethynyl(triphenylphosphine)gold (249 mg, 0.385 mmol) and 7.5 ml of toluene. After completion of the dropwise addition, the reaction mixture was heated at 70° C. for 2.5 hours. The reaction mixture was cooled to room temperature, and then toluene was distilled off under reduced pressure. The resulting residue was extracted with ether (20 ml) and the insolubles were filtered off. The ether extract was concentrated and recrystallized in a n-hexane-diethyl ether system to give 0.27 g of the desired compound as a light red brown solid (yield: 91%).

$^1$H-NMR (300 MHz, CDCl$_3$) δ: 8.96 (dd, 1H), 8.45 (dd, 1H), 7.69 (d, 1H), 7.50 (dd, 2H), 7.40 (dd, 2H), 7.35-7.29 (m, 5H), 7.12 (s, 2H), 2.64 (sept, 4H), 1.40 (d, 12H), 1.22 (d, 12H)

FAB-MS (M/Z): 773 (M+H)$^+$

Luminescence analysis: (CHCl$_3$, 77K, Ex250 nm) λ (nm): 406 (max)

Elemental Analysis:

| Found | C: 59.98, H: 5.50, N: 5.39 |
|---|---|
| Theoretical | C: 60.11, H: 5.35, N: 5.44 |

Example 18

Synthesis of Au(IMes)(5Cl-8QE)[(5-chloro-8-quinolylethynyl)[1,3-bis(2,4,6-trimethylphenyl)imidazol-2-ylidene]gold]

Under an argon atmosphere, 1,3-bis(2,4,6-trimethylylphenyl)imidazolium chloride (IMesH$^+$Cl$^-$; 171 mg, 0.50 mmol), potassium tert-butoxide (85 mass % article, 86 mg, 0.65 mmol) and tetrahydrofuran (7.5 ml) were added to a 15 ml Schlenk tube, and the mixture was stirred at room temperature for 20 minutes. After tetrahydrofuran was distilled off under reduced pressure, toluene (7.5 ml) was added thereto and the mixture was stirred at 70° C. for 5 minutes. The reaction mixture was filtered and the filtrate was added dropwise to the other 20 ml Schlenk tube added with 5-chloro-8-quinolylethynyl(triphenylphosphine)gold (249 mg, 0.385 mmol) and 7.5 ml of toluene. After completion of the dropwise addition, the reaction mixture was heated at 70° C. for 7 hours. The reaction mixture was filtered at heating and then toluene was distilled off under reduced pressure. The resulting solid was recrystallized in an ethyl alcohol-diethyl ether system to give 0.14 g of the desired compound as a light pink solid (yield: 53%).

$^1$H-NMR (300 MHz, CDCl$_3$) δ: 8.99 (dd, 1H), 8.46 (dd, 1H), 7.70 (d, 1H), 7.41 (dd, 3H), 7.06 (s, 2H), 6.98 (s, 4H), 2.34 (s, 6H), 2.13 (s, 12H)

FAB-MS (M/Z): 688 (M+H)$^+$

Luminescence analysis: (CHCl$_3$, 77K, Ex250 nm) λ (nm): 398 (max), 553

Elemental Analysis:

| Found | C: 55.70, H: 4.36, N: 5.87 |
|---|---|
| Theoretical | C: 55.86, H: 4.25, N: 6.11 |

Example 19

Synthesis of Au(IAd)(5Cl-8QE)[(5-chloro-8-quinolylethynyl)[1,3-diadamantylimidazol-2-ylidene]gold]

Under an argon atmosphere, 1,3-diadamantylimidazolium chloride (IAdH$^+$Cl$^-$; 93 mg, 0.25 mmol), potassium tert-butoxide (85 mass % article, 43 mg, 0.33 mmol) and tetrahydrofuran (3.8 ml) were added to a 15 ml Schlenk tube, and the mixture was stirred at room temperature for 20 minutes. After tetrahydrofuran was distilled off under reduced pressure, toluene (3.8 ml) was added thereto and the mixture was stirred at 70° C. for 5 minutes. The reaction mixture was filtered and the filtrate was added dropwise to the other 20 ml Schlenk tube added with 5-chloro-8-quinolylethynyl(triphenylphosphine)gold (124 mg, 0.19 mmol) and 3.8 ml of toluene. After completion of the dropwise addition, the reaction mixture was heated at 70° C. for 2.5 hours. The reaction mixture was cooled to room temperature, and then toluene was distilled off under reduced pressure. The resulting solid was recrystallized in a n-hexane-diethyl ether-methylene chloride system to give 0.12 g of the desired compound as a flesh-colored solid (yield: 85%).

$^1$H-NMR (300 MHz, CDCl$_3$) δ: 9.09 (dd, 1H), 8.52 (dd, 1H), 7.90 (d, 1H), 7.51-7.26 (m, 2H), 6.91 (s, 2H), 2.60-2.59 (m, 12H), 2.29 (m, 6H), 1.86-1.72 (m, 12H)

FAB-MS (M/Z): 720 (M+H)$^+$

Luminescence analysis: (CHCl$_3$, 77K, Ex250 nm) λ (nm): 401 (max), 554

Elemental Analysis:

| Found | C: 57.39, H: 5.26, N: 5.78 |
|---|---|
| Theoretical | C: 56.71, H: 5.18, N: 5.84 |

Example 20

Synthesis of Au(ItBu)(5Cl-8QE)[(5-chloro-8-quinolylethynyl)[1,3-di-tert-butylimidazol-2-ylidene]gold]

Under an argon atmosphere, 1,3-di-tert-butylimidazolium chloride (ItBuH$^+$Cl$^-$; 54 mg, 0.25 mmol), potassium tert-butoxide (85 mass % article, 43 mg, 0.33 mmol) and tetrahydrofuran (3.8 ml) were added to a 15 ml Schlenk tube, and the mixture was stirred at room temperature for 20 minutes. After tetrahydrofuran was distilled off under reduced pressure, toluene (3.8 ml) was added thereto and the mixture was stirred at 70° C. for 5 minutes. The reaction mixture was filtered and the filtrate was added dropwise to the other 20 ml Schlenk tube added with 5-chloro-8-quinolylethynyl(triphenylphosphine)gold (124 mg, 0.19 mmol) and 3.8 ml of toluene. After completion of the dropwise addition, the reaction mixture was heated at 70° C. for 2.5 hours. The reaction mixture was cooled to room temperature, and then toluene was distilled off under reduced pressure. The resulting solid was recrystallized in a n-hexane-methylene chloride system to give 0.10 g of the desired compound as a flesh-colored solid (yield: 93%).

$^1$H-NMR (300 MHz, CDCl$_3$) δ: 9.09 (dd, 1H), 8.55 (dd, 1H), 7.90 (d, 1H), 7.52-7.40 (m, 3H), 7.06 (s, 2H), 1.90 (s, 18H)

FAB-MS (M/Z): 564 (M+H)$^+$

Luminescence analysis: (CHCl$_3$, 77K, Ex240 nm) λ (nm): 401 (max), 554

Elemental Analysis:

| | |
|---|---|
| Found | C: 47.59, H: 4.61, N: 7.32 |
| Theoretical | C: 46.86, H: 4.47, N: 7.45 |

Example 21

Synthesis of Au(Cl$_2$—IPr) (5F-8QE) [(5-fluoro-8-quinolylethynyl)[1,3-bis(2,6-diisopropylphenyl)-4,5-dichloroimidazol-2-ylidene]gold]

Under an argon atmosphere, 1,3-bis(2,6-diisopropylphenyl)imidazolium chloride (IPrH$^+$Cl$^-$; 327 mg, 0.77 mmol), potassium tert-butoxide (85 mass % article, 132 mg, 1.0 mmol) and tetrahydrofuran (7.0 ml) were added to a 15 ml Schlenk tube, and the mixture was stirred at room temperature for 20 minutes. Thereafter, carbon tetrachloride (148 μl, 1.54 mmol) was added to the reaction mixture and the mixture was stirred at room temperature for 30 minutes. After tetrahydrofuran was distilled off under reduced pressure, toluene (7.0 ml) was added thereto and the mixture was stirred at 70° C. for 5 minutes. The reaction mixture was filtered and the filtrate was added dropwise to the other 25 ml Schlenk tube added with 5-fluoro-8-quinolylethynyl(triphenylphosphine)gold (242 mg, 0.385 mmol) and 7.0 ml of toluene. After completion of the dropwise addition, the reaction mixture was heated at 70° C. for 3 hours. The reaction mixture was cooled to room temperature, and then toluene was distilled off under reduced pressure. The resulting residue was washed with ether to give 0.27 g of the desired compound as a white solid (yield: 85%).

$^1$H-NMR (300 MHz, CDCl$_3$) δ: 8.95 (dd, 1H), 8.29 (dd, 1H), 7.69 (dd, 1H), 7.61-7.53 (m, 2H), 7.39-7.30 (m, 5H), 6.99 (dd, 1H), 2.56-2.45 (sept, 4H), 1.39 (d, 12H), 1.25 (d, 12H)

FAB-MS (M/Z): 724 (M+H)$^+$

Luminescence analysis: (CHCl$_3$, 77K, Ex250 nm) λ (nm): 391 (max), 396, 404

Elemental Analysis:

| | |
|---|---|
| Found | C: 55.74, H: 4.66, N: 5.11 |
| Theoretical | C: 55.35, H: 4.77, N: 5.10 |

Example 22

Synthesis of Au(C$_{12}$-IMes) (5F-8QE) [(5-fluoro-8-quinolylethynyl)[1,3-bis(2,4,6-trimethylphenyl)-4,5-dichloroimidazol-2-ylidene]gold]

Under an argon atmosphere, 1,3-bis(2,4,6-trimethylphenyl)imidazolium chloride (IMesH$^+$Cl$^-$; 262.5 mg, 0.77 mmol), potassium tert-butoxide (85 mass % article, 132 mg, 1.0 mmol) and tetrahydrofuran (7.0 ml) were added to a 15 ml Schlenk tube, and the mixture was stirred at room temperature for 20 minutes. Thereafter, carbon tetrachloride (148 μl, 1.54 mmol) was added to the reaction mixture and the mixture was stirred at room temperature for 30 minutes. After tetrahydrofuran was distilled off under reduced pressure, toluene (7.0 ml) was added thereto and the mixture was stirred at 70° C. for 5 minutes. The reaction mixture was filtered and the filtrate was added dropwise to the other 25 ml Schlenk tube added with 5-fluoro-8-quinolylethynyl(triphenylphosphine)gold (242 mg, 0.385 mmol) and 7.0 ml of toluene. After completion of the dropwise addition, the reaction mixture was heated at 70° C. for 3 hours. The reaction mixture was cooled to room temperature, and then toluene was distilled off under reduced pressure. The resulting residue was dissolved in 20 ml of methylene chloride and washed with water. The organic layer was dried over sodium sulfate, and then methylene chloride was distilled off under reduced pressure. The resulting residue was recrystallized in an ethyl acetate-hexane system and the precipitate was dried under reduced pressure to give 0.20 g of the desired compound as a light brown solid (yield: 69%).

$^1$H-NMR (300 MHz, CDCl$_3$) δ: 8.98 (dd, 1H), 8.32 (dd, 1H), 7.72 (dd, 1H), 7.36 (dd, 1H), 7.07-6.91 (m, 5H), 2.33 (s, 6H), 2.12 (s, 12H)

FAB-MS (M/Z): 740 (M+H)$^+$

Luminescence analysis: (CHCl$_3$, 77K, Ex250 nm) λ (nm): 398 (max), 538

Elemental Analysis:

| | |
|---|---|
| Found | C: 52.39, H: 3.72, N: 5.62 |
| Theoretical | C: 51.91, H: 3.68, N: 5.67 |

Example 23

Synthesis of Au(Cl$_2$—IPr) (5Cl-8QE) [(5-chloro-8-quinolylethynyl)[1,3-bis(2,6-diisopropylphenyl)-4,5-dichloroimidazol-2-ylidene]gold]

Under an argon atmosphere, 1,3-bis(2,6-diisopropylphenyl)imidazolium chloride (IPrH$^+$Cl$^-$; 340 mg, 0.80 mmol), potassium tert-butoxide (85 mass % article, 137 mg, 1.04 mmol) and tetrahydrofuran (8.0 ml) were added to a 15 ml Schlenk tube, and the mixture was stirred at room temperature for 20 minutes. Thereafter, carbon tetrachloride (153 μl, 1.60 mmol) was added to the reaction mixture and the mixture was stirred at room temperature for 30 minutes. After tetrahydrofuran was distilled off under reduced pressure, toluene (8.0 ml) was added thereto and the mixture was stirred at 70° C. for 5 minutes. The reaction mixture was filtered and the filtrate was added dropwise to the other 25 ml Schlenk tube added with 5-chloro-8-quinolylethynyl(triphenylphosphine)gold (259 mg, 0.40 mmol) and 8.0 ml of toluene. After completion of the dropwise addition, the reaction mixture was heated at 70° C. for 3 hours. The reaction mixture was cooled to room temperature, and then 30 ml of toluene was added thereto and the mixture was washed with water and pH is made to 7. The organic layer was dried over sodium sulfate and toluene was distilled off under reduced pressure. The resulting was recrystallized in a diethyl ether-hexane system and the precipitate was dried under reduced pressure to give 0.21 g of the desired compound as a pale flesh-colored solid (yield: 63%).

$^1$H-NMR (300 MHz, CDCl$_3$) δ: 8.94 (dd, 1H), 8.46 (dd, 1H), 7.69 (dd, 1H), 7.61-7.39 (m, 2H), 7.37-7.29 (m, 6H), 2.56-2.45 (sept, 4H), 1.39 (d, 12H), 1.25 (d, 12H)

FAB-MS (M/Z): 842 (M+H)$^+$

Luminescence analysis: (CHCl$_3$, 77K, Ex250 nm) λ (nm): 394 (max), 558

Elemental Analysis:

| Found | C: 54.80, H: 4.74, N: 4.91 |
|---|---|
| Theoretical | C: 54.27, H: 4.67, N: 5.00 |

Example 24

Synthesis of Au(Cl$_2$—IMes) (5Cl-8QE) [(5-chloro-8-quinolylethynyl)[1,3-bis(2,4,6-trimethylphenyl)-4,5-dichloroimidazol-2-ylidene]gold]

Under an argon atmosphere, 1,3-bis(2,4,6-trimethylphenyl)imidazolium chloride (IMesH$^+$Cl$^-$; 262.5 mg, 0.77 mmol), potassium tert-butoxide (85 mass % article, 132 mg, 1.0 mmol) and tetrahydrofuran (7.0 ml) were added to a 15 ml Schlenk tube, and the mixture was stirred at room temperature for 20 minutes. Thereafter, carbon tetrachloride (148 μl, 1.54 mmol) was added to the reaction mixture and the mixture was stirred at room temperature for 30 minutes. After tetrahydrofuran was distilled off under reduced pressure, toluene (7.0 ml) was added thereto and the mixture was stirred at 70° C. for 5 minutes. The reaction mixture was filtered and the filtrate was added dropwise to the other 25 ml Schlenk tube added with 5-chloro-8-quinolylethynyl(triphenylphosphine)gold (249 mg, 0.385 mmol) and 7.0 ml of toluene. After completion of the dropwise addition, the reaction mixture was heated at 70° C. for 3 hours. The reaction mixture was cooled to room temperature, and then 30 ml of toluene was added thereto, the mixture was washed with water and pH is made to 7. The organic layer was dried over sodium sulfate and toluene was distilled off under reduced pressure. The resulting residue was recrystallized in an ethyl acetate-hexane system and the precipitate was dried under reduced pressure to give 0.19 g of the desired compound as a pale brown solid (yield: 65%).

$^1$H-NMR (300 MHz, CDCl$_3$) δ: 8.98 (dd, 1H), 8.47 (dd, 1H), 7.70 (dd, 1H), 7.42 (dd, 2H), 7.02 (s, 4H), 2.33 (s, 6H), 2.12 (s, 12H)

FAB-MS (M/Z): 756 (M+H)$^+$

Luminescence analysis: (CHCl$_3$, 77K, Ex250 nm) λ (nm): 381, 397 (max)

Elemental Analysis:

| Found | C: 53.05, H: 4.13, N: 5.53 |
|---|---|
| Theoretical | C: 52.78, H: 4.00, N: 5.55 |

Example 25

Synthesis of Au(H$_2$—IPr) (5F-8QE) [(5-fluoro-8-quinolylethynyl)[1,3-bis(2,6-diisopropylphenyl)-4,5-dihydroimidazol-2-ylidene]gold]

Under an argon atmosphere, 1,3-bis(2,6-diisopropylphenyl)imidazolinium chloride (H$_2$IPrH$^+$Cl$^-$; 278 mg, 0.65 mmol), potassium tert-butoxide (85 mass % article, 112 mg, 0.85 mmol) and tetrahydrofuran (10.0 ml) were added to a 15 ml Schlenk tube, the mixture was stirred at room temperature for 20 minutes, and then tetrahydrofuran was distilled off under reduced pressure. Toluene (10.0 ml) was added thereto and the mixture was stirred at 70° C. for 5 minutes, and then the reaction mixture was filtered and the filtrate was added dropwise to the other 25 ml Schlenk tube added with 5-fluoro-8-quinolylethynyl(triphenylphosphine)gold (315 mg, 0.50 mmol) and 10.0 ml of toluene. After completion of the dropwise addition, the reaction mixture was heated at 70° C. for 3 hours. The reaction mixture was cooled to room temperature, and then 30 ml of toluene was added thereto, the mixture was washed with water and pH is made to 7. The organic layer was dried over sodium sulfate and toluene was distilled off under reduced pressure. The resulting residue was recrystallized in an ethyl acetate-hexane system and the precipitate was dried under reduced pressure to give 0.31 g of the desired compound as a white solid (yield: 81%).

$^1$H-NMR (300 MHz, CDCl$_3$) δ: 8.92 (dd, 1H), 8.27 (dd, 1H), 7.66 (dd, 1H), 7.42 (dd, 2H), 7.34-7.21 (m, 5H), 6.97 (dd, 1H), 3.99 (s, 4H), 3.16-3.06 (m, 4H), 1.48 (d, 12H), 1.34 (d, 12H)

FAB-MS (M/Z): 758 (M+H)$^+$

Luminescence analysis: (CHCl$_3$, 77K, Ex250 nm) λ (nm): 402 (max), 544

Elemental Analysis:

| Found | C: 60.23, H: 5.72, N: 5.55 |
|---|---|
| Theoretical | C: 60.09, H: 5.58, N: 5.48 |

Example 26

Synthesis of Au(H$_2$—IPr) (5Cl-8QE) [(5-chloro-8-quinolylethynyl)[1,3-bis(2,6-diisopropylphenyl)-4,5-dihydroimidazol-2-ylidene]gold]

Under an argon atmosphere, 1,3-bis(2,6-diisopropylphenyl)imidazolinium chloride (H$_2$IPrH$^+$Cl$^-$; 255 mg, 0.60 mmol), potassium tert-butoxide (85 mass % article, 103 mg, 0.78 mmol) and tetrahydrofuran (9.0 ml) were added to a 15 ml Schlenk tube, the mixture was stirred at room temperature for 20 minutes, and then tetrahydrofuran was distilled off under reduced pressure. Toluene (9.0 ml) was added thereto and the mixture was stirred at 70° C. for 5 minutes, and then the reaction mixture was filtered and the filtrate was added dropwise to the other 25 ml Schlenk tube added with 5-chloro-8-quinolylethynyl(triphenylphosphine)gold (300 mg, 0.46 mmol) and 9.0 ml of toluene. After completion of the dropwise addition, the reaction mixture was heated at 70° C. for 3 hours. The reaction mixture was cooled to room temperature, and then 30 ml of toluene was added thereto, the mixture was washed with water and pH is made to 7. The organic layer was dried over sodium sulfate and toluene was distilled off under reduced pressure. The resulting residue was recrystallized in an ethyl acetate-hexane system and the precipitate was dried under reduced pressure to give 0.23 g of the desired compound as a pale flesh-colored solid (yield: 66%).

$^1$H-NMR (300 MHz, CDCl$_3$) δ: 8.93 (dd, 1H), 8.43 (dd, 1H), 7.64 (d, 1H), 4.00 (s, 4H), 3.16-3.07 (m, 4H), 1.48 (d, 12H), 1.34 (d, 12H)

FAB-MS (M/Z): 774 (M+H)$^+$

Luminescence analysis: (CHCl$_3$, 77K, Ex250 nm) λ (nm): 402 (max), 555

Elemental Analysis:

| | |
|---|---|
| Found | C: 58.95, H: 6.60, N: 5.43 |
| Theoretical | C: 59.13, H: 6.54, N: 5.41 |

Example 27

Synthesis of Au(IPr)(2PyE)[(2-pyridylethynyl)[1,3-bis(2,6-diisopropylphenyl)imidazol-2-ylidene]gold]

Under an argon atmosphere, 1,3-bis(2,6-diisopropylphenyl)imidazolium chloride (IPrH$^+$Cl$^-$; 175 mg, 0.41 mmol), potassium tert-butoxide (85 mass % article, 71 mg, 0.53 mmol) and tetrahydrofuran (6.5 ml) were added to a 20 ml Schlenk tube, the mixture was stirred at room temperature for 20 minutes, and then tetrahydrofuran was distilled off under reduced pressure. Toluene (6.5 ml) was added thereto and the mixture was stirred at 70° C. for 5 minutes, and then the reaction mixture was filtered and the filtrate was added dropwise to the other 20 ml Schlenk tube added with 2-pyridylethynyl(triphenylphosphine)gold (178 mg, 0.32 mmol) and 6.5 ml of toluene. After completion of the dropwise addition, the reaction mixture was heated at 70° C. for 3 hours. The reaction mixture was cooled to room temperature, and then the reaction mixture was filtered and concentrated. The resulting solid was dissolved in ethyl acetate and reprecipitated with hexane. The resulting precipitate was filtered to give 0.18 g of the desired compound as a white solid (yield: 83%).

$^1$H-NMR (300 MHz, CDCl$_3$) δ: 8.38-8.36 (m, 1H), 7.52-7.37 (m, 3H), 7.30-7.20 (m, 5H), 7.12 (s, 2H), 6.96-6.91 (m, 1H), 2.63-2.54 (sept, 4H), 1.37 (d, 12H), 1.21 (d, 12H)

(FAB-MS) (M/Z): 688 (M+H)$^+$

Luminescence analysis: (CHCl$_3$, 77K, Ex250 nm) λ (nm): 417, 445, 457

Elemental Analysis:

| | |
|---|---|
| Found | C: 59.32, H: 5.82, N: 6.05 |
| Theoretical | C: 59.38, H: 5.86, N: 6.11 |

Example 28

Synthesis of Au(IPr)(3PyE)[(3-pyridylethynyl)[1,3-bis(2,6-diisopropylphenyl)imidazol-2-ylidene]gold]

Under an argon atmosphere, 1,3-bis(2,6-diisopropylphenyl)imidazolium chloride (IPrH$^+$Cl$^-$; 195 mg, 0.46 mmol), potassium tert-butoxide (85 mass % article, 79 mg, 0.60 mmol) and tetrahydrofuran (7.3 ml) were added to a 25 ml Schlenk tube, the mixture was stirred at room temperature for 20 minutes, and then tetrahydrofuran was distilled off under reduced pressure. Toluene (7.3 ml) was added thereto and the mixture was stirred at 70° C. for 5 minutes, and then the reaction mixture was filtered and the filtrate was added dropwise to the other 20 ml Schlenk tube added with 3-pyridylethynyl(triphenylphosphine)gold (198 mg, 0.35 mmol) and 7.3 ml of toluene. After completion of the dropwise addition, the reaction mixture was heated at 70° C. for 3 hours. The reaction mixture was cooled to room temperature, and then the reaction mixture was filtered and concentrated. The resulting solid was dissolved in methylene chloride and reprecipitated with hexane. The resulting precipitate was filtered to give 0.22 g of the desired compound as a white solid (yield: 91%).

$^1$H-NMR (300 MHz, CDCl$_3$) δ: 8.52-8.51 (m, 1H), 8.27-8.25 (m, 1H), 7.58-7.48 (m, 3H), 7.31-7.27 (m, 4H), 7.14 (s, 2H), 7.04-7.00 (m, 1H), 2.65-2.56 (sept, 4H), 1.38 (d, 12H), 1.22 (d, 12H)

(FAB-MS) (M/Z): 688 (M+H)$^+$

Luminescence analysis: (CHCl$_3$, 77K, Ex250 nm) λ (nm): 443, 450, 462

Elemental Analysis:

| | |
|---|---|
| Found | C: 59.44, H: 5.82, N: 6.16 |
| Theoretical | C: 59.38, H: 5.86, N: 6.11 |

Example 29

Synthesis of Au(IPr)(5F-2PyE)[(5-fluoro-2-pyridylethynyl)[1,3-bis(2,6-diisopropylphenyl)imidazol-2-ylidene]gold]

Under an argon atmosphere, 1,3-bis(2,6-diisopropylphenyl)imidazolium chloride (IPrH$^+$Cl$^-$; 276 mg, 0.65 mmol), potassium tert-butoxide (85 mass % article, 112 mg, 0.845 mmol) and tetrahydrofuran (10 ml) were added to a 20 ml Schlenk tube, the mixture was stirred at room temperature for 20 minutes, and then tetrahydrofuran was distilled off under reduced pressure. Toluene (10 ml) was added thereto and the mixture was stirred at 70° C. for 5 minutes, and then the reaction mixture was filtered and the filtrate was added dropwise to the other 30 ml Schlenk tube added with 5-fluoro-2-pyridylethynyl(triphenylphosphine)gold (290 mg, 0.5 mmol) and 10 ml of toluene. After completion of the dropwise addition, the reaction mixture was heated at 70° C. for 3 hours. The reaction mixture was cooled to room temperature, and then toluene was added to the reaction mixture and the mixture was washed with water to make pH to 7. The mixture was dried over sodium sulfate, and then the solvent was distilled off under reduced pressure by an evaporator. The crude reaction product was purified by column chromatography (hexane/AcOEt=3/1) using silica gel and the resulting solid was dissolved in ethyl acetate and reprecipitated with hexane. The resulting precipitate was filtered to give 0.31 g of the desired compound as a yellow solid (yield: 89%).

$^1$H-NMR (300 MHz, CDCl$_3$) δ: 8.22 (d, 1H), 7.49 (t, 2H), 7.19-7.29 (m, 6H), 7.12 (s, 2H), 2.54-2.63 (sept, 4H), 1.36 (d, 12H), 1.22 (d, 12H)

(FAB-MS) (M/Z): 706 (M+H)$^+$

Luminescence analysis: (CHCl$_3$, 77K, Ex250 nm) λ (nm): 419, 436, 448, 460

Elemental Analysis:

| | |
|---|---|
| Found | C: 57.62, H: 5.30, N: 5.91 |
| Theoretical | C: 57.87, H: 5.57, N: 5.95 |

Example 30

Synthesis of Au(IPr)(6F-3PyE)[(6-fluoro-3-pyridylethynyl)[1,3-bis(2,6-diisopropylphenyl)imidazol-2-ylidene]gold]

Under an argon atmosphere, 1,3-bis(2,6-diisopropylphenyl)imidazolium chloride (IPrH$^+$Cl$^-$; 276 mg, 0.65 mmol), potassium tert-butoxide (85 mass % article, 112 mg, 0.845 mmol) and tetrahydrofuran (10 ml) were added to a 20 ml Schlenk tube, the mixture was stirred at room temperature for 20 minutes, and then tetrahydrofuran was distilled off under reduced pressure. Toluene (10 ml) was added thereto and the mixture was stirred at 70° C. for 5 minutes, and then the reaction mixture was filtered and the filtrate was added dropwise to the other 30 ml Schlenk tube added with 6-fluoro-3-pyridylethynyl(triphenylphosphine)gold (290 mg, 0.5 mmol) and 10 ml of toluene. After completion of the dropwise addition, the reaction mixture was heated at 70° C. for 3 hours. The reaction mixture was cooled to room temperature, and then toluene was added to the reaction mixture and the mixture was washed with water to make pH to 7. The mixture was dried over sodium sulfate, and then the solvent was distilled off under reduced pressure by an evaporator. The crude reaction product was purified by column chromatography (hexane/AcOEt=3/1) using silica gel and the resulting solid was dissolved in ethyl acetate and reprecipitated with hexane. The resulting precipitate was filtered to give 0.32 g of the desired compound as a yellow solid (yield: 90%).

$^1$H-NMR (300 MHz, CDCl$_3$) δ: 8.11 (s, 1H), 7.61-7.67 (m, 1H), 7.48-7.53 (m, 2H), 7.26-7.31 (m, 4H), 7.14 (s, 1H), 6.64-6.68 (m, 1H), 2.55-2.64 (sept, 4H), 1.36 (d, 12H), 1.22 (d, 12H)

(FAB-MS) (M/Z): 706 (M+H)$^+$

Luminescence analysis: (CHCl$_3$, 77K, Ex250 nm) λ (nm): 410, 428, 438, 449

Elemental Analysis:

| Found | C: 57.11, H: 5.48, N: 5.87 |
|---|---|
| Theoretical | C: 57.87, H: 5.57, N: 5.95 |

Example 31

Synthesis of Au(IPr)(4Ph-PE)[(4-phenylphenylethynyl)[1,3-bis(2,6-diisopropylphenyl)imidazol-2-ylidene]gold]

Under an argon atmosphere, 1,3-bis(2,6-diisopropylphenyl)imidazolium chloride (IPrH$^+$Cl$^-$; 194 mg, 0.46 mmol), potassium tert-butoxide (85 mass % article, 78 mg, 0.59 mmol) and tetrahydrofuran (7.2 ml) were added to a 20 ml Schlenk tube, the mixture was stirred at room temperature for 20 minutes, and then tetrahydrofuran was distilled off under reduced pressure. Toluene (7.2 ml) was added thereto and the mixture was stirred at 70° C. for 5 minutes, and then the reaction mixture was filtered and the filtrate was added dropwise to the other 20 ml Schlenk tube added with 4-phenylphenylethynyl(triphenylphosphine)gold (223 mg, 0.35 mmol) and 7.2 ml of toluene. After completion of the dropwise addition, the reaction mixture was heated at 70° C. for 3 hours. The reaction mixture was cooled to room temperature, and then the reaction mixture was filtered and concentrated. The resulting solid was dissolved in methylene chloride and reprecipitated with hexane. The resulting precipitate was filtered to give 0.26 g of the desired compound as a white solid (yield: 97%).

$^1$H-NMR (300 MHz, CDCl$_3$) δ: 7.54-7.47 (m, 1H), 7.39-7.23 (m, 11H), 7.13 (s, 2H), 6.96-6.91 (m, 1H), 2.67-2.57 (sept, 4H), 1.39 (d, 12H), 1.22 (d, 12H)

(FAB-MS) (M/Z): 763 (M+H)$^+$

Luminescence analysis: (CHCl$_3$, 77K, Ex250 nm) λ (nm): 485, 517

Elemental Analysis:

| Found | C: 64.26, H: 5.76, N: 3.62 |
|---|---|
| Theoretical | C: 64.56, H: 5.95, N: 3.67 |

Example 32

Synthesis of Au(IPr) (4NO$_2$—PE) [(4-nitrophenylethynyl) [1,3-bis(2,6-diisopropylphenyl)imidazol-2-ylidene]gold]

Under an argon atmosphere, 1,3-bis(2,6-diisopropylphenyl)imidazolium chloride (IPrH$^+$Cl$^-$; 194 mg, 0.46 mmol), potassium tert-butoxide (85 mass % article, 78 mg, 0.59 mmol) and tetrahydrofuran (7.2 ml) were added to a 20 ml Schlenk tube, the mixture was stirred at room temperature for 20 minutes, and then tetrahydrofuran was distilled off under reduced pressure. Toluene (7.2 ml) was added thereto and the mixture was stirred at 70° C. for 5 minutes, and then the reaction mixture was filtered and the filtrate was added dropwise to the other 20 ml Schlenk tube added with 4-nitrophenylethynyl(triphenylphosphine)gold (212 mg, 0.35 mmol) and 7.2 ml of toluene. After completion of the dropwise addition, the reaction mixture was heated at 70° C. for 3 hours. The reaction mixture was cooled to room temperature, and then the reaction mixture was filtered and concentrated. The resulting solid was dissolved in ethyl acetate and reprecipitated with hexane. The resulting precipitate was filtered to give 0.17 g of the desired compound as a white solid (yield: 67%).

$^1$H-NMR (300 MHz, CDCl$_3$) δ: 7.99-7.96 (m, 2H), 7.53-7.48 (m, 2H), 7.39-7.29 (m, 6H), 7.15 (s, 2H), 6.96-6.91 (m, 1H), 2.62-2.57 (sept, 4H), 1.38 (d, 12H), 1.23 (d, 12H)

(FAB-MS) (M/Z): 730 (M−H)$^+$

Luminescence analysis: (CHCl$_3$, 77K, Ex250 nm) λ (nm): 494, 523

Elemental Analysis:

| Found | C: 64.35, H: 5.46, N: 5.74 |
|---|---|
| Theoretical | C: 57.45, H: 5.51, N: 5.74 |

Example 33

Synthesis of Au(IPr) (2,4F$_2$—PE) [(2,4-difluorophenylethynyl)[1,3-bis(2,6-diisopropylphenyl)imidazol-2-ylidene]gold]

Under an argon atmosphere, 1,3-bis(2,6-diisopropylphenyl)imidazolium chloride (IPrH$^+$Cl$^-$; 194 mg, 0.46 mmol), potassium tert-butoxide (85 mass % article, 78 mg, 0.59 mmol) and tetrahydrofuran (7.2 ml) were added to a 20 ml Schlenk tube, the mixture was stirred at room temperature for 20 minutes, and then tetrahydrofuran was distilled off under reduced pressure. Toluene (7.2 ml) was added thereto and the mixture was stirred at 70° C. for 5 minutes, and then the reaction mixture was filtered and the filtrate was added dropwise to the other 20 ml Schlenk tube added with 2,4-difluorophenylethynyl(triphenylphosphine)gold (209 mg, 0.35 mmol) and 7.2 ml of toluene. After completion of the dropwise addition, the reaction mixture was heated at 70° C. for 3 hours. The reaction mixture was cooled to room temperature, and then the reaction mixture was filtered and concentrated. The resulting solid was dissolved in ethyl acetate and reprecipitated with hexane. The resulting precipitate was filtered to give 0.21 g of the desired compound as a white solid (yield: 84%).

$^1$H-NMR (300 MHz, CDCl$_3$) δ: 7.52-7.47 (m, 2H), 7.34-7.22 (m, 5H), 7.12 (s, 2H), 6.67-6.58 (m, 2H), 2.65-2.56 (sept, 4H), 1.37 (d, 12H), 1.21 (d, 12H)

(FAB-MS) (M/Z): 723 (M+H)$^+$

Luminescence analysis: (CHCl$_3$, 77K, Ex250 nm) λ (nm): 414, 426, 442, 454, 468

Elemental Analysis:

| | |
|---|---|
| Found | C: 57.93, H: 5.25, N: 3.91 |
| Theoretical | C: 58.17, H: 5.44, N: 3.88 |

Example 34

Synthesis of Au(IPr)(1NpE)[(1-naphthylethynyl)[1,3-bis(2,6-diisopropylphenyl)imidazol-2-ylidene]gold]

Under an argon atmosphere, 1,3-bis(2,6-diisopropylphenyl)imidazolium chloride (447 mg, 95 mass % article, 1.00 mmol), potassium tert-butoxide (172 mg, 85 mass % article, 1.30 mmol) and 15.0 ml of tetrahydrofuran were added to a 30 ml Schlenk tube, and the mixture was stirred at room temperature for 20 minutes. Tetrahydrofuran was distilled off under reduced pressure, and then 15.0 ml of toluene was added thereto and the mixture was stirred at 70° C. for 5 minutes. The reaction mixture was filtered and the filtrate was added dropwise to the other 30 ml Schlenk tube added with (1-naphthylethynyl)(triphenylphosphine)gold (470 mg, 0.770 mmol) and 15.0 ml of toluene. After completion of the dropwise addition, the reaction mixture was heated at 70° C. for 1 hour. The reaction mixture was cooled to room temperature, and then the crude reaction product obtained by distilling off toluene under reduced pressure was purified by column chromatography (Hexane/AcOEt=100/0→1/4) using silica gel to give 210 mg of the desired compound as a white solid (yield: 59.1%).

$^1$H-NMR (300 MHz, CDCl$_3$) δ: 8.40-8.37 (m, 1H), 7.71-7.68 (m, 1H), 7.57-7.46 (m, 5H), 7.40-7.30 (m, 6H), 7.16 (s, 2H), 2.65 (sept, 4H), 1.44 (d, 12H), 1.23 (d, 12H)

[MS] EI (m/z): 736 (M$^+$), CI (m/z): 737 (MH$^+$)

Luminescence analysis: (CHCl$_3$, 77K, Ex250 nm) λ (nm): 530

Elemental Analysis:

| | |
|---|---|
| Found | C: 63.40, H: 6.05, N: 3.63 |
| Theoretical | C: 63.58, H: 5.88, N: 3.80 |

Example 35

Synthesis of Au(H$_2$—IPr) (4F-1NpE) [(4-fluoro-1-naphthylethynyl)[1,3-bis(2,6-diisopropylphenyl)-4,5-dihydroimidazol-2-ylidene]gold]

Under an argon atmosphere, 1,3-bis(2,6-diisopropylphenyl)imidazolinium chloride (447 mg, 97 mass % article, 1.02 mmol), potassium tert-butoxide (172 mg, 85 mass % article, 1.30 mmol) and 15.0 ml of tetrahydrofuran were added to a 30 ml Schlenk tube, and the mixture was stirred at room temperature for 20 minutes. Tetrahydrofuran was distilled off under reduced pressure, and then 15.0 ml of toluene was added thereto and the mixture was stirred at 70° C. for 5 minutes. The reaction mixture was filtered and the filtrate was added dropwise to the other 30 ml Schlenk tube added with (4-fluoro-1-naphthylethynyl(triphenylphosphine)gold (484 mg, 0.770 mmol) and 15.0 ml of toluene. After completion of the dropwise addition, the reaction mixture was heated at 70° C. for 1 hour. The reaction mixture was cooled to room temperature, and then the crude reaction product obtained by distilling off toluene under reduced pressure was purified by column chromatography (Hexane/AcOEt=100/0→1/4) using silica gel to give 472 mg of the desired compound as a white solid (yield: 81.0%).

$^1$H-NMR (300 MHz, CDCl$_3$) δ: 8.32-8.29 (m, 1H), 7.97-7.94 (m, 1H), 7.44-6.92 (m, 9H), 6.92-6.86 (m, 1H), 4.03 (s, 4H), 3.13 (sept, 4H), 1.50 (d, 12H), 1.35 (d, 12H)

[MS] EI (m/z): 756 (M$^+$), CI (m/z): 757 (MH$^+$)

Luminescence analysis: (CHCl$_3$, 77K, Ex250 nm) λ (nm): 530

Elemental Analysis:

| | |
|---|---|
| Found | C: 61.40, H: 5.91, N: 3.50 |
| Theoretical | C: 61.90, H: 5.86, N: 3.70 |

Example 36

Synthesis of Au(IPr)(4F-1NpE)[(4-fluoro-1-naphthylethynyl)[1,3-bis(2,6-diisopropylphenyl)imidazol-2-ylidene]gold]

Under an argon atmosphere, 1,3-bis(2,6-diisopropylphenyl)imidazolium chloride (447 mg, 95 mass % article, 1.00 mmol), potassium tert-butoxide (172 mg, 85 mass % article, 1.30 mmol) and 15.0 ml of tetrahydrofuran were added to a 30 ml Schlenk tube, and the mixture was stirred at room temperature for 20 minutes. Tetrahydrofuran was distilled off under reduced pressure, and then 15.0 ml of toluene was added thereto and the mixture was stirred at 70° C. for 5 minutes. The reaction mixture was filtered and the filtrate was added dropwise to the other 30 ml Schlenk tube added with (4-fluoro-1-naphthylethynyl(triphenylphosphine)gold (484 mg, 0.770 mmol) and 15.0 ml of toluene. After completion of the dropwise addition, the reaction mixture was heated at 70° C. for 1 hour. The reaction mixture was cooled to room temperature, and then the crude reaction product obtained by distilling off toluene under reduced pressure was purified by column chromatography (Hexane/AcOEt=100/0→1/4) using silica gel to give 320 mg of the desired compound as a white solid (yield: 87.6%).

$^1$H-NMR (300 MHz, CDCl$_3$) δ: 8.37-8.36 (m, 1H), 7.98-7.95 (m, 1H), 7.52-7.30 (m, 10H), 7.16 (s, 2H), 2.64 (sept, 4H), 1.42 (d, 12H), 1.23 (d, 12H)

[MS] EI (m/z): 754 (M$^+$), CI (m/z): 755 (MH$^+$)

Luminescence analysis: (CHCl$_3$, 77K, Ex250 nm) λ (nm): 529

Elemental Analysis:

| Found | C: 62.01, H: 5.44, N: 3.53 |
|---|---|
| Theoretical | C: 62.06, H: 5.61, N: 3.71 |

Example 37

Synthesis of Au(IPr)(9AntE)[(9-anthrylethynyl)[1,3-bis(2,6-diisopropylphenyl)imidazol-2-ylidene]gold]

Under an argon atmosphere, 1,3-bis(2,6-diisopropylphenyl)imidazolium chloride (IPrH$^+$Cl$^-$; 276 mg, 0.65 mmol), potassium tert-butoxide (85 mass % article, 112 mg, 0.845 mmol) and tetrahydrofuran (10 ml) were added to a 20 ml Schlenk tube, the mixture was stirred at room temperature for 20 minutes, and then tetrahydrofuran was distilled off under reduced pressure. Toluene (10 ml) was added thereto and the mixture was stirred at 70° C. for 5 minutes, and then the reaction mixture was filtered and the filtrate was added dropwise to the other 30 ml Schlenk tube added with 9-anthrylethynyl(triphenylphosphine)gold (330 mg, 0.5 mmol) and 10 ml of toluene. After completion of the dropwise addition, the reaction mixture was heated at 70° C. for 3 hours. The reaction mixture was cooled to room temperature, and then toluene was added to the reaction mixture and the mixture was washed with water to make pH to 7. The mixture was dried over sodium sulfate, and then the solvent was distilled off under reduced pressure by an evaporator. The crude reaction product was purified by column chromatography (Hexane/AcOEt=3/1) using silica gel. The resulting solid was dissolved in ethyl acetate and reprecipitated with hexane. The resulting precipitate was filtered to give 0.24 g of the desired compound as a yellow solid (yield: 62%).

$^1$H-NMR (300 MHz, CDCl$_3$) δ: 8.58-8.63 (m, 2H), 8.14 (s, 1H), 7.83-7.88 (m, 2H), 7.49-7.54 (m, 2H), 7.23-7.39 (m, 8H), 7.17 (s, 2H), 2.64-2.73 (sept, 4H), 1.48 (d, 12H), 1.24 (d, 12H)

(FAB-MS) (M/Z): 787 (M+H)$^+$

Luminescence analysis: (CHCl$_3$, 77K, Ex250 nm) λ (nm): 409, 432, 453, 481

Elemental Analysis:

| Found | C: 65.65, H: 5.66, N: 3.58 |
|---|---|
| Theoretical | C: 65.64, H: 5.76, N: 3.56 |

Example 38

Synthesis of Au(IPr)(9-PhenE)[(9-phenanthrylethynyl)[1,3-bis(2,6-diisopropylphenyl)imidazol-2-ylidene]gold]

Under an argon atmosphere, 1,3-bis(2,6-diisopropylphenyl)imidazolium chloride (IPrH$^+$Cl$^-$; 276 mg, 0.65 mmol), potassium tert-butoxide (85 mass % article, 112 mg, 0.845 mmol) and tetrahydrofuran (10 ml) were added to a 20 ml Schlenk tube, the mixture was stirred at room temperature for 20 minutes, and then tetrahydrofuran was distilled off under reduced pressure. Toluene (10 ml) was added thereto and the mixture was stirred at 70° C. for 5 minutes, and then the reaction mixture was filtered and the filtrate was added dropwise to the other 30 ml Schlenk tube added with 9-phenanthrylethynyl(triphenylphosphine)gold (330 mg, 0.5 mmol) and 10 ml of toluene. After completion of the dropwise addition, the reaction mixture was heated at 70° C. for 3 hours. The reaction mixture was cooled to room temperature, and then toluene was added to the reaction mixture and the mixture was washed with water to make pH to 7. The mixture was dried over sodium sulfate, and then the solvent was distilled off under reduced pressure by an evaporator. The crude reaction product was purified by column chromatography (Hexane/AcOEt=3/1) using silica gel. The resulting solid was dissolved in ethyl acetate and reprecipitated with hexane. The resulting precipitate was filtered to give 0.31 g of the desired compound as a yellow solid (yield: 80%).

$^1$H-NMR (300 MHz, CDCl$_3$) δ: 8.51-8.58 (m, 3H), 7.79 (s, 1H), 7.67-7.70 (m, 1H), 7.29-7.59 (m, 10H), 7.15 (s, 2H), 2.61-2.70 (sept, 4H), 1.43 (d, 12H), 1.25 (d, 12H)

(FAB-MS) (M/Z): 786 (M+H)$^+$

Luminescence analysis: (CHCl$_3$, 77K, Ex250 nm) λ (nm): 524, 534, 569

Elemental Analysis:

| Found | C: 65.55, H: 5.61, N: 3.55 |
|---|---|
| Theoretical | C: 65.64, H: 5.76, N: 3.56 |

Example 39

Synthesis of Au(IPr)(1PyrenE)[(1-pyrenylethynyl)[1,3-bis(2,6-diisopropylphenyl)imidazol-2-ylidene]gold]

Under an argon atmosphere, 1,3-bis(2,6-diisopropylphenyl)imidazolium chloride (IPrH$^+$Cl$^-$; 276 mg, 0.65 mmol), potassium tert-butoxide (85 mass % article, 112 mg, 0.845 mmol) and tetrahydrofuran (10 ml) were added to a 20 ml Schlenk tube, the mixture was stirred at room temperature for 20 minutes, and then tetrahydrofuran was distilled off under reduced pressure. Toluene (10 ml) was added thereto and the mixture was stirred at 70° C. for 5 minutes, and then the reaction mixture was filtered and the filtrate was added dropwise to the other 30 ml Schlenk tube added with 1-pyrenylethynyl(triphenylphosphine)gold (342 mg, 0.5 mmol) and 10 ml of toluene. After completion of the dropwise addition, the reaction mixture was heated at 70° C. for 3 hours. The reaction mixture was cooled to room temperature, and then toluene was added to the reaction mixture and the mixture was washed with water to make pH to 7. The mixture was dried over sodium sulfate, and then the solvent was distilled off under reduced pressure by an evaporator. The crude reaction product was purified by column chromatography (Hexane/AcOEt=3/1) using silica gel. The resulting solid was dissolved in ethyl acetate and reprecipitated with hexane. The resulting precipitate was filtered to give 0.26 g of the desired compound as a pale yellow solid (yield: 64%).

$^1$H-NMR (300 MHz, CDCl$_3$) δ: 8.58-8.60 (d, 2H), 7.89-8.10 (m, 8H), 7.50-7.55 (m, 2H), 7.21-7.39 (m, 4H), 7.16 (s, 2H), 2.63-2.72 (sept, 4H), 1.48 (d, 12H), 1.24 (d, 12H)

(FAB-MS) (M/Z): 810 (M+H)$^+$

Luminescence analysis: (CHCl$_3$, 77K, Ex250 nm) λ (nm): 397, 413

Elemental Analysis:

| | | |
|---|---|---|
| Found | C: 65.65, H: 5.66, N: 3.58 | |
| Theoretical | C: 66.39, H: 5.58, N: 3.38 | |

Example 40

Synthesis of Au(IPr)(2-FluorE)[(2-fluorenylethynyl)[1,3-bis(2,6-diisopropylphenyl)imidazol-2-ylidene]gold]

Under an argon atmosphere, 1,3-bis(2,6-diisopropylphenyl)imidazolium chloride (IPrH$^+$Cl$^-$; 276 mg, 0.65 mmol), potassium tert-butoxide (85 mass % article, 112 mg, 0.845 mmol) and tetrahydrofuran (10 ml) were added to a 20 ml Schlenk tube, the mixture was stirred at room temperature for 20 minutes, and then tetrahydrofuran was distilled off under reduced pressure. Toluene (10 ml) was added thereto and the mixture was stirred at 70° C. for 5 minutes, and then the reaction mixture was filtered and the filtrate was added dropwise to the other 30 ml Schlenk tube added with 2-fluorenylethynyl(triphenylphosphine)gold (324 mg, 0.5 mmol) and 10 ml of toluene. After completion of the dropwise addition, the reaction mixture was heated at 70° C. for 3 hours. The reaction mixture was cooled to room temperature, and then toluene was added to the reaction mixture and the mixture was washed with water to make pH to 7. The mixture was dried over sodium sulfate, and then the solvent was distilled off under reduced pressure by an evaporator. The crude reaction product was purified by column chromatography (Hexane/AcOEt=5/1-3/1) using silica gel. The resulting solid was dissolved in ethyl acetate and reprecipitated with hexane. The resulting precipitate was filtered to give 0.30 g of the desired compound as a yellow solid (yield: 77%).

$^1$H-NMR (300 MHz, CDCl$_3$) δ: 7.64-7.67 (d, 2H), 7.44-7.54 (m, 5H), 7.18-7.34 (m, 7H), 7.18 (s, 2H), 3.74 (s, 2H), 2.57-2.66 (sept, 4H), 1.39 (d, 12H), 1.24 (d, 12H)

(FAB-MS) (M/Z): 775 (M+H)$^+$

Luminescence analysis: (CHCl$_3$, 77K, Ex250 nm) λ (nm): 481, 500, 511, 520

Elemental Analysis:

| | | |
|---|---|---|
| Found | C: 64.85, H: 5.87, N: 3.60 | |
| Theoretical | C: 65.11, H: 5.85, N: 3.62 | |

Example 41

Synthesis of Au(IPr)(5F7Pr-8QE)[(5-fluoro-7-propyl-8-quinolylethynyl)[1,3-bis(2,6-diisopropylphenyl)imidazol-2-ylidene]gold]

Under an argon atmosphere, 1,3-bis(2,6-diisopropylphenyl)imidazolium chloride (173 mg, 95 mass % article, 0.387 mmol), potassium tert-butoxide (66.4 mg, 85 mass % article, 0.503 mmol) and 5.8 mL of tetrahydrofuran were added to a 30 mL Schlenk tube, and the mixture was stirred at room temperature for 20 minutes. Tetrahydrofuran was distilled off under reduced pressure, and then 5.8 mL of toluene was added thereto and the mixture was stirred at 70° C. for 5 minutes. The reaction mixture was filtered and the filtrate was added dropwise to the other 30 mL Schlenk tube added with (5-fluoro-2-methyl-8-quinolylethynyl)(triphenylphosphine)gold (200 mg, 0.298 mmol) and 5.8 mL of toluene. After completion of the dropwise addition, the reaction mixture was heated at 70° C. for 1 hour. The reaction mixture was cooled to room temperature, and then the crude reaction product obtained by distilling off toluene under reduced pressure was purified by column chromatography (Hexane/AcOEt=100/0→1/4) using silica gel to give 146 mg of the desired compound as a white solid (yield: 47.6%).

$^1$H-NMR (300 MHz, CDCl$_3$) δ: 8.93-8.91 (m, 1H), 8.24-8.20 (m, 1H), 7.51-7.46 (m, 2H), 7.30-7.22 (m, 5H), 7.14 (s, 2H), 6.96 (d, 1H), 2.89-2.84 (m, 2H), 2.63 (sept, 4H), 1.62-1.55 (m, 2H), 1.40 (d, 12H), 1.22 (d, 12H), 0.82 (t, 3H)

Luminescence analysis: (CHCl$_3$, 77K, Ex250 nm) λ (nm): 419 [MS] EI (m/z): 797 (M$^+$), CI (m/z): 798 (MH$^+$)

Elemental Analysis:

| | | |
|---|---|---|
| Found | C: 61.64, H: 5.65, N: 5.15 | |
| Theoretical | C: 61.72, H: 5.94, N: 5.27 | |

Example 42

Synthesis of Au(IPr)(5F3Bu-8QE)[(5-fluoro-3-butyl-8-quinolylethynyl)[1,3-bis(2,6-diisopropylphenyl)-imidazol-2-ylidene]gold]

Under an argon atmosphere, 1,3-bis(2,6-diisopropylphenyl)imidazolium chloride (254 mg, 95 mass % article, 0.569 mmol), potassium tert-butoxide (97.6 mg, 85 mass % article, 0.740 mmol) and 9.0 mL of tetrahydrofuran were added to a 30 mL Schlenk tube, and the mixture was stirred at room temperature for 20 minutes. After tetrahydrofuran was distilled off under reduced pressure, 9.0 mL of toluene was added thereto and the mixture was stirred at 70° C. for 5 minutes. The reaction mixture was filtered and the filtrate was added dropwise to the other 30 mL Schlenk tube added with (5-fluoro-3-butyl-8-quinolylethynyl)(triphenylphosphine)gold (300 mg, 0.438 mmol) and 9.0 mL of toluene. After completion of the dropwise addition, the reaction mixture was heated at 70° C. for 1 hour. The reaction mixture was cooled to room temperature, and then the crude reaction product obtained by distilling off toluene under reduced pressure was purified by column chromatography (Hexane/AcOEt=100/0→1/4) using silica gel to give 210 mg of the desired compound as a white solid (yield: 59.1%).

$^1$H-NMR (300 MHz, CDCl$_3$) δ: 8.79 (d, 1H), 8.03-8.01 (m, 1H), 7.66-7.60 (m, 1H), 7.52-7.48 (m, 2H), 7.31-7.28 (m, 4H), 7.12 (s, 2H), 6.98-6.92 (m, 1H), 2.74 (t, 2H), 2.64 (sept, 4H), 1.68-1.59 (m, 2H), 1.43-1.41 (m, 2H), 1.40 (d, 12H), 1.22 (d, 12H), 0.94 (t, 3H)

[MS] FAB (m/z): 812 (MH$^+$)

Luminescence analysis: (CHCl$_3$, 77K, Ex250 nm) λ (nm): 403, 543

Elemental Analysis:

| | | |
|---|---|---|
| Found | C: 61.69, H: 5.91, N: 5.17 | |
| Theoretical | C: 62.14, H: 6.08, N: 5.18 | |

Example 43

Synthesis of Au(IPr)(5F3Me-8QE)[(5-fluoro-3-methyl-8-quinolylethynyl)[1,3-bis(2,6-diisopropylphenyl)-imidazol-2-ylidene]gold]

Under an argon atmosphere, 1,3-bis(2,6-diisopropylphenyl)imidazolium chloride (136 mg, 95 mass % article, 0.303 mmol), potassium tert-butoxide (51.9 mg, 85 mass % article, 0.393 mmol) and 5.0 mL of tetrahydrofuran were added to a 30 mL Schlenk tube, and the mixture was stirred at room temperature for 20 minutes. After tetrahydrofuran was distilled off under reduced pressure, 5.0 mL of toluene was added thereto and the mixture was stirred at 70° C. for 5 minutes. The reaction mixture was filtered and the filtrate was added dropwise to the other 30 mL Schlenk tube added with (5-fluoro-3-methyl-8-quinolylethynyl)(triphenylphosphine)gold (150 mg, 0.233 mmol) and 5.0 mL of toluene. After completion of the dropwise addition, the reaction mixture was heated at 70° C. for 1 hour. The reaction mixture was cooled to room temperature, and then the crude reaction product obtained by distilling off toluene under reduced pressure was purified by column chromatography (Hexane/AcOEt=100/0→1/4) using silica gel to give 82.0 mg of the desired compound as a white solid (yield: 45.7%).

$^1$H-NMR (300 MHz, CDCl$_3$) δ: 8.79 (d, 1H), 8.05-8.02 (m, 1H), 7.65-7.60 (m, 1H), 7.53-7.47 (m, 2H), 7.31-7.26 (m, 4H), 7.12 (s, 2H), 6.98-6.92 (m, 1H), 2.64 (sept, 4H), 2.46 (s, 3H), 1.40 (d, 12H), 1.21 (d, 12H)

[MS] EI (m/z): 769 (M$^+$), CI (m/z): 770 (MH$^+$)

Luminescence analysis: (CHCl$_3$, 77K, Ex250 nm) λ (nm): 406, 547

Elemental Analysis:

| Found | C: 60.58, H: 5.27, N: 5.42 |
|---|---|
| Theoretical | C: 60.85, H: 5.63, N: 5.46 |

Example 44

Synthesis of Au(IPr)(5F2Me-8QE)[(5-fluoro-2-methyl-8-quinolylethynyl)[1,3-bis(2,6-diisopropylphenyl)-imidazol-2-ylidene]gold]

Under an argon atmosphere, 1,3-bis(2,6-diisopropylphenyl)imidazolium chloride (298 mg, 95 mass % article, 0.667 mmol), potassium tert-butoxide (114 mg, 85 mass % article, 0.867 mmol) and 14.0 mL of tetrahydrofuran were added to a 30 mL Schlenk tube, and the mixture was stirred at room temperature for 20 minutes. After tetrahydrofuran was distilled off under reduced pressure, 14.0 mL of toluene was added thereto and the mixture was stirred at 70° C. for 5 minutes. The reaction mixture was filtered and the filtrate was added dropwise to the other 30 mL Schlenk tube added with (5-fluoro-2-methyl-8-quinolylethynyl)(triphenylphosphine)gold (330 mg, 0.513 mmol) and 6.0 mL of toluene. After completion of the dropwise addition, the reaction mixture was heated at 70° C. for 1 hour. The reaction mixture was cooled to room temperature, and then the crude reaction product obtained by distilling off toluene under reduced pressure was purified by column chromatography (Hexane/AcOEt=100/0→1/4) using silica gel to give 296 mg of the desired compound as a white solid (yield: 75.0%).

$^1$H-NMR (300 MHz, CDCl$_3$) δ: 8.16 (d, 1H), 7.67-7.62 (m, 1H), 7.52-7.46 (m, 2H), 7.32-7.24 (m, 4H), 7.21 (d, 1H), 7.13 (s, 2H), 6.93-6.88 (m, 1H), 2.72 (s, 3H), 2.64 (sept, 4H), 1.41 (d, 12H), 1.22 (d, 12H)

[MS] EI (m/z): 769 (M$^+$), CI (m/z): 770 (MH$^+$)

Luminescence analysis: (CHCl$_3$, 77K, Ex250 nm) λ (nm): 419

Elemental Analysis:

| Found | C: 60.26, H: 5.41, N: 5.40 |
|---|---|
| Theoretical | C: 60.85, H: 5.63, N: 5.46 |

Example 45

Synthesis of Au(IPr)(5F2Me-8QE)[(5-fluoro-2-propyl-8-quinolylethynyl)[1,3-bis(2,6-diisopropylphenyl)-imidazol-2-ylidene]gold]

Under an argon atmosphere, 1,3-bis(2,6-diisopropylphenyl)imidazolium chloride (233.9 mg, 95 mass % article, 0.523 mmol), potassium tert-butoxide (89.7 mg, 85 mass % article, 0.680 mmol) and 8.00 mL of tetrahydrofuran were added to a 30 mL Schlenk tube, and the mixture was stirred at room temperature for 20 minutes. After tetrahydrofuran was distilled off under reduced pressure, 8.00 mL of toluene was added thereto and the mixture was stirred at 70° C. for 5 minutes. The reaction mixture was filtered and the filtrate was added dropwise to the other 30 mL Schlenk tube added with (5-fluoro-2-propyl-8-quinolylethynyl)(triphenylphosphine)gold (270 mg, 0.402 mmol) and 8.0 mL of toluene. After completion of the dropwise addition, the reaction mixture was heated at 70° C. for 1 hour. The reaction mixture was cooled to room temperature, and then the crude reaction product obtained by distilling off toluene under reduced pressure was purified by column chromatography (Hexane/AcOEt=100/0→1/1) using silica gel to give 201 mg of the desired compound as a yellow solid (yield: 62.7%).

$^1$H-NMR (300 MHz, CDCl$_3$) δ: 8.16 (d, 1H), 7.65-7.60 (m, 1H), 7.51-7.46 (m, 2H), 7.31-7.25 (m, 4H), 7.22 (d, 1H), 7.13 (s, 2H), 6.92-6.88 (m, 1H), 2.96-2.91 (m, 2H), 2.64 (sept, 4H), 1.92-1.78 (m, 2H), 1.41 (d, 12H), 1.22 (d, 12H), 1.01 (t, 3H)

[MS] EI (m/z): 797 (M$^+$), CI (m/z): 798 (MH$^+$)

Luminescence analysis: (CHCl$_3$, 77K, Ex250 nm) λ (nm): 401, 535

Elemental Analysis:

| Found | C: 61.40, H: 5.57, N: 5.25 |
|---|---|
| Theoretical | C: 61.72, H: 5.94, N: 5.27 |

Example 46

Synthesis of Au(IPr)(4Bz-PE)[(4-benzoylphenylethynyl)[1,3-bis(2,6-diisopropylphenyl)imidazol-2-ylidene]gold]

Under an argon atmosphere, 1,3-bis(2,6-diisopropylphenyl)imidazolium chloride (IPrH$^+$Cl$^-$; 276 mg, 0.65 mmol), potassium tert-butoxide (85 mass % article, 112 mg, 0.845 mmol) and tetrahydrofuran (10 ml) were added to a 20 ml Schlenk tube, the mixture was stirred at room temperature for 20 minutes, and then tetrahydrofuran was distilled off under reduced pressure. Toluene (10 ml) was added thereto and the mixture was stirred at 70° C. for 5 minutes, and then the reaction mixture was filtered and the filtrate was added dropwise to the other 30 ml Schlenk tube added with 4-benzoylphenylethynyl(triphenylphosphine)gold (332 mg, 0.5 mmol) and 10 ml of toluene. After completion of the dropwise addition, the reaction mixture was heated at 70° C. for 3 hours. The reaction mixture was cooled to room temperature, and then toluene was added to the reaction mixture and the mixture was washed with water to make pH to 7. The mixture was dried over sodium sulfate, and then the solvent was distilled off under reduced pressure by an evaporator. The crude reaction product was purified by column chromatography (Hexane/AcOEt=3/1) using silica gel. The resulting solid was dissolved in ethyl acetate and represipitated with hexane. The resulting precipitate was filtered to give 0.37 g of the desired compound as a white solid (yield: 93%).

$^1$H-NMR (300 MHz, CDCl$_3$) δ: 7.26-7.71 (m, 15H), 7.14 (s, 2H), 2.56-2.65 (sept, 4H), 1.48 (d, 12H), 1.24 (d, 12H)

(FAB-MS) (M/Z): 791 (M+H)$^+$

Luminescence analysis: (CHCl$_3$, 77K, Ex250 nm) λ (nm): 474, 507

Elemental Analysis:

| Found | C: 63.56, H: 5.47, N: 3.47 |
|---|---|
| Theoretical | C: 63.79, H: 5.74, N: 3.54 |

Example 47

Synthesis of Au(IPr)(PzE)[(pyrazinylethynyl)[1,3-bis(2,6-diisopropylphenyl)imidazol-2-ylidene]gold]

Under an argon atmosphere, 1,3-bis(2,6-diisopropylphenyl) imidazolium chloride (IPrH$^+$Cl$^-$; 225 mg, 0.53 mmol), potassium tert-butoxide (85 mass % article, 91 mg, 0.69 mmol) and tetrahydrofuran (8 ml) were added to a 15 mL Schlenk tube, the mixture was stirred at room temperature for 15 minutes, and then tetrahydrofuran was distilled off under reduced pressure. Toluene (8 ml) was added thereto and the mixture was stirred at 70° C. for 5 minutes, and then the reaction mixture was filtered and the filtrate was added dropwise to the other 30 mL Schlenk tube added with pyrazinylethynyl(triphenylphosphine)gold (225 mg, 0.53 mmol) and 8 ml of toluene. After completion of the dropwise addition, the reaction mixture was heated at 70° C. for 3 hours. The reaction mixture was cooled to room temperature, and then toluene was added to the reaction mixture and the mixture was washed with water to make pH to 7. The mixture was dried over sodium sulfate, and then the solvent was distilled off under reduced pressure by an evaporator. The crude reaction product was purified by column chromatography (Hexane/AcOEt=3/1) using silica gel. The resulting solid was dissolved in ethyl acetate and represipitated with hexane. The resulting precipitate was filtered to give 0.31 g of the desired compound as a yellow solid (yield: 89%).

$^1$H-NMR (300 MHz, CDCl$_3$) δ: 8.45 (d, 1H), 8.30 (dd, 1H), 8.17 (d, 1H), 7.52-7.49 (m, 2H), 7.31-7.29 (m, 4H), 2.61-2.55 (sept, 4H), 1.36 (d, 12H), 1.22 (d, 12H)

(FAB-MS) (M/Z): 689 (MH$^+$)

Luminescence analysis: (CHCl$_3$, 77K, Ex250 nm) λ (nm): 445, 463, 475, 491

Elemental Analysis:

| Found | C: 57.41, H: 5.49, N: 8.06 |
|---|---|
| Theoretical | C: 57.55, H: 5.71, N: 8.14 |

Example 48

Synthesis of Au(IPr)(4Ac-PE)[(4-acetylphenylethynyl)[1,3-bis(2,6-diisopropylphenyl)imidazol-2-ylidene]gold]

Under an argon atmosphere, 1,3-bis(2,6-diisopropylphenyl)imidazolium chloride (IPrH$^+$Cl$^-$; 255 mg, 0.6 mmol), potassium tert-butoxide (85 mass % article, 88.6 mg, 0.79 mmol) and tetrahydrofuran (9 ml) were added to a 20 ml Schlenk tube, the mixture was stirred at room temperature for 15 minutes, and then tetrahydrofuran was distilled off under reduced pressure. Toluene (9 ml) was added thereto and the mixture was stirred at 70° C. for 5 minutes, and then the reaction mixture was filtered and the filtrate was added dropwise to the other 30 ml Schlenk tube added with 4-acetylphenylethynyl(triphenylphosphine)gold (280 mg, 0.465 mmol) and 9 ml of toluene. After completion of the dropwise addition, the reaction mixture was heated at 70° C. for 3 hours. The reaction mixture was cooled to room temperature, and then toluene was added to the reaction mixture and the mixture was washed with water to make pH to 7. The mixture was dried over sodium sulfate, and then the solvent was distilled off under reduced pressure by an evaporator. The crude reaction product was purified by column chromatography (Hexane/AcOEt=5/1) using silica gel. The resulting solid was washed and filtered with hexane to give 0.33 g of the desired compound as a pale yellow solid (yield: 96%).

$^1$H-NMR (300 MHz, CDCl$_3$) δ: 7.69-7.72 (m, 2H), 7.42-7.53 (m, 2H), 7.31-7.37 (m, 6H), 7.14 (s, 2H), 2.54-2.71 (sept, 4H), 2.50 (s, 3H), 1.48 (d, 12H), 1.24 (d, 12H)

[MS] EI (m/z): 728 (M$^+$−1), CI (m/z): 729 (MH$^+$)

Luminescence analysis: (CHCl$_3$, 77K, Ex250 nm) λ (nm): 471, 504

Elemental Analysis:

| Found | C: 61.06, H: 5.97, N: 3.87 |
|---|---|
| Theoretical | C: 60.98, H: 5.95, N: 3.84 |

Example 49

Preparation of Organic Electroluminescence Device Containing Au(IPr)(8QE) in Organic Emitting Layer as Light Emitting Material By using a glass with indium tin oxide (hereinafter, abbreviated to ITO) coating film manufactured by EHC as a transparent electrode substrate and using a vacuum vapor deposition device manufactured by ULVAC KIKO Inc., a hole transport layer 3 comprising N,N'-di(naphthalene-1-yl)-N, N'-diphenylbenzidine (hereinafter, abbreviated to αNPD) was vacuum-vapor-deposited at a film thickness of 40 nm, a light emitting layer 4 containing 9.8% by weight of Au(IPr)(8QE) in n-butyltriphenyl germanium was vacuum-vapor-deposited at a film thickness of 30 nm, a hole block layer 5 comprising 3-(4-biphenylyl)-4-phenyl-5-tert-butylphenyl-1, 2,4-triazole (hereinafter, abbreviated to TAZ) was vacuum-vapor-deposited at 20 nm, an electron transport layer 6 comprising tris-(8-hydroxyquinoline)aluminum (hereinafter, abbreviated to Alq) was vacuum-vapor-deposited at 30 nm and aluminum (Al) as an electrode 7 was vacuum-vapor-deposited at 100 nm on the same substrate at a degree of vacuum of $2\times10^{-3}$ Pa or less to prepare an electroluminescence device. (see FIG. 1).

Further, the vapor deposition was carried out by charging the material in a crucible placed opposed to the substrate and heating the material with the crucible.

When an interelectrode voltage was raised by performing energization making the ITO electrode 2 as a positive pole and making the Al electrode 7 as a negative pole in the device, the device started to emit blue light of the degree which can be clearly recognized by the naked eye from near +5 V and a luminance of the emitted light at +18 V was 205 cd/m². Efficiency of a current relating to the light emitting of this device was determined by the following formula.

Current efficiency=(luminance per unit area)/(current density per unit area)

The current efficiency thus determined was 0.31 cd/A at +15 V.

The color of the emitted light of this device was evaluated using an organic EL evaluation apparatus manufactured by PRECISE GAUGES co., ltd. A value of chromaticity coordinate determined according to JIS Z8701 from the emission spectrum of this device obtained at the interelectrode voltage of +18 V was x=0.16 and y=0.14.

Example 50

Preparation of Organic Electroluminescence Device Containing Au(IMes)(8QE) in Organic Emitting Layer as Light Emitting Material The electroluminescence device was prepared similarly to Example 49 except that the light emitting layer 4 containing 9.8% by weight of Au(IMes)(8QE) in n-butyltriphenyl germanium was vacuum-vapor-deposited at a film thickness of 30 nm.

When the interelectrode voltage was raised by performing energization making the ITO electrode 2 as the positive pole and making the Al electrode 7 as the negative pole in the above device, the device started to emit blue light of the degree which can be clearly recognized by the naked eye from near +6 V and the luminance of the emitted light at +20 V was 170 cd/m². The maximum current efficiency of this device was 37 cd/A at +15 V.

The value of chromaticity coordinate determined according to JIS Z8701 from the emission spectrum of this device obtained at the interelectrode voltage of +20 V was x=0.15 and y=0.13.

Example 51

Preparation of Organic Electroluminescence Device Containing Au(IAd)(8QE) in Organic Emitting Layer as Light Emitting Material The electro-luminescence device was prepared similarly to Example 49 except that the light emitting layer 4 containing 9.8% by weight of Au(IAd)(8QE) in n-butyltriphenyl germanium was vacuum-vapor-deposited at the film thickness of 30 nm.

When the interelectrode voltage was raised by performing energization making the ITO electrode 2 as the positive pole and making the Al electrode 7 as the negative pole in the above device, the device started to emit blue light of the degree which can be clearly recognized by the naked eye from near +9 V and the luminance of the emitted light at +20 V was 63 cd/m². The maximum current efficiency of this device was 0.11 cd/A at +17 V.

The value of chromaticity coordinate determined according to JIS Z8701 from the emission spectrum of this device obtained at the interelectrode voltage of +20 V was x=0.27 and y=0.20.

Comparative Example 1

Preparation of Organic Electroluminescence Device Containing Au(PPh$_3$) (8QE) in Organic Emitting Layer as Light Emitting Material The electroluminescence device was prepared similarly to Example 49 except that the hole transport layer 3 comprising αNPD was vacuum-vapor-deposited at a film thickness of 40 nm, the light emitting layer 4 containing 9.6% by weight of Au(PPh$_3$) (8QE) in n-butyltriphenyl germanium was vacuum-vapor-deposited at a film thickness of 30 nm, the hole block layer 5 comprising TAZ was vacuum-vapor-deposited at 20 nm, the electron transport layer 6 comprising Alq was vacuum-vapor-deposited at 30 nm and aluminum (Al) as an electrode 7 was vacuum-vapor-deposited at 100 nm on the ITO substrate.

When the interelectrode voltage was raised by performing energization making the ITO electrode 2 as the positive pole and making the Al electrode 7 as the negative pole in the above device, the device started to emit blue light of the degree which can be clearly recognized by the naked eye from near +7 V and the luminance of the emitted light at +21 V was 119 cd/m². The maximum current efficiency of this device was 0.28 cd/A at +15 V.

The value of chromaticity coordinate determined according to JIS Z8701 from the emission spectrum of this device obtained at the interelectrode voltage of +21 V was x=0.15 and y=0.11.

Reference Example 1

Synthesis of 8-trifluoromethanesulfonyloxyquinoline

A yellow solution in which 7.26 g (50 mmol) of 8-quinolinol, 50 ml of methylene chloride and 9.1 ml (65 mmol) of triethylamine were mixed was cooled to 0° C. in an ice-bath, and then 9.3 ml (55 mmol) of trifluoromethanesulfonic anhydride was added dropwise thereto. After completion of the dropwise addition, the reaction mixture varied to approximately black was stirred for 1 hour while the reaction temperature was maintained to 0° C. After completion of the reaction, 200 ml of water and 250 ml of diethyl ether were added to the reaction mixture to separate the solution. The resulting organic layer was washed with 1 mol/L (liter) of hydrochloric acid (125 ml×2 times) and water (125 ml×once) in the order and subsequently dried over magnesium sulfate. After filtration, diethyl ether was distilled off from the filtrate under reduced pressure and the resulting residue was dissolved in 250 ml of hexane at 70° C. The insolubles were filtered off, and then the filtrate was cooled to give 12.6 g of the desired compound as a brownish white crystal (yield: 91%).

$^1$H-NMR (300 MHz, CDCl$_3$) δ: 9.11-9.03 (m, 1H), 8.30-8.19 (m, 1H), 7.89-7.81 (m, 1H), 7.65-7.50 (m, 3H)
EI-MS (m/e): 277 (M$^+$), CI-MS (m/z): 278 (MH$^+$)

Reference Example 2

Synthesis of 8-quinolylethyne (First Step)

A 25 mL Schlenk tube was replaced with argon gas and 12 g (45 mmol) of 8-trifluoromethanesulfonyloxyquinoline, 500 mg (0.44 mmol) of tetrakis(triphenylphosphine)palladium, 50 ml of piperidine and 4.75 ml (49 mmol) of 2-methyl-3-butyn-2-ol were added thereto, followed by stirring of the mixture at 80° C. for 45 minutes.

A saturated aqueous ammonium chloride solution was added to the reaction mixture, and then the mixture was extracted with diethyl ether and dried over magnesium sulfate and the solvent was distilled off under reduced pressure by an evaporator. The crude reaction product was purified by column chromatography (developing solvent: n-hexane/ethyl acetate=100/0-1/1) using silica gel to give dimethylhydroxymethyl-8-quinolylacetylene as a transparent yellow oil. Yield: 8.5 g (yield: 90%).

$^1$H-NMR (300 MHz, CDCl$_3$) δ: 1.73 (s, 6H), 4.64 (s, 1H), 7.34-7.43 (m, 1H), 7.44-7.49 (m, 1H), 7.76 (dd, 1H), 7.85 (dd, 1H), 8.11-8.15 (dd, 1H), 9.12-9.14 (dd, 1H)

EI-MS (M/Z): 211 (M$^+$−1), CI-MS (M/Z): 212 (MH$^+$)

(Second Step)

8.5 g (40 mmol) of Dimethylhydroxymethyl-8-quinolylacetylene and 1. g (45 mmol) of sodium hydroxide (manufactured by KISHIDA CHEMICAL CO., Ltd., 0.7 mm granular, 98%) were placed in a 300 mL two-neck flask equipped with a reflux condenser and the air inside the flask was replaced with argon gas. 200 mL of toluene was added thereto and the mixture was refluxed at 120° C. for 0.5 hours. Diethyl ether was added to the reaction mixture, the mixture was washed with a saturated aqueous ammonium chloride solution and dried over magnesium sulfate, and then the solvent was distilled off under reduced pressure by an evaporator. Hexane (250 ml) was added to the residue and the mixture was heated to 70° C. After filtering out the insolubles, the desired compound precipitated by cooling it to −78° C. was filtered and washed with cold hexane (−78° C., 100 ml) and then dried under reduced pressure to give 4.9 g of the desired compound as a yellowish white solid (yield: 80%).

$^1$H-NMR (300 MHz, CDCl$_3$) δ: 3.60 (s, 1H), 7.32-7.53 (m, 2H), 7.83 (dd, 1H), 7.93 (dd, 1H), 8.17 (dd, 1H), 9.06-9.08 (m, 1H)

EI-MS (M/Z): 153 (M$^+$−1), CI-MS (M/Z): 154 (MH$^+$)

Reference Example 3

Synthesis of 8-quinolylethynyl(triphenylphosphine)gold (Au(PPh$_3$) (8QE))

Under an argon atmosphere, Au(PPh$_3$)Cl (0.20 g, 0.40 mmol), 8-quinolylethyne (92 mg, 0.60 mmol) and ethanol (8 ml) were added to a Schlenk tube (25 mL) and sodium ethoxide (165 μl, 0.42 mmol; 2.55 M, ethanol solution) was added dropwise thereto, followed by stirring of the mixture at room temperature for 17 hours. After completion of the reaction, the resulting white precipitate was filtered and washed with ethanol (5 ml×three times), water (5 ml×four times) and ethanol (5 ml×three times) and dried under vacuum to give 0.23 g of the desired compound as a pale yellow powder (yield: 96%).

$^1$H-NMR (400 MHz, CDCl$_3$) δ: 9.07 (dd, 1H), 8.12 (dd, 1H), 7.99 (dd, 1H), 7.68 (dd, 1H), 7.62-7.36 (m, 17H) $^{31}$P-NMR (160 MHz, CDCl$_3$): 42.8

FAB-MS (M/Z): 612 (M+H)$^+$

Luminescence analysis: (CHCl$_3$, 77K, Ex250 nm) λ (nm): 380, 526, 567

Elemental Analysis:

| Found | C: 57.06, H: 3.45, N: 2.33 |
| Theoretical | C: 56.97, H: 3.46, N: 2.29 |

Reference Example 4

Synthesis of 5-fluoro-8-trifluoromethanesulfonyloxyquinoline 3.91 g (24 mmol) of 5-Fluoro-8-quinolinol and 24 ml of methylene chloride were added. The internal temperature was cooled to 4° C. in an ice-water bath, and then 4.3 ml (31 mmol) of triethylamine was added thereto. After the internal temperature descends down to 1° C., 4.4 ml (26.4 mmol) of trifluoromethanesulfonic anhydride was added dropwise thereto. The reaction mixture varied to approximately black was stirred in the ice-water bath for 1 hour. After completion of the reaction, the reaction mixture was poured into water and the mixture was extracted with diethyl ether. The extract was washed with 1 mol/L (liter) of hydrochloric acid and water, and then the solvent was distilled off under reduced pressure by an evaporator to give a brown solid. The solid was dissolved in hot hexane (70° C.) and suction filtration was carried out to remove the insolubles. The filtrate was cooled to −78° C. to give 6.21 g of the desired compound as a brownish white solid (yield: 87%).

$^1$H-NMR (300 MHz, CDCl$_3$) δ: 7.20-7.28 (m, 1H), 7.55-7.63 (m, 2H), 8.47 (dd, 1H), 9.11 (dd, 1H)

EI-MS (M/e): 295 (M$^+$), CI-MS (M/e): 296 (MH$^+$)

Reference Example 5

Synthesis of 5-fluoro-8-quinolylethyne (First Step)

The air inside a 25 ml Schlenk tube was replaced with argon gas and 592 mg (2 mmol) of 5-fluoro-8-trifluoromethanesulfonyloxyquinoline, 46.2 mg (0.04 mmol) of tetrakis(triphenylphosphine)palladium, 6 ml of piperidine and 290 μl (3 mmol) of 2-methyl-3-butyn-2-ol were added thereto, followed by stirring of the mixture at 80° C. for 1.5 hours.

After completion of the reaction, a saturated aqueous ammonium chloride solution (60 ml) was added to the reaction mixture and the mixture was extracted with methylene chloride (40 ml), followed by distilling off of the solvent from the extract using an evaporator. The resulting residue was purified by silica gel column chromatography (developing solvent: hexane/ethyl acetate=100/0-1/1) to give 0.27 g of the desired compound (dimethylhydroxymethyl-(5-fluoro-8-quinolyl)acetylene) as a yellow oil (yield: 59%).

$^1$H-NMR (300 MHz, CDCl$_3$) δ: 1.71 (s, 6H), 3.85 (s, 1H), 7.14-7.18 (m, 1H), 7.44-7.49 (m, 1H), 7.78-7.83 (m, 1H), 8.42 (dd, 1H), 9.10-9.12 (m, 1H)

EI-MS (M/e): 229 (M$^+$), CI-MS (M/Z): 230 (MH$^+$)

(Second Step)

The air inside a 50 mL two-neck flask equipped with a reflux condenser was replaced with argon gas and 0.27 g (1.17 mmol) of dimethylhydroxymethyl-(5-fluoro-8-quinolyl)acetylene obtained in the first step and 56 mg (1.37 mmol) of sodium hydroxide were added thereto. 9 ml of toluene was added thereto and the mixture was refluxed at 120° C. for 0.5 hour. After completion of the reaction, the reaction mixture was allowed to cool to room temperature and diethyl ether (20 ml) was added to the reaction mixture. The mixture was washed with a saturated aqueous ammonium chloride solution (40 ml) and the solvent was distilled off under reduced pressure by an evaporator to give 0.19 g of the desired compound (5-fluoro-8-quinolylethyne) as a yellow solid (yield: 95%).

$^1$H-NMR (300 MHz, CDCl$_3$) δ: 3.55 (s, 1H), 7.17-7.23 (m, 1H), 7.51-7.55 (m, 1H), 7.90-7.95 (m, 1H), 8.44-8.49 (m, 1H), 9.10-9.12 (m, 1H)

EI-MS (M/e): 171 (M$^+$), CI-MS (M/e): 172 (MH$^+$)

Reference Example 6

Synthesis of (5-fluoro-8-quinolylethynyl)(triphenylphosphine)gold [Au(PPh$_3$)(5F-8QE)]

Under an argon atmosphere, Au(PPh$_3$)Cl (0.20 g, 0.40 mmol), 5-fluoro-8-quinolylethyne (102 mg, 0.60 mmol) and ethanol (8 ml) were added to a 25 ml Schlenk tube, and then sodium ethoxide (165 μl, 0.42 mmol: 2.55 mol/L (liter) in ethanol solution) was added dropwise thereto, followed by stirring of the mixture at room temperature for 17 hours. After completion of the reaction, the resulting white precipitate was filtered and successively washed with ethanol (5 ml×three times), water (5 ml×four times) and ethanol (5 ml×three times), followed by drying under vacuum to give 0.22 g of the desired compound as a pale yellow powder (yield: 88%).

$^1$H-NMR (400 MHz, CDCl$_3$) δ: 9.11 (dd, 1H), 8.40 (dd, 1H), 7.91 (dd, 1H), 7.62-7.42 (m, 16H), 7.13 (dd, 1H) $^{31}$P-NMR (160 MHz, CDCl$_3$): 42.8

FAB-MS (M/Z): 630 (M+H)$^+$

Luminescence analysis: (CHCl$_3$, 77K, Ex250 nm) λ (nm): 392, 534

Elemental Analysis:

| | |
|---|---|
| Found | C: 55.26, H: 3.34, N: 2.31 |
| Theoretical | C: 55.34, H: 3.20, N: 2.23 |

Reference Example 7

Synthesis of 5-chloro-8-trifluoromethanesulfonyloxyquinoline 4.49 g (25 mmol) of 5-Chloro-8-quinolinol and 25 ml of methylene chloride were added. The internal temperature was cooled to 4° C. in an ice-water bath, and then 4.5 ml (32.5 mmol) of triethylamine was added thereto. After the internal temperature descends down to 1° C., 4.63 ml (27.5 mmol) of trifluoromethanesulfonic anhydride was added dropwise thereto. The reaction mixture varied to approximately black was stirred in the ice-water bath for 1 hour. After completion of the reaction, the reaction mixture was poured into water and the mixture was extracted with diethyl ether. The extract was washed with 1 mol/L (liter) of hydrochloric acid and water, and then the solvent was distilled off under reduced pressure by an evaporator to give a brown solid. The solid was dissolved in hot hexane (70° C.) and suction filtration was carried out to remove the insolbles. The filtrate was cooled to −78° C. to give 7.0 g of the desired compound as a pale orange-color solid (yield: 90%).

$^1$H-NMR (300 MHz, CDCl$_3$) δ: 7.20-7.28 (m, 1H), 7.55-7.63 (m, 2H), 8.47 (dd, 1H), 9.11 (dd, 1H)

EI-MS (M/e): 295 (M$^+$), CI-MS (M/e): 296 (MH$^+$)

Reference Example 8

Synthesis of 5-chloro-8-quinolylethyne (First Step)

A 100 ml three-neck flask was replaced with argon gas and 7.0 g (22.5 mmol) of 5-chloro-8-trifluoromethanesulfonyloxyquinoline, 266 mg (0.23 mmol) of tetrakis(triphenylphosphine)palladium, 23 ml of piperidine and 2.4 ml (24.7 mmol) of 2-methyl-3-butyn-2-ol were added thereto, followed by stirring of the mixture at 80° C. for 1.5 hours.

After completion of the reaction, a saturated aqueous ammonium chloride solution (60 ml) was added to the reaction mixture and the mixture was extracted with methylene chloride (40 ml). The solvent was distilled off from the extract using an evaporator to give 6.4 g of crude (dimethylhydroxymethyl-(5-chloro-8-quinolyl)acetylene). The product was used for second step without purification.

(Second Step)

The air inside a 200 mL two-neck flask equipped with a reflux condenser was replaced with argon gas and 5.5 g (22.5 mmol) of dimethylhydroxymethyl-(5-chloro-8-quinolyl)acetylene obtained in the first step and 0.9 g (22.5 mmol) of sodium hydroxide were added thereto. 100 ml of toluene was added thereto and the mixture was refluxed at 120° C. for 0.5 hour. After completion of the reaction, the reaction mixture was allowed to cool to room temperature and washed with a saturated aqueous ammonium chloride solution (150 ml), followed by distilling off of the solvent under reduced pressure by an evaporator. The resulting residue was purified by silica gel column chromatography (developing solvent: hexane/ethyl acetate=4/1) to give 3.3 g of the desired compound (5-chloro-8-quinolylethyne) as a reddish brown solid (yield: 79%).

$^1$H-NMR (300 MHz, CDCl$_3$) δ: 3.63 (s, 1H), 7.55-7.61 (m, 2H), 7.87 (dd, 1H), 8.60 (dd, 1H), 9.10 (dd, 1H)

Reference Example 9

Synthesis of (5-chloro-8-quinolylethynyl)(triphenylphosphine)gold [Au(PPh$_3$) (5Cl-8QE)]

Under an argon atmosphere, Au(PPh$_3$)Cl (0.20 g, 0.40 mmol), 5-chloro-8-quinolylethyne (113 mg, 0.60 mmol) and amyl alcohol (8 ml) were added to a Schlenk tube (20 mL), and then sodium t-butoxide (40 mg, 0.42 mmol) was added thereto and the mixture was stirred at room temperature for 17 hours. After completion of the reaction, the resulting white precipitate was filtered and successively washed with amyl alcohol (5 ml×three times), hot water (5 ml×four times) and ethanol (5 ml×three times), followed by drying under vacuum to give 0.24 g of the desired compound as a pale yellow powder (yield: 91%).

$^1$H-NMR (400 MHz, CDCl$_3$) δ: 9.10 (dd, 1H), 8.55 (dd, 1H), 7.89 (d, 1H), 7.62-7.42 (m, 17H)

$^{31}$P-NMR (160 MHz, CDCl$_3$): 41.8

FAB-MS (M/Z): 646 (M+H)$^+$

Luminescence analysis: (CHCl$_3$, 77K, Ex250 nm) λ (nm): 390, 547

Elemental Analysis:

| | |
|---|---|
| Found | C: 53.82, H: 3.08, N: 2.26 |
| Theoretical | C: 53.93, H: 3.12, N: 2.17 |

Reference Example 10

Synthesis of (2-pyridylethynyl)(triphenylphosphine)gold [Au(PPh$_3$) (2PyE)]

Under an argon atmosphere, Au(PPh$_3$)Cl (297 mg, 0.60 mmol), 2-pyridylethyne (92.8 mg, 0.90 mmol) and ethanol (12 ml) were added to a 20 ml Schlenk tube, and then sodium ethoxide (250 μl, 0.63 mmol: 2.55 mol/l (liter) in ethanol solution) was added dropwise thereto and the mixture was stirred at room temperature for 19 hours. The reaction mixture was concentrated to approximately 1 ml, and then 40 ml of diethyl ether was added thereto. The resulting white precipitate was successively washed with water (12 ml×three times) and diethyl ether (6 ml×three times) and dried under vacuum to give 0.21 g of the desired compound as a white powder (yield: 64%).

$^1$H-NMR (400 MHz, CDCl$_3$) δ: 8.52 (m, 1H): 7.59-7.40 (m, 17H), 7.09 (m, 1H)

(FAB-MS) (M/Z): 562 (M+H)$^+$

Luminescence analysis: (CHCl$_3$, 77K, Ex250 nm) λ (nm): 416, 436, 443, 456

Elemental Analysis:

| | |
|---|---|
| Found | C: 51.58, H: 3.42, N: 2.47 |
| Theoretical | C: 53.49, H: 3.41, N: 2.50 |

Reference Example 11

Synthesis of (3-pyridylethynyl)(triphenylphosphine)gold [Au(PPh$_3$) (3PyE)]

Under an argon atmosphere, Au(PPh$_3$)Cl (297 mg, 0.60 mmol), 3-pyridylethyne (92.8 mg, 0.90 mmol) and ethanol (12 ml) were added to a 20 ml Schlenk tube, and then sodium ethoxide (250 μl, 0.63 mmol: 2.55 mol/l (liter) in ethanol solution) was added dropwise thereto and the mixture was stirred at room temperature for 19 hours. The precipitated white precipitate was filtered and successively washed with ethanol (12 ml×three times), water (12 ml×three times) and ethanol (6 ml×three times), followed by drying under vacuum to give 0.23 g of the desired compound as a white powder (yield: 69%).

$^1$H-NMR (400 MHz, CDCl$_3$) δ: 8.75-8.74 (m, 1H), 8.43-8.41 (m, 1H), 7.78-7.74 (m, 1H), 7.60-7.43 (m, 15H), 7.20-7.15 (m, 1H)

(FAB-MS) (M/Z): 562 (M+H)$^+$

Luminescence analysis: (CHCl$_3$, 77K, Ex250 nm) λ (nm): 422, 447

Elemental Analysis:

| | |
|---|---|
| Found | C: 53.20, H: 3.38, N: 2.50 |
| Theoretical | C: 53.49, H: 3.41, N: 2.50 |

Reference Example 12

Synthesis of 5-fluoro-2-pyridylethyne (First Step)

A 15 ml Schlenk tube was replaced with Ar and 880 mg (5 mmol) of 2-bromo-5-fluoropyridine, 58 mg (0.05 mmol) of tetrakis(triphenylphosphine)palladium, 5 mL of piperidine and 533 μl (5.5 mmol) of 2-methyl-3-butyn-2-ol were added thereto, followed by stirring of the mixture at 80° C. for 1 hour.

A saturated aqueous ammonium chloride solution was added to the reaction mixture, and then the mixture was extracted with diethyl ether. The extract was dried over magnesium sulfate and the solvent was distilled off under reduced pressure by an evaporator. The crude reaction product was purified by column chromatography (Hexane/AcOEt=5/1-3/1) using silica gel to give dimethylhydroxymethyl-5-fluoro-2-pyridylacetylene, i.e., the desired compound as a pale yellow crystal. Yield: 0.83 g (yield: 92%).

$^1$H-NMR (300 MHz, CDCl$_3$) δ: 8.43 (s, 1H), 7.30-7.45 (m, 2H), 2.37 (s, 1H), 1.83 (d, 6H)

[MS] EI (m/z): 179 (M$^+$−1), CI (m/z): 180 (MH$^+$)

(Second Step)

820 mg (4.58 mmol) of Dimethylhydroxymethyl-5-fluoro-2-pyridylacetylene and 192 mg (4.81 mmol) of NaOH (KISHIDA CHEMICAL CO., Ltd., 0.7 mm granular, 98%) were placed in a 50 mL two-neck flask equipped with a reflux condenser and the air inside the flask was replaced with Ar. 23 mL of toluene was added thereto and the mixture was refluxed at 120° C. for 0.25 hour. Toluene was added to the reaction mixture and the mixture was washed with a saturated aqueous ammonium chloride solution and dried over magnesium sulfate. The solvent was distilled off under reduced pressure at 90 mmHg/70° C. to give 5-fluoro-2-pyridylethyne as an orange-color liquid (0.35 g, yield: 63%).

$^1$H-NMR (300 MHz, CDCl$_3$) δ: 8.43 (s, 1H) 7.45-7.53 (m, 1H), 7.40-7.43 (m, 1H), 3.13 (d, 1H),

[MS] EI (m/z): 121 (M$^+$−1), CI (m/z): 122 (MH$^+$)

Reference Example 13

Synthesis of (5-fluoro-2-pyridylethynyl)(triphenylphosphine)gold [Au(PPh$_3$) (5F-2PyE)]

Under an argon atmosphere, Au(PPh$_3$)Cl (474 mg, 0.96 mmol), 5-fluoro-2-pyridylethyne (174 mg, 1.44 mmol) and ethanol (19 ml) were added to a 20 ml Schlenk tube, and then sodium ethoxide (395 μl, 1.01 mmol: 2.55 mol/L (liter) in ethanol solution) was added dropwise thereto and the mixture was stirred at room temperature for 17 hours. After completion of the reaction, the resulting white precipitate was filtered and successively washed with ethanol (12 ml×three times), water (12 ml×three times) and ethanol (6 ml×three times), followed by drying under vacuum to give 0.48 g of the desired compound as a yellow powder (yield: 86%).

$^1$H-NMR (400 MHz, CDCl$_3$) δ: 8.37 (d, 1H), 7.23-7.59 (m, 18H), (FAB-MS) (M/Z): 580 (M+H)$^+$

Luminescence analysis: (CHCl$_3$, 77K, Ex250 nm) λ (nm): 418, 446, 457

Elemental Analysis:

| Found | C: 51.51, H: 3.02, N: 2.47 |
|---|---|
| Theoretical | C: 51.83, H: 3.13, N: 2.42 |

Reference Example 14

Synthesis of 6-fluoro-3-pyridylethyne (First Step)
A 15 ml Schlenk tube was replaced with Ar and 880 mg (5 mmol) of 5-bromo-2-fluoropyridine, 58 mg (0.05 mmol) of tetrakis(triphenylphosphine)palladium, 5 mL of piperidine and 533 μL (5.5 mmol) of 2-methyl-3-butyn-2-ol were added thereto, followed by stirring of the mixture at 80° C. for 1 hour.
A saturated aqueous ammonium chloride solution was added to the reaction mixture, and then the mixture was extracted with diethyl ether. The extract was dried over magnesium sulfate and the solvent was distilled off under reduced pressure by an evaporator. The crude reaction product was purified by column chromatography (Hexane/AcOEt=4/1) using silica gel to give dimethylhydroxymethyl-5-fluoro-2-pyridylacetylene, i.e., the desired compound as a yellow crystal. Yield: 0.83 g (yield: 93%).
$^1$H-NMR (300 MHz, CDCl$_3$) δ: 8.28 (s, 1H), 7.77-7.84 (m, 1H), 6.88-6.92 (m, 1H), 2.27 (s, 1H), 1.62 (d, 6H)
[MS] EI (m/z): 179 (M$^+$−1), CI (m/z): 180 (MH$^+$)
(Second Step)
0.830 mg (4.63 mmol) of Dimethylhydroxymethyl-2-fluoro-5-pyridylacetylene and 195 mg (4.86 mmol) of NaOH (KISHIDA CHEMICAL CO., Ltd., 0.7 mm granular, 98%) were placed in a 50 mL two-neck flask equipped with a reflux condenser and the air inside the flask was replaced with Ar. 23 mL of toluene was added thereto and the mixture was refluxed at 120° C. for 1 hour. Toluene was added to the reaction mixture and the mixture was washed with a saturated aqueous ammonium chloride solution and dried over magnesium sulfate. The solvent was distilled off under reduced pressure at 95 mmHg/72° C. to give 6-fluoro-3-pyridylethyne as an orange-color liquid (0.18 g, yield: 32%).
$^1$H-NMR (300 MHz, CDCl$_3$) δ: 8.35 (s, 1H), 7.83-7.89 (m, 1H), 6.87-6.92 (m, 1H), 3.18 (d, 1H)
[MS] EI (m/z): 121 (M$^+$−1), CI (m/z): 122 (MH$^+$)

Reference Example 15

Synthesis of (6-fluoro-3-pyridylethynyl)(triphenylphosphine)gold [Au(PPh$_3$) (6F-3PyE)]

Under an argon atmosphere, Au(PPh$_3$)Cl (488 mg, 0.99 mmol), 6-fluoro-3-pyridylethyne (179 mg, 1.48 mmol) and ethanol (20 ml) were added to a 20 ml Schlenk tube, and then sodium ethoxide (408 μl, 1.04 mmol: 2.55 mol/L (liter) in ethanol solution) was added dropwise thereto and the mixture was stirred at room temperature for 17 hours. After completion of the reaction, the resulting white precipitate was filtered and successively washed with ethanol (12 ml×three times), water (12 ml×three times) and ethanol (6 ml×three times), followed by drying under vacuum to give 0.42 g of the desired compound as a yellow powder (yield: 73%).
$^1$H-NMR (400 MHz, CDCl$_3$) δ: 8.35 (s, 1H), 7.81-7.87 (m, 1H), 6.80-6.84 (m, 1H)
(FAB-MS) (M/Z): 580 (M+H)$^+$
Luminescence analysis: (CHCl$_3$, 77K, Ex250 nm) λ (nm): 413, 433, 442, 452

Elemental Analysis:

| Found | C: 51.76, H: 3.05, N: 2.51 |
|---|---|
| Theoretical | C: 51.83, H: 3.13, N: 2.42 |

Reference Example 16

Synthesis of (4-phenylphenylethynyl)(triphenylphosphine)gold [Au (PPh$_3$) (4Ph-PE)]

Under an argon atmosphere, Au(PPh$_3$)Cl (1.0 g, 2.02 mmol), 4-phenylphenylethyne (540 mg, 3.03 mmol) and ethanol (35 ml) were added to a 20 ml Schlenk tube, and then sodium ethoxide (0.83 ml, 2.12 mmol: 2.55 mol/l (liter) in ethanol solution) was added dropwise thereto and the mixture was heated under reflux for 1.5 hours. The reaction mixture was cooled to room temperature and the resulting white precipitate was filtered and successively washed with ethanol (20 ml×three times), water (20 ml×three times) and ethanol (20 ml×three times), followed by drying under vacuum to give 1.26 g of the desired compound as a white powder (yield: 98%).
$^1$H-NMR (400 MHz, CDCl$_3$) δ: 7.60-7.40 (m, 23H), 7.34-7.29 (m, 1H)
(FAB-MS) (M/Z): 637 (M+H)$^+$
Elemental Analysis:

| Found | C: 59.96, H: 3.86 |
|---|---|
| Theoretical | C: 60.39, H: 3.80 |

Reference Example 17

Synthesis of (4-nitrophenylethynyl)(triphenylphosphine)gold [Au(PPh$_3$) (4NO$_2$—PE)]

Under an argon atmosphere, Au(PPh$_3$)Cl (1.0 g, 2.02 mmol), 4-nitrophenylethyne (446 mg, 3.03 mmol) and ethanol (35 ml) were added to a 20 ml Schlenk tube, and then sodium ethoxide (0.83 ml, 2.12 mmol: 2.55 mol/l (liter) in ethanol solution) was added dropwise thereto and the mixture was heated under reflux for 1.5 hours. The reaction mixture was cooled to room temperature and the resulting white precipitate was filtered and successively washed with ethanol (20 ml×three times), water (20 ml×three times) and ethanol (20 ml×three times), followed by drying under vacuum to give 0.95 g of the desired compound as a white powder (yield: 78%).
$^1$H-NMR (400 MHz, CDCl$_3$) δ: 8.14-8.10 (m, 2H), 7.62-7.44 (m, 17H)
(FAB-MS) (M/Z): 606 (M+H)$^+$
Elemental Analysis:

| Found | C: 51.39, H: 3.10, N: 2.31 |
|---|---|
| Theoretical | C: 51.58, H: 3.16, N: 2.31 |

Reference Example 18

Synthesis of (2,4-difluorophenylethynyl)(triphenylphosphine)gold [Au(PPh$_3$) (2,4F$_2$—PE)]

Under an argon atmosphere, Au(PPh$_3$)Cl (1.0 g, 2.02 mmol), 2,4-difluorophenylethyne (431 mg, 3.03 mmol) and ethanol (35 ml) were added to a 20 ml Schlenk tube, and then sodium ethoxide (0.83 ml, 2.12 mmol: 2.55 mol/l (liter) in ethanol solution) was added dropwise thereto and the mixture was stirred at room temperature for 23 hours. The reaction mixture was concentrated and the resulting white solid was successively washed with diethyl ether (20 ml×three times), water (20 ml×three times) and diethyl ether (20 ml×three times), followed by drying under vacuum to give 1.04 g of the desired compound as a white powder (yield: 86%).

$^1$H-NMR (400 MHz, CDCl$_3$) δ: 7.61-7.42 (m, 16H), 6.82-6.74 (m, 2H)

(FAB-MS) (M/Z): 597 (M+H)$^+$

Elemental Analysis:

| | |
|---|---|
| Found | C: 52.04, H: 3.04 |
| Theoretical | C: 52.36, H: 3.04 |

Reference Example 19

Synthesis of 1-naphthylethyne (First Step)

A 30 mL Schlenk tube was replaced with Ar and 1-bromonaphthalene (1.00 g, 96 mass % article, 4.64 mmol), tetrakis(triphenylphosphine)palladium (53.6 mg, 0.0464 mmol), 5.60 mL of piperidine and 2-methyl-3-butyn-2-ol (597 mg, 98 mass % article, 6.94 mmol) were added thereto, followed by stirring of the mixture at 80° C. for 3 hours. The reaction mixture was cooled to room temperature, and then a saturated aqueous ammonium chloride solution was added thereto and the mixture was extracted with diethyl ether. The extract was dried over magnesium sulfate and the solvent was distilled off under reduced pressure by an evaporator. The crude reaction product was purified by column chromatography (Hexane/AcOEt=100/0→1/5) using silica gel to give 898 mg of dimethylhydroxymethyl-1-naphthylacetylene as a yellow liquid (yield: 88.4%).

$^1$H-NMR (300 MHz, CDCl$_3$) δ: 8.30-8.27 (m, 1H), 7.85-7.80 (m, 2H), 7.66-7.63 (m, 1H), 7.48 (m, 2H), 7.43-7.38 (m, 1H), 2.15 (brs, 1H), 1.73 (s, 6H)

[MS] EI (m/z): 209 (M$^+$), CI (m/z): 210 (MH$^+$)

(Second Step)

Dimethylhydroxymethyl-1-naphthylacetylene (898 mg, 4.27 mmol) and NaOH (239 mg, KISHIDA CHEMICAL CO., Ltd., 0.7 mm granular, 98% article, 5.98 mmol) were placed in a 30 mL two-neck flask equipped with a reflux condenser and the air inside the flask was replaced with Ar. 20 mL of toluene was added thereto and the mixture was refluxed at 120° C. for 30 minutes. Diethyl ether was added to the reaction mixture and the mixture was washed with a saturated aqueous ammonium chloride solution and dried over magnesium sulfate. The solvent was distilled off under reduced pressure by an evaporator. The crude reaction product was purified by column chromatography (Hexane/AcOEt=100/0→1/10) using silica gel to give 577 mg of the desired compound as a yellow solid (yield: 88.8%).

$^1$H-NMR (300 MHz, CDCl$_3$) δ: 8.38-8.34 (m, 1H), 7.86-7.75 (m, 2H), 7.61-7.59 (m, 1H), 7.58-7.42 (m, 2H), 7.41-7.38 (m, 1H), 3.42 (s, 1H)

[MS] EI (m/z): 151 (M$^+$), CI (m/z): 152 (MH$^+$)

Reference Example 20

Synthesis of (1-naphthylethynyl)(triphenylphosphine)gold [Au(PPh$_3$) (1NpE)]

Under an argon atmosphere, Au(PPh$_3$)Cl (650 mg, 1.31 mmol), 1-naphthylethyne (300 mg, 1.97 mmol) and 26.0 mL of ethanol were added to a 30 ml Schlenk tube, and then sodium ethoxide (800 μl, 2.07 mmol: 2.55 mol/L (liter) in ethanol solution) was added dropwise thereto and the mixture was stirred at room temperature for 15 hours. After completion of the reaction, the resulting white precipitate was filtered and successively washed with 20 mL of ethanol three times, 20 mL of water four times and 20 mL of ethanol three times, followed by drying under vacuum to give 789 mg of the desired compound as a pale yellow powder (yield: 65.5%).

$^1$H-NMR (300 MHz, CDCl$_3$) δ: 8.65-8.63 (m, 1H), 7.82-7.70 (m, 2H), 7.63-7.37 (m, 19H)

[MS] FAB (m/z): 611 (MH$^+$)

Elemental Analysis:

| | |
|---|---|
| Found | C: 58.74, H: 3.64 |
| Theoretical | C: 59.03, H: 3.63 |

Reference Example 21

Synthesis of 4-fluoro-1-naphthylethyne (First Step)

A 30 mL Schlenk tube was replaced with Ar and 1-bromo-4-fluoronaphthalene (2.00 g, 97 mass % article, 8.62 mmol), tetrakis(triphenylphosphine)palladium (99.6 mg, 0.0862 mmol), 10.3 mL of piperidine and 2-methyl-3-butyn-2-ol (1.11 g, 98 mass % article, 12.9 mmol) were added thereto, followed by stirring of the mixture at 80° C. for 3 hours. The reaction mixture was cooled to room temperature, and then a saturated aqueous ammonium chloride solution was added thereto and the mixture was extracted with diethyl ether. The extract was dried over magnesium sulfate and the solvent was distilled off under reduced pressure by an evaporator. The crude reaction product was purified by column chromatography (Hexane/AcOEt=100/0→1/5) using silica gel to give 1.88 g of dimethylhydroxymethyl-4-fluoro-1-naphthylacetylene as a yellow liquid (yield: 95.7%).

$^1$H-NMR (300 MHz, CDCl$_3$) δ: 8.28-8.25 (m, 1H), 8.12-8.09 (m, 1H), 7.65-7.54 (m, 3H), 7.11-7.05 (m, 1H), 2.19 (brs, 1H), 1.72 (s, 6H)

[MS] EI (m/z): 228 (M$^+$), CI (m/z): 229 (MH$^+$)

(Second Step)

Dimethylhydroxymethyl-4-fluoro-1-naphthylacetylene (1.88 g, 8.23 mmol) and NaOH (396 mg, KISHIDA CHEMICAL CO., Ltd., 0.7 mm granular, 98% article, 9.90 mmol) were placed in a 30 mL two-neck flask equipped with a reflux condenser and the air inside the flask was replaced with Ar. 20 mL of toluene was added thereto and the mixture was refluxed at 120° C. for 30 minutes. Diethyl ether was added to the reaction mixture and the mixture was washed with a saturated aqueous ammonium chloride solution and dried over magnesium sulfate. The solvent was distilled off under reduced pressure by an evaporator. The crude reaction product was purified by column chromatography (Hexane/AcOEt=100/0→1/10) using silica gel to give 946 mg of the desired compound as a yellow solid (yield: 67.5%).

$^1$H-NMR (300 MHz, CDCl$_3$) δ: 8.37-8.33 (m, 1H), 8.14-8.11 (m, 1H), 7.70-7.56 (m, 3H), 7.13-7.10 (m, 1H), 3.43 (s, 1H)

[MS] EI (m/z): 170 (M$^+$), CI (m/z): 171 (MH$^+$)

Reference Example 22

Synthesis of (4-fluoro-1-naphthylethynyl)(triphenylphosphine)gold [Au(PPh$_3$) (4F-1NpE)]

Under an argon atmosphere, Au(PPh$_3$)Cl (582 mg, 1.18 mmol), 4-fluoro-1-naphthylethyne (300 mg, 1.77 mmol) and 23.0 mL of ethanol were added to a 30 ml Schlenk tube, and then sodium ethoxide (725 μl, 1.85 mmol: 2.55 mol/l (liter) in ethanol solution) was added dropwise thereto and the mixture was stirred at room temperature for 15 hours. After completion of the reaction, the resulting white precipitate was filtered and successively washed with 20.0 mL of ethanol three times, 20.0 mL of water three times and 20.0 mL of ethanol three times, followed by drying under vacuum to give 647 mg of the desired compound as a pale yellow powder (yield: 58.3%).

$^1$H-NMR (300 MHz, CDCl$_3$) δ: 8.64-8.60 (m, 1H), 8.08-8.05 (m, 1H), 7.67-7.44 (m, 18H), 7.08-7.18 (m, 1H)

[MS] FAB (m/z): 629 (MH$^+$)

Elemental Analysis:

| Found | C: 57.00, H: 3.35 |
|---|---|
| Theoretical | C: 57.34, H: 3.37 |

Reference Example 23

Synthesis of 9-anthrylethyne (First Step)

A 20 mL Schlenk tube was replaced with Ar and 1.8 g (7 mmol) of 9-bromoanthracene, 80.9 mg (0.07 mmol) of tetrakis(triphenylphosphine)palladium, 7 mL of piperidine and 46 μL (7.7 mmol) of 2-methyl-3-butyn-2-ol were added thereto, followed by stirring of the mixture at 100° C. for 5 hours.

A saturated aqueous ammonium chloride solution was added to the reaction mixture, and then the mixture was extracted with diethyl ether. The extract was dried over magnesium sulfate and the solvent was distilled off under reduced pressure by an evaporator. The resulting crude reaction product was dissolved in 70 ml of hexane at 70° C. and the insolubles were filtered off. The filtrate was cooled to give dimethylhydroxymethyl-9-anthrylacetylene, i.e., the desired compound as a yellow crystal. Yield: 1.66 g (yield: 91%).

$^1$H-NMR (300 MHz, CDCl$_3$) δ: 8.41-8.51 (m, 3H), 7.98-8.01 (m, 2H), 7.46-7.59 (m, 4H), 2.24 (s, 1H), 1.83 (s, 6H)

[MS] EI (m/z): 260 (M$^+$−1), CI (m/z): 261 (MH$^+$)

(Second Step)

1.3 g (5 mmol) of Dimethylhydroxymethyl-9-anthrylacetylene and 210 mg (5.25 mmol) of NaOH (KISHIDA CHEMICAL CO., Ltd., 0.7 mm granular, 98%) were placed in a 50 mL two-neck flask equipped with a reflux condenser and the air inside the flask was replaced with Ar. 25 mL of toluene was added thereto and the mixture was refluxed at 120° C. for 0.75 hour. Toluene was added to the reaction mixture and the mixture was washed with a saturated aqueous ammonium chloride solution and dried over magnesium sulfate. The solvent was distilled off under reduced pressure by an evaporator. The crude reaction product was purified by column chromatography (Hexane/AcOEt=10/1) using silica gel to give 9-anthryl ethyne as an orange-color solid (0.31 g, yield: 31%).

$^1$H-NMR (300 MHz, CDCl$_3$) δ: 8.40-8.59 (m, 3H), 7.95-8.06 (m, 2H), 7.47-7.67 (m, 4H), 3.97 (s, 1H)

[MS] EI (m/z): 202 (M$^+$−1), CI (m/z): 203 (MH$^+$)

Reference Example 24

Synthesis of (9-anthrylethynyl)(triphenylphosphine)gold [Au(PPh$_3$) (9AntE)]

Under an argon atmosphere, Au(PPh$_3$)Cl (445 mg, 0.90 mmol), 9-anthrylethyne (273 mg, 1.35 mmol) and ethanol (18 ml) were added to a 20 ml Schlenk tube, and then sodium ethoxide (371 μl, 0.945 mmol: 2.55 mol/L (liter) in ethanol solution) was added dropwise thereto and the mixture was stirred at room temperature for 18.5 hours. After completion of the reaction, the resulting white precipitate was filtered and successively washed with ethanol (12 ml×three times), water (12 ml×three times) and ethanol (6 ml×three times), followed by drying under vacuum to give 0.57 g of the desired compound as a yellow powder (yield: 96%).

$^1$H-NMR (400 MHz, CDCl$_3$) δ: 8.56-8.89 (m, 2H), 8.56-8.89 (m, 2H), 8.30 (s, 1H), 7.94-7.97 (m, 2H), 7.43-7.67 (m, 19H)

(FAB-MS) (M/Z): 660 (M+H)$^+$

Luminescence analysis: (CHCl$_3$, 77K, Ex250 nm) λ (nm): 435, 450, 477

Elemental Analysis:

| Found | C: 61.73, H: 3.58 |
|---|---|
| Theoretical | C: 61.83, H: 3.66 |

Reference Example 25

Synthesis of 9-phenanethrylethyne (First Step)

A 20 mL Schlenk tube was replaced with Ar and 1.8 g (7 mmol) of 9-bromophenanthrene, 80.9 mg (0.07 mmol) of tetrakis(triphenylphosphine)palladium, 7 mL of piperidine and 746 mL (7.7 mmol) of 2-methyl-3-butyn-2-ol were added thereto, followed by stirring of the mixture at 100° C. for 3 hours.

A saturated aqueous ammonium chloride solution was added to the reaction mixture, and then the mixture was extracted with diethyl ether. The extract was dried over magnesium sulfate and the solvent was distilled off under reduced pressure by an evaporator. The resulting crude reaction product was purified by column chromatography (Hexane/AcOEt=5/1) using silica gel to give dimethylhydroxymethyl-9-phenanethrylacetylene, i.e., the desired compound as a viscous yellow liquid. Yield: 1.76 g (yield: 97%).

$^1$H-NMR (300 MHz, CDCl$_3$) δ: 8.59-8.67 (m, 2H), 8.35-8.40 (m, 1H), 7.94 (s, 1H), 7.81 (d, 1H), 7.53-7.79 (m, 4H), 2.31 (s, 1H), 1.75 (s, 6H)

[MS] EI (m/z): 260 (M$^+$−1), CI (m/z): 261 (MH$^+$)

(Second Step)

1.75 g (6.7 mmol) of Dimethylhydroxymethyl-9-phenanethrylacetylene and 282 mg (7.1 mmol) of NaOH (KISHIDA CHEMICAL CO., Ltd., 0.7 mm granular, 98%) were placed in a 50 mL two-neck flask equipped with a reflux condenser and the air inside the flask was replaced with Ar. 34 mL of toluene was added thereto and the mixture was refluxed at 120° C. for 1.5 hours. Toluene was added to the reaction mixture and the mixture was washed with a saturated aqueous ammonium chloride solution and dried over magnesium sulfate. The solvent was distilled off under reduced pressure by an evaporator. The crude reaction product was purified by column chromatography (Hexane/AcOEt=15/1) using silica gel. The resulting orange-color solid was dissolved in 10 ml of hexane at 60° C., the insolubles were filtered off, and then the filtrate was cooled to give 9-phenanethrylethyne as a yellow solid (0.61 g, yield: 45%).

$^1$H-NMR (300 MHz, CDCl$_3$) δ: 8.64-8.71 (m, 2H), 8.43-8.50 (m, 1H), 8.02 (s, 3H), 7.83-7.86 (m, 1H), 7.57-7.73 (m, 3H), 3.47 (s, 1H)

[MS] EI (m/z): 202 (M$^+$–1), CI (m/z): 203 (MH$^+$)

Reference Example 26

Synthesis of (9-phenanethrylethynyl)(triphenylphosphine)gold [Au(PPh$_3$) (9-PhenE)]

Under an argon atmosphere, Au(PPh$_3$)Cl (445 mg, 0.90 mmol), 9-anthnylethyne (273 mg, 1.35 mmol) and ethanol (18 ml) were added to a 20 ml Schlenk tube, and then sodium ethoxide (371 μl, 0.945 mmol: 2.55 mol/L (liter) in ethanol solution) was added dropwise thereto and the mixture was stirred at room temperature for 17 hours. After completion of the reaction, the resulting white precipitate was filtered and successively washed with ethanol (12 ml×three times), water (12 ml×three times) and ethanol (6 ml×three times), followed by drying under vacuum to give 0.59 g of the desired compound as a pale yellow powder (yield: 99%).

$^1$H-NMR (400 MHz, CDCl$_3$) δ: 8.76-8.79 (d, 1H), 8.61-8.67 (m, 2H), 8.05 (s, 1H), 7.67-7.82 (m, 1H), 7.45-7.67 (m, 19H)

(FAB-MS) (M/Z): 661 (M+H)$^+$

Luminescence analysis: (CHCl$_3$, 77K, Ex250 nm) λ (nm): 380, 522, 532, 568

Elemental Analysis:

| | |
|---|---|
| Found | C: 61.64, H: 3.53 |
| Theoretical | C: 61.83, H: 3.66 |

Reference Example 27

Synthesis of 1-pyrenylethyne (First Step)

A 15 mL Schlenk tube was replaced with Ar and 1.97 g (7 mmol) of 1-bromopyrene, 80.9 mg (0.07 mmol) of tetrakis(triphenylphosphine)palladium, 7 mL of piperidine and 746 μL (7.7 mmol) of 2-methyl-3-butyn-2-ol were added thereto, followed by stirring of the mixture at 100° C. for 3 hours. A saturated aqueous ammonium chloride solution was added to the reaction mixture, and then the mixture was extracted with diethyl ether. The extract was dried over magnesium sulfate and the solvent was distilled off under reduced pressure by an evaporator. The resulting crude reaction product was dissolved in 180 ml of hexane at 70° C. and the insolubles were filtered off. The filtrate was cooled to give dimethylhydroxymethyl-9-pyrenylacetylene, i.e., the desired compound as a yellow crystal. Yield: 1.53 g (yield: 77%).

$^1$H-NMR (300 MHz, CDCl$_3$) δ: 8.48-8.57 (m, 1H), 7.92-8.26 (m, 8H), 2.24 (s, 1H), 1.80 (s, 6H)

[MS] EI (m/z): 284 (M$^+$–1), CI (m/z): 285 (MH$^+$)

(Second Step)

1.5 g (5.28 mmol) of Dimethylhydroxymethyl-9-pyrenylacetylene and 222 mg (5.54 mmol) of NaOH (KISHIDA CHEMICAL CO., Ltd., 0.7 mm granular, 98%) were placed in a 50 mL two-neck flask equipped with a reflux condenser and the air inside the flask was replaced with Ar. 26 mL of toluene was added thereto and the mixture was refluxed at 120° C. for 0.67 hour. Toluene was added to the reaction mixture and the mixture was washed with a saturated aqueous ammonium chloride solution and dried over magnesium sulfate. The solvent was distilled off under reduced pressure by an evaporator. The crude reaction product was purified by column chromatography (Hexane/AcOEt=10/1) using silica gel to give 1-pyrenylethyne as an orange-color solid (0.69 g, yield: 58%).

$^1$H-NMR (300 MHz, CDCl$_3$) δ: 8.57 (d, 1H), 7.24-8.27 (m, 8H), 3.62 (s, 1H)

[MS] EI (m/z): 226 (M$^+$–1), CI (m/z): 227 (MH$^+$)

Reference Example 28

Synthesis of (1-pyrenylethynyl)(triphenylphosphine)gold [Au(PPh$_3$) (1-PyrenE)]

Under an argon atmosphere, Au(PPh$_3$)Cl (445 mg, 0.90 mmol), 1-pyrenylethyne (305 mg, 1.35 mmol) and ethanol (18 ml) were added to a 20 ml Schlenk tube, and then sodium ethoxide (371 μl, 0.945 mmol: 2.55 mol/L (liter) in ethanol solution) was added dropwise thereto and the mixture was stirred at room temperature for 17 hours. After completion of the reaction, the resulting white precipitate was filtered and successively washed with ethanol (12 ml×three times), water (12 ml×three times) and ethanol (6 ml×three times), followed by drying under vacuum to give 0.62 g of the desired compound as a yellow powder (yield: 99%).

$^1$H-NMR (400 MHz, CDCl$_3$) δ: 8.87 (d, 1H), 7.95-8.23 (m, 8H), 7.46-7.66 (m, 15H)

(FAB-MS) (M/Z): 684 (M+H)$^+$

Luminescence analysis: (CHCl$_3$, 77K, Ex250 nm) λ (nm): 319, 404

Elemental Analysis:

| | |
|---|---|
| Found | C: 62.84, H: 3.51 |
| Theoretical | C: 63.17, H: 3.53 |

Reference Example 29

Synthesis of 2-fluorenylethyne (First Step)

A 30 mL Schlenk tube was replaced with Ar and 3.68 g (15 mmol) of 2-bromofluorene, 173 mg (0.15 mmol) of tetrakis(triphenylphosphine)palladium, 15 mL of piperidine and 1.6 mL (16.5 mmol) of 2-methyl-3-butyn-2-ol were added thereto, followed by stirring of the mixture at 100° C. for 3 hours.

A saturated aqueous ammonium chloride solution was added to the reaction mixture, and then the mixture was extracted with diethyl ether. The extract was dried over magnesium sulfate and the solvent was distilled off under reduced pressure by an evaporator. The resulting crude reaction product was dissolved in 250 ml of hexane at 70° C. and then the insolubles were filtered off. The filtrate was cooled to give dimethylhydroxymethyl-2-fluorenylacetylene, i.e., the desired compound as a white crystal. Yield: 2.91 g (yield: 78%).

$^1$H-NMR (300 MHz, CDCl$_3$) δ: 7.25-8.14 (m, 7H), 3.87 (s, 2H), 2.07 (s, 1H), 1.64 (s, 6H)

[MS] EI (m/z): 248 (M$^+$−1), CI (m/z): 249 (MH$^+$)

(Second Step)

1.74 g (7 mmol) of Dimethylhydroxymethyl-2-fluorenylacetylene and 294 mg (7.35 mmol) of NaOH (KISHIDA CHEMICAL CO., Ltd., 0.7 mm granular, 98%) were placed in a 100 mL two-neck flask equipped with a reflux condenser and the air inside the flask was replaced with Ar. 35 mL of toluene was added thereto and the mixture was refluxed at 120° C. for 1 hour. Toluene was added to the reaction mixture and the mixture was washed with a saturated aqueous ammonium chloride solution and dried over magnesium sulfate. The solvent was distilled off under reduced pressure by an evaporator. The resulting crude reaction product was dissolved in 40 ml of hexane at 70° C. and then the insolubles were filtered off. The filtrate was cooled to give 2-fluorenylethyne, i.e., the desired compound as a yellow solid (1.12 g, yield: 84%).

$^1$H-NMR (300 MHz, CDCl$_3$) δ: 7.25-7.79 (m, 7H), 3.88 (s, 2H), 3.11 (s, 1H)

[MS] EI (m/z): 190 (M$^+$−1), CI (m/z): 191 (MH$^+$)

Reference Example 30

Synthesis of
(2-fluorenylethynyl)(triphenylphosphine)gold
[Au(PPh$_3$) (2-FluorE)]

Under an argon atmosphere, Au(PPh$_3$)Cl (445 mg, 0.90 mmol), 2-fluorenylethyne (257 mg, 1.35 mmol) and ethanol (18 ml) were added to a 30 ml Schlenk tube, and then sodium ethoxide (371 μl, 0.945 mmol: 2.55 mol/L (liter) in ethanol solution) was added dropwise thereto and the mixture was stirred at room temperature for 18 hours. After completion of the reaction, the resulting white precipitate was filtered and successively washed with ethanol (12 ml×three times), water (12 ml×three times) and ethanol (6 ml×three times), followed by drying under vacuum to give 0.58 g of the desired compound as a yellow powder (yield: 99%).

$^1$H-NMR (400 MHz, CDCl$_3$) δ: 7.22-7.74 (m, 22H), 3.86 (s, 2H), (FAB-MS) (M/Z): 649 (M+H)$^+$

Luminescence analysis: (CHCl$_3$, 77K, Ex250 nm) λ (nm): 479, 498, 508, 518

Elemental Analysis:

| | |
|---|---|
| Found | C: 61.34, H: 3.83 |
| Theoretical | C: 61.12, H: 3.73 |

Reference Example 31

Synthesis of 5-fluoro-7-propyl-8-quinolylethyne (First Step)

After a 100 mL three-neck flask equipped with a magnetic stirrer, a reflux condenser, a thermometer and a dropping funnel was replaced with Ar, 5 mL of DMF and NaH (0.88 g, 60 mass % article, 22.0 mmol) were placed therein and the temperature of the mixture was cooled to 0° C. or lower in an ice bath, followed by stirring of the mixture. 5-Fluoro-8-quinolinol (3.42 g, 21.0 mmol) dissolved in 30.0 mL of DMF was added dropwise to this over 1 hour. After the mixture was stirred at the same temperature for 30 minutes, allyl bromide (2.54 g, 21.0 mmol) was added dropwise thereto. Further, the mixture was stirred at the same temperature for 30 minutes, and then the internal temperature was slowly raised to 150° C. and the mixture was heated and stirred for 2 hours. This was cooled to room temperature, and then the reaction mixture was poured into water and the mixture was extracted with ethyl acetate. Then, ethyl acetate was removed under reduced pressure and the resulting crude reaction product was purified by column chromatography (Hexane/AcOEt=100/0→1/1) using silica gel, followed by drying under reduced pressure to give 4.10 g of 7-allyl-5-fluoro-8-quinolinol as a white solid (yield: 96.0%).

$^1$H-NMR (300 MHz, CDCl$_3$) δ: 8.81-8.79 (m, 1H), 8.47-8.43 (m, 1H), 8.01 (brs, 1H), 7.47-7.43 (m, 1H), 7.26-7.05 (m, 1H), 6.11-5.97 (m, 1H), 5.19-5.10 (m, 2H), 3.63-3.60 (m, 2H)

[MS] EI (m/z): 203 (M$^+$), CI (m/z): 204 (MH$^+$)

(Second Step)

After a 100 mL three-neck flask equipped with a magnetic stirrer, a reflux condenser and a thermometer was replaced with Ar, 40.0 mL of methanol, 5 wt % Pd/C (0.40 g) and 7-allyl-5-fluoro-8-quinolinol (4.09 g) were thrown thereto and the mixture was stirred under slight pressurization of hydrogen. After replaced with Ar, the mixture was filtered to remove Pd/C and the filtrate was concentrated to give 3.98 g of 5-fluoro-7-propyl-8-quinolinol as a pale purple solid (yield: 96.0%).

$^1$H-NMR (300 MHz, CDCl$_3$) δ: 8.85-8.82 (m, 1H), 8.41-8.37 (m, 1H), 8.02 (brs, 1H), 7.94-7.44 (m, 1H), 7.10 (d, 1H), 2.88-2.83 (m, 2H), 1.83-1.71 (m, 2H), 1.03 (t, 3H)

[MS] EI (m/z): 205 (M$^+$), CI (m/z): 206 (MH$^+$)

(Third Step)

After a 250 mL three-neck flask equipped with a magnetic stirrer, a reflux condenser, a thermometer and a dropping funnel was replaced with Ar, 5-fluoro-7-propyl-8-quinolinol (3.98 g, 19.4 mmol), 20.0 mL of methylene chloride and triethylamine (3.53 mL, 25.2 mmol) were thrown thereto and the internal temperature was cooled to 0° C. under stirring in an ice bath, followed by dropwise addition of trifluoromethanesulfonic anhydride (3.60 mL, 21.3 mmol). After completion of the dropwise addition, the reaction mixture varied to approximately black was stirred for 1 hour while maintaining the reaction temperature to 0° C. After completion of the reaction, 100 mL of water and 100 mL of diethyl ether were added to the reaction mixture to separate the solution and the resulting organic layer was washed with 1 mol/L of hydrochloric acid (60 mL×twice) and water (60 mL×once) in the order and dried over 25, magnesium sulfate. After filtration, diethyl ether was distilled off from the filtrate under reduced pressure and the resulting residue was dissolved in 100 mL of hexane at 70° C. The insolubles were filtered off, and then the filtrate was cooled to give 4.19 g of 5-fluoro-7-propyl-8-trifluoromethanesulfonyloxyquinoline as a brownish white crystal (yield: 64.0%).

$^1$H-NMR (300 MHz, CDCl$_3$) δ: 9.05-9.00 (m, 1H), 8.42-8.38 (m, 1H), 7.55-7.50 (m, 1H), 7.15 (d, 1H), 2.91-2.85 (m, 2H), 1.81-1.69 (m, 2H), 1.02 (t, 3H)

[MS] EI (m/z): 337 (M$^+$), CI (m/z): 338 (MH$^+$)

(Fourth Step)

A 25 mL Schlenk tube was replaced with Ar and 5-fluoro-7-propyl-8-trifluoromethanesulfonyloxyquinoline (1.00 g, 2.97 mmol), tetrakis(triphenylphosphine)palladium (171.3 mg, 0.148 mmol), 3.55 mL of piperidine and 2-methyl-3-butyn-2-ol (381 mg, 98 mass % article, 3.75 mmol) were added thereto and the mixture was stirred at 80° C. for 3 hours. The reaction mixture was cooled to room temperature, and then a saturated aqueous ammonium chloride solution was added thereto and the mixture was extracted with diethyl ether. The extract was dried over magnesium sulfate and the solvent was distilled off under reduced pressure by an evaporator. The crude reaction product was purified by column chromatography (Hexane/AcOEt=100/0→1/5) using silica gel to give 390 mg of dimethylhydroxymethyl-5-fluoro-7-propyl-8-quinolylacetylene as a yellowish brown solid (yield: 48.4%).

$^1$H-NMR (300 MHz, CDCl$_3$) δ: 9.05-9.02 (m, 1H), 8.39-8.35 (m, 1H), 7.43-7.39 (m, 1H), 7.11 (d, 1H), 2.99-2.94 (m, 2H), 2.28 (brs, 1H), 1.79-1.74 (m, 2H), 1.72 (s, 6H), 1.01 (t, 3H)

[MS] EI (m/z): 271 (M$^+$), CI (m/z): 272 (MH$^+$)

(Fifth Step)

Dimethylhydroxymethyl-5-fluoro-7-propyl-8-quinolylacetylene (390 mg, 1.44 mmol) and NaOH (88.0 mg, KISHIDA CHEMICAL CO., Ltd., 0.7 mm granular, 98%) were placed in a 30 mL Schlenk tube equipped with a reflux condenser and the air inside the flask was replaced with Ar. 5.0 mL of toluene was added thereto and the mixture was refluxed at 120° C. for 30 minutes. Diethyl ether was added to the reaction mixture and the mixture was washed with a saturated aqueous ammonium chloride solution and dried over magnesium sulfate. The solvent was distilled off under reduced pressure by an evaporator. The crude reaction product was purified by column chromatography (Hexane/AcOEt=100/0→1/10) using silica gel to give 206 mg of 5-fluoro-7-propyl-8-quinolylethyne as a yellow solid (yield: 66.6%).

$^1$H-NMR (300 MHz, CDCl$_3$) δ: 9.09-9.07 (m, 1H), 8.42-8.38 (m, 1H), 7.48-7.44 (m, 1H), 7.14 (d, 1H), 3.76 (s, 1H), 3.07-3.02 (m, 2H), 1.84-1.72 (m, 2H), 1.02 (t, 3H)

[MS] EI (m/z): 213 (M$^+$), CI (m/z): 214 (MH$^+$)

Reference Example 32

Synthesis of (5-fluoro-7-propyl-8-quinolylethynyl)(triphenylphosphine)gold [Au(PPh$_3$) (5F7Pr-8QE)]

Under an argon atmosphere, Au(PPh$_3$)Cl (107 mg, 0.216 mmol), 8-ethynyl-5-fluoro-7-propyl-quinoline (69.0 mg, 0.323 mmol) and 5.0 mL of tert-amyl alcohol were added to a 30 mL Schlenk tube, and then sodium tert-butoxide (22.8 mg, 0.227 mmol) was added thereto and the mixture was stirred at room temperature for 15 hours. After completion of the reaction, the resulting white precipitate was filtered and successively washed with 5.0 mL of amyl alcohol, 10.0 mL of water and 20.0 mL of ethanol, followed by drying under vacuum to give 60.0 mg of the desired compound as a pale yellow powder (yield: 41.3%).

$^1$H-NMR (300 MHz, CDCl$_3$) δ: 9.08-9.06 (m, 1H), 8.35-8.32 (m, 1H), 7.62-7.35 (m, 16H), 7.09 (d, 1H), 3.21-3.15 (m, 2H), 1.87-1.79 (m, 2H), 1.05 (t, 3H)

[MS] FAB (m/z): 672 (MH$^+$)

Luminescence analysis: (CHCl$_3$, 77K, Ex250 nm) λ (nm): 360, 399, 541

Elemental Analysis:

| | |
|---|---|
| Found | C: 54.56, H: 3.47, N: 1.71 |
| Theoretical | C: 57.24, H: 3.90, N: 2.09 |

Reference Example 33

Synthesis of (5-fluoro-3-butyl-8-quinolylethynyl)(triphenylphosphine)gold [Au(PPh$_3$) (5F3Bu-8QE)]

(First Step)

2-Bromo-5-fluoro-aniline (5.00 g, 95 mass % article, 25.0 mmol), m-nitrobenzenesulfonic acid (2.65 g, 13.1 mmol), 20.0 mL of 85 wt % aqueous phosphoric acid solution and ferrous sulfate heptahydrate (69.5 mg, 0.250 mmol) were placed in a 100 mL three-neck flask equipped with a magnetic stirrer, a reflux condenser, a thermometer and a dropping funnel and the mixture was heated to 80° C. in an oil bath. Subsequently, 2-butylacrolein (7.44 g, 98 mass % article, 65.0 mmol) was added dropwise thereto through the dropping funnel for 1 hour. After completion of the dropwise addition, the mixture was heated and stirred at 100° C. for 2 hours. Then, the reaction mixture was poured into water and neutralized to pH 7 by ammonia water. The neutralized liquid was extracted with dichloromethane and then, dichloromethane was removed under reduced pressure. The resulting crude reaction product was purified by column chromatography (Hexane/AcOEt=100/0→1/1) using silica gel, followed by drying under reduced pressure to give 1.35 g of 8-bromo-3-butyl-5-fluoroquinoline as a brown solid (yield: 19.2%).

$^1$H-NMR (300 MHz, CDCl$_3$) δ: 8.93 (d, 1H), 8.21-8.17 (m, 1H), 7.94-7.87 (m, 1H), 7.14-7.07 (m, 1H), 2.86 (t, 2H), 1.77-1.67 (m, 2H), 1.44-1.35 (m, 2H), 0.96 (t, 3H)

[MS] EI (m/z): 281 (M$^+$), CI (m/z): 282 (MH$^+$)

(Second Step)

A 25 mL Schlenk tube was replaced with Ar, 8-bromo-3-butyl-5-fluoroquinoline (1.00 g, 3.54 mmol), tetrakis(triphenylphosphine)palladium (41.0 mg, 0.0354 mmol), 4.30 mL of piperidine and 2-methyl-3-butyn-2-ol (456 mg, 98 mass % article, 5.31 mmol) were added thereto and the mixture was stirred at 80° C. for 3 hours. A saturated aqueous ammonium chloride solution was added to the reaction mixture, and then the mixture was extracted with diethyl ether. The extract was dried over magnesium sulfate, followed by distilling off of the solvent under reduced pressure by an evaporator. The crude reaction product was purified by column chromatography (Hexane/AcOEt=100/0→1/5) using silica gel to give 778 mg of dimethylhydroxymethyl-5-fluoro-3-butyl-8-quinolylacetylene as a blackish brown liquid (yield: 77.9%).

$^1$H-NMR (300 MHz, CDCl$_3$) δ: 8.92 (d, 1H), 8.16-8.14 (m, 1H), 7.75-7.70 (m, 1H), 7.16-7.10 (m, 1H), 2.76 (t, 2H), 2.47 (brs, 1H), 1.72 (s, 6H), 1.67-1.58 (m, 2H), 1.42-1.22 (m, 2H), 0.92 (t, 3H)

[MS] EI (m/z): 285 (M$^+$), CI (m/z): 286 (MH$^+$)

(Third Step)

Dimethylhydroxymethyl-5-fluoro-3-butyl-8-quinolylacetylene (788 mg, 2.76 mmol) and NaOH (121 mg, KISHIDA CHEMICAL CO., Ltd., 0.7 mm granular, 98% article, 3.03 mmol) were placed in a 30 mL two-neck flask equipped with a reflux condenser and the air inside the flask was replaced with Ar. 18.0 mL of toluene was added thereto and the mixture was refluxed at 120° C. for 30 minutes. Diethyl ether was added to the reaction mixture, and then the mixture was washed with a saturated aqueous ammonium chloride solution and dried over magnesium sulfate, followed by distilling off of the solvent under reduced pressure by an evaporator. The crude reaction product was purified by column chromatography (Hexane/AcOEt=100/0→1/10) using silica gel to give 449 mg of 5-fluoro-3-butyl-8-quinolylethyne as a yellow solid. This was immediately dissolved in 11.0 mL of ethanol, under an argon atmosphere, in a 30 mL Schlenk tube, and Au(PPh$_3$)Cl (290 mg, 0.587 mmol) was added thereto, and then sodium ethoxide (243 µl, 0.620 mmol: 2.55 mol/L (liter) in ethanol solution) was added dropwise thereto, followed by stirring of the mixture at room temperature for 15 hours. After completion of the reaction, the resulting white precipitate was filtered and successively washed with 5 mL of water four times and 5 mL of ethanol twice, followed by drying under vacuum to give 751 mg of the desired compound as a pale yellow powder (yield: 39.7%).

$^1$H-NMR (300 MHz, CDCl$_3$) δ: 8.94 (d, 1H), 8.15-8.12 (m, 1H), 7.86-7.80 (m, 1H), 7.63-7.41 (m, 15H), 7.13-7.06 (m, 1H), 2.82 (t, 2H), 1.76-1.64 (m, 2H), 1.45-1.32 (m, 2H), 0.94 (t, 3H)

[MS] FAB (m/z): 686 (MH$^+$)

Elemental Analysis:

| | |
|---|---|
| Found | C: 57.00, H: 4.10, N: 1.99 |
| Theoretical | C: 57.12, H: 4.12, N: 2.04 |

Reference Example 34

Synthesis of 5-fluoro-3-methyl-8-quinolylethyne (First Step)

2-Bromo-5-fluoro-aniline (2.50 g, 95 mass % article, 12.5 mmol), m-nitrobenzenesulfonic acid (1.33 g, 6.53 mmol), 10.0 mL of 85 wt % aqueous phosphoric acid solution and ferrous sulfate heptahydrate (34.8 mg, 0.125 mmol) were placed in a 100 mL three-neck flask equipped with a magnetic stirrer, a reflux condenser, a thermometer and a dropping funnel and the mixture was heated to 80° C. in an oil bath. Subsequently, 2.32 g of methacrolein (98 mass % article, 32.5 mmol) was added dropwise thereto through the dropping funnel for 1 hour. After completion of the dropwise addition, the mixture was heated and stirred at 100° C. for 2 hours. Then, the reaction mixture was poured into water and neutralized to pH 7 by ammonia water. The neutralized liquid was extracted with dichloromethane and then, dichloromethane was removed under reduced pressure. The resulting crude reaction product was purified by column chromatography (Hexane/AcOEt=100/0→1/1) using silica gel, followed by drying under reduced pressure to give 730 mg of 8-bromo-5-fluoro-3-methyl-quinoline as a yellow white solid (yield: 24.3%).

$^1$H-NMR (300 MHz, CDCl$_3$) δ: 8.93 (d, 1H), 8.22-8.19 (m, 1H), 7.93-7.87 (m, 1H), 7.13-7.07 (m, 1H), 2.59 (s, 3H)

[MS] EI (m/z): 240 (M$^+$), CI (m/z): 241 (MH$^+$)

(Second Step)

A 25 mL Schlenk tube was replaced with Ar, 5-fluoro-3-methyl-8-quinolylethyne (600 mg, 2.50 mmol), tetrakis(triphenylphosphine)palladium (28.9 mg, 0.0250 mmol), 3.00 mL of piperidine and 2-methyl-3-butyn-2-ol (322 mg, 98 mass % article, 3.75 mmol) were added thereto and the mixture was stirred at 80° C. for 3 hours. The reaction mixture was cooled to room temperature, and then a saturated aqueous ammonium chloride solution was added thereto. The mixture was extracted with diethyl ether and the extract was dried over magnesium sulfate, followed by distilling off of the solvent under reduced pressure by an evaporator. The crude reaction product was purified by column chromatography (Hexane/AcOEt=100/0→1/5) using silica gel to give 336 mg of dimethylhydroxymethyl-5-fluoro-3-methyl-8-quinolylacetylene as a blackish brown liquid (yield: 55.2%).

$^1$H-NMR (300 MHz, CDCl$_3$) δ: 8.87 (d, 1H), 8.19-8.17 (m, 1H), 7.76-7.71 (m, 1H), 7.17-7.11 (m, 1H), 3.10 (brs, 3H), 2.54 (s, 3H), 1.71 (s, 6H)

[MS] EI (m/z): 243 (M$^+$), CI (m/z): 244 (MH$^+$)

(Third Step)

Dimethylhydroxymethyl-5-fluoro-3-methyl-8-quinolylacetylene (336 mg, 1.38 mmol) and NaOH (55.2 mg, KISHIDA CHEMICAL CO., Ltd., 0.7 mm granular, 98 mass %, 1.38 mmol) were placed in a 300 mL two-neck flask equipped with a reflux condenser and the air inside the flask was replaced with Ar. 3.0 mL of toluene was added thereto and the mixture was refluxed at 120° C. for 30 minutes. Diethyl ether was added to the reaction mixture and the mixture was washed with a saturated aqueous ammonium chloride solution and dried over magnesium sulfate, followed by distilling off of the solvent under reduced pressure by an evaporator. The crude reaction product was purified by column chromatography (Hexane/AcOEt=100/0→1/10) using silica gel to give 130 mg of the desired compound as a brownish brown solid (yield: 50.7%).

$^1$H-NMR (300 MHz, CDCl$_3$) δ: 8.94 (d, 1H), 8.22-8.19 (m, 1H), 7.86-7.82 (m, 1H), 7.19-7.13 (m, 1H), 3.54 (s, 1H), 2.54 (s, 3H)

[MS] EI (m/z): 185 (M$^+$), CI (m/z): 186 (MH$^+$)

Reference Example 35

Synthesis of (5-fluoro-3-methyl-8-quinolylethynyl)(triphenylphosphine)gold [Au(PPh$_3$) (5F3Me-8QE)]

Under an argon atmosphere, Au(PPh$_3$)Cl (178 mg, 0.360 mmol), 8-ethynyl-5-fluoro-3-methyl-quinoline (100 mg, 0.540 mmol) and 8.00 mL of ethanol were added to a 30 mL Schlenk tube, and then sodium ethoxide (149 µl, 0.380 mmol: 2.55 mol/L (liter) in ethanol solution) was added dropwise thereto and the mixture was stirred at room temperature for 15 hours. After completion of the reaction, the resulting white precipitate was filtered and successively washed with 5 mL of ethanol three times, 5 mL of water four times and 5 mL of ethanol three times, followed by drying under vacuum to give 140 mg of the desired compound as a pale yellow powder (yield: 60.5%).

$^1$H-NMR (300 MHz, CDCl$_3$) δ: 8.94 (d, 1H), 8.16-8.13 (m, 1H), 7.85-7.80 (m, 1H), 7.61-7.42 (m, 15H), 7.12-7.06 (m, 1H), 2.54 (s, 3H)

[MS] FAB (m/z): 644 (MH$^+$)

Elemental Analysis:

| | |
|---|---|
| Found | C: 55.97, H: 3.41, N: 2.16 |
| Theoretical | C: 56.00, H: 3.45, N: 2.18 |

Reference Example 36

Synthesis of 5-fluoro-2-methyl-8-quinolylethyne (First Step)

2-Bromo-5-fluoro-aniline (5.00 g, 95 mass % article, 25.0 mmol), m-nitrobenzenesulfonic acid (2.65 g, 13.0 mmol), 20.0 mL of 85 wt % aqueous phosphoric acid solution and ferrous sulfate heptahydrate (65.5 mg, 0.250 mmol) were placed in a 100 mL three-neck flask equipped with a magnetic stirrer, a reflux condenser, a thermometer and a dropping funnel and the mixture was heated to 80° C. in an oil bath. Subsequently, crotonaldehyde (4.64 g, 98 mass % article, 65.0 mmol) was added dropwise thereto through the dropping funnel for 1 hour. After completion of the dropwise addition, the mixture was heated and stirred at 100° C. for 2 hours. Then, the reaction mixture was poured into water and neutralized to pH 7 by ammonia water. The neutralized liquid was extracted with dichloromethane, and then dichloromethane was removed under reduced pressure. The resulting crude reaction product was purified by column chromatography (Hexane/AcOEt=100/0→1/1) using silica gel, followed by drying under reduced pressure to give 1.31 g of 8-bromo-5-fluoro-2-methyl-quinoline as a yellowish white solid (yield: 21.8%).

$^1$H-NMR (300 MHz, CDCl$_3$) δ: 8.31 (d, 1H), 7.96-7.91 (m, 1H), 7.40 (d, 1H), 7.08-7.02 (m, 1H), 2.83 (s, 3H)

[MS] EI (m/z): 240 (M$^+$), CI (m/z): 241 (MH$^+$)

(Second Step)

8-Bromo-5-fluoro-2-methyl-quinoline (600 mg, 2.50 mmol), tetrakis(triphenylphosphine)palladium (28.9 mg, 0.0250 mmol), 3.00 mL of piperidine and 2-methyl-3-butyn-2-ol (322 mg, 98 mass % article, 3.75 mmol) were added and the mixture was stirred at 80° C. for 3 hours. The reaction mixture was cooled to room temperature, and then a saturated aqueous ammonium chloride solution was added thereto and the mixture was extracted with diethyl ether. The extract was dried over magnesium sulfate, followed by distilling off of the solvent under reduced pressure by an evaporator. The crude reaction product was purified by column chromatography (Hexane/AcOEt=100/0→1/5) using silica gel to give 402 mg of dimethylhydroxymethyl-5-fluoro-2-methyl-8-quinolylacetylene as a brownish brown liquid (yield: 66.2%).

$^1$H-NMR (300 MHz, CDCl$_3$) δ: 8.29 (d, 1H), 7.78-7.73 (m, 1H), 7.36 (d, 1H), 7.12-7.06 (m, 1H), 2.80 (s, 3H), 2.19 (brs, 1H), 1.72 (s, 6H)

[MS] EI (m/z): 243 (M$^+$), CI (m/z): 244 (MH$^+$)

(Third Step)

8-Ethynyl-5-fluoro-2-methyl-quinoline (402 mg, 1.65 mmol) and NaOH (141 mg, KISHIDA CHEMICAL CO., Ltd., 0.7 mm granular, 98 mass %, 3.47 mmol) were placed in a 300 mL two-neck flask equipped with a reflux condenser and the air inside the flask was replaced with Ar. 5.0 mL of toluene was added thereto and the mixture was refluxed at 120° C. for 30 minutes. Diethyl ether was added to the reaction mixture and the mixture was washed with a saturated aqueous ammonium chloride solution and dried over magnesium sulfate, followed by distilling off of the solvent under reduced pressure by an evaporator. The crude reaction product was purified by column chromatography (Hexane/AcOEt=100/0→1/10) using silica gel to give 220 mg of the desired compound as a yellowish brown crystal (yield: 71.8%).

$^1$H-NMR (300 MHz, CDCl$_3$) δ: 8.32 (d, 1H), 7.90-7.60 (m, 1H), 7.40 (d, 1H), 7.15-7.09 (m, 1H), 3.51 (s, 1H), 2.80 (s, 3H)

[MS] EI (m/z): 185 (M$^+$), CI (m/z): 186 (MH$^+$)

Reference Example 37

Synthesis of (5-fluoro-2-methyl-8-quinolylethynyl)(triphenylphosphine)gold [Au(PPh$_3$) (5F2Me-8QE)]

Under an argon atmosphere, Au(PPh$_3$)Cl (356 mg, 0.720 mmol), 5-fluoro-2-methyl-quinolylethyne (200 mg, 1.08 mmol) and 16.0 mL of ethanol were added to a 30 mL Schlenk tube, and then sodium ethoxide (300 μl, 0.765 mmol: 2.55 mol/L (liter) in ethanol solution) was added dropwise thereto and the mixture was stirred at room temperature for 15 hours. After completion of the reaction, the resulting white precipitate was filtered and successively washed with 10 mL of ethanol three times, 10 mL of water four times and 10 mL of ethanol three times, followed by drying under vacuum to give 353 mg of the desired compound as a pale yellow powder (yield: 73.6%).

$^1$H-NMR (300 MHz, CDCl$_3$) δ: 8.27 (d, 1H), 7.89-7.84 (m, 1H), 7.89-7.45 (m, 15H), 7.32 (d, 1H), 7.08-7.02 (m, 1H), 2.84 (s, 3H)

[MS] FAB (m/z): 644 (MH$^+$)

Elemental Analysis:

| Found | C: 55.98, H: 3.42, N: 2.15 |
|---|---|
| Theoretical | C: 56.00, H: 3.45, N: 2.18 |

Reference Example 38

Synthesis of 5-fluoro-2-propyl-8-quinolylethyne (First Step)

2-Bromo-5-fluoro-aniline (5.00 g, 95 mass % article, 25.0 mmol), m-nitrobenzenesulfonic acid (2.65 g, 13.0 mmol), 20.0 mL of 85 wt % aqueous phosphoric acid solution and ferrous sulfate heptahydrate (65.5 mg, 0.250 mmol) were placed in a 100 mL three-neck flask equipped with a magnetic stirrer, a reflux condenser, a thermometer and a dropping funnel and the mixture was heated to 80° C. in an oil bath. Subsequently, trans-2-hexenal (6.51 g, 98 mass % article, 65.0 mmol) was added dropwise thereto through the dropping funnel for 1 hour. After completion of the dropwise addition, the mixture was heated and stirred at 100° C. for 2 hours. Then, the reaction mixture was poured into water and neutralized to pH 7 by ammonia water. The neutralized liquid was extracted with dichloromethane, and then dichloromethane was removed under reduced pressure. The resulting crude reaction product was purified by column chromatography (Hexane/AcOEt=100/0→1/10) using silica gel, followed by drying under reduced pressure to give 625 mg of 8-bromo-5-fluoro-2-propylquinoline as a yellowish white solid (yield: 9.33%).

$^1$H-NMR (300 MHz, CDCl$_3$) δ: 8.32 (d, 1H), 7.95-7.90 (m, 1H), 7.40 (d, 1H), 7.08-7.01 (m, 1H), 3.05-3.00 (m, 2H), 1.95-1.85 (m, 2H), 1.05 (t, 3H)

[MS] EI (m/z): 268 (M$^+$), CI (m/z): 269 (MH$^+$)

(Second Step)

A 25 mL Schlenk tube was replaced with Ar, 8-bromo-5-fluoro-2-propylquinoline (625 mg, 2.22 mmol), tetrakis(triphenylphosphine)palladium (25.6 mg, 0.0222 mmol), 2.70 mL of piperidine and 2-methyl-3-butyn-2-ol (285 mg, 98 mass % article, 3.32 mmol) were added and the mixture was stirred at 80° C. for 3 hours. The reaction mixture was cooled to room temperature, and then a saturated aqueous ammonium chloride solution was added thereto and the mixture was extracted with diethyl ether. The extract was dried over magnesium sulfate, followed by distilling off of the solvent under reduced pressure by an evaporator. The crude reaction product was purified by column chromatography (Hexane/AcOEt=100/0→1/5) using silica gel to give 326 mg of dimethylhydroxymethyl-5-fluoro-2-propyl-8-quinolylacetylene as a brownish brown liquid (yield: 54.2%).

¹H-NMR (300 MHz, CDCl₃) δ: 8.30 (d, 1H), 7.78-7.73 (m, 1H), 7.36 (d, 1H), 7.12-7.06 (m, 1H), 3.04-2.99 (m, 2H), 2.45 (brs, 1H), 2.01-1.88 (m, 2H), 1.72 (s, 6H), 1.06 (t, 3H)

[MS] EI (m/z): 271 (M⁺), CI (m/z): 272 (MH⁺)

(Third Step)

Dimethylhydroxymethyl-5-fluoro-2-propyl-8-quinolylacetylene (326 mg, 1.20 mmol) and NaOH (KISHIDA CHEMICAL CO., Ltd., 0.7 mm granular, 98 mass % article, 88.6 mg (2.22 mmol)) were placed in a 300 mL two-neck flask equipped with a reflux condenser and the air inside the flask was replaced with Ar. 3 mL of toluene was added thereto and the mixture was refluxed at 120° C. for 30 minutes. Diethyl ether was added to the reaction mixture and the mixture was washed with a saturated aqueous ammonium chloride solution and dried over magnesium sulfate, followed by distilling off of the solvent under reduced pressure by an evaporator. The crude reaction product was purified by column chromatography (Hexane/AcOEt=100/0→1/10) using silica gel to give 250 mg of the desired compound as a yellow solid (yield: 97.5%).

¹H-NMR (300 MHz, CDCl₃) δ: 8.32 (d, 1H), 7.89-7.84 (m, 1H), 7.40 (d, 1H), 7.14-7.08 (m, 1H), 3.49 (s, 1H), 3.06-3.01 (m, 2H), 1.97-1.60 (m, 2H), 0.86 (t, 3H)

[MS] EI (m/z): 213 (M⁺), CI (m/z): 214 (MH⁺)

Reference Example 39

Synthesis of (5-fluoro-2-propyl-8-quinolylethynyl)(triphenylphosphine)gold [Au(PPh₃) (5F2Pr-8QE)]

Under an argon atmosphere, Au(PPh₃)Cl (386 mg, 0.782 mmol), 5-fluoro-2-propyl-quinolylethyne (250 mg, 1.17 mmol) and 14.5 mL of ethanol were added to a 30 mL Schlenk tube, and then sodium ethoxide (321 μl, 0.819 mmol: 2.55 mol/L (liter) in ethanol solution) was added dropwise thereto and the mixture was stirred at room temperature for 15 hours. After completion of the reaction, the resulting white precipitate was filtered and successively washed with 10 mL of water four times and 10 mL of ethanol, followed by drying under vacuum to give 442 mg of the desired compound as a pale yellow powder (yield: 84.2%).

¹H-NMR (300 MHz, CDCl₃) δ: 8.28 (d, 1H), 7.89-7.84 (m, 1H), 7.71-7.41 (m, 15H), 7.34 (d, 1H) 7.07-7.02 (m, 1H), 3.10-3.05 (m, 2H), 1.96-1.84 (m, 2H) 1.05 (t, 3H)

[MS] FAB (m/z): 672 (MH⁺)

Elemental Analysis:

| Found | C: 57.01, H: 4.12, N: 2.01 |
| Theoretical | C: 57.07, H: 4.19, N: 2.08 |

Reference Example 40

Synthesis of 4-benzoylphenylethyne (First Step)

A 30 mL Schlenk tube was replaced with Ar, 3.9 g (15 mmol) of 4-bromobenzophenone, 173 mg (0.15 mmol) of tetrakis(triphenylphosphine)palladium, 15 mL of piperidine and 1.6 mL (16.5 mmol) of 2-methyl-3-butyn-2-ol were added and the mixture was stirred at 100° C. for 1 hour. A saturated aqueous ammonium chloride solution was added to the reaction mixture, and then the mixture was extracted with diethyl ether. The extract was dried over magnesium sulfate, followed by distilling off of the solvent under reduced pressure by an evaporator. The resulting crude reaction product was dissolved in 300 ml of hexane at 70° C., the insolubles were filtered off, and then the filtrate was cooled to give dimethylhydroxymethyl-4-benzoylphenylacetylene, i.e., the desired compound as a yellow crystal. Yield: 3.47 g (yield: 88%).

¹H-NMR (300 MHz, CDCl₃) δ: 7.72-7.80 (m, 4H), 7.46-7.63 (m, 5H), 2.09 (s, 1H), 1.64 (s, 6H)

[MS] EI (m/z): 264 (M⁺−1), CI (m/z): 265 (MH⁺)

(Second Step)

1.85 g (7 mmol) of dimethylhydroxymethyl-4-benzoylphenylacetylene and 294 mg (7.35 mmol) of NaOH (KISHIDA CHEMICAL CO., Ltd., 0.7 mm granular, 98%) were placed in a 50 mL two-neck flask equipped with a reflux condenser and the air inside the flask was replaced with Ar. 35 mL of toluene was added thereto and the mixture was refluxed at 120° C. for 0.5 hour. Toluene was added to the reaction mixture and the mixture was washed with a saturated aqueous ammonium chloride solution and dried over magnesium sulfate, followed by distilling off of the solvent under reduced pressure by an evaporator. The crude reaction product was purified by column chromatography (Hexane/AcOEt=10/1) using silica gel to give 4-benzoylphenylethyne as a pale brown solid (1.1 g, yield: 76%).

¹H-NMR (300 MHz, CDCl₃) δ: 7.46-7.81 (m, 9H), 3.20 (s, 1H)

[MS] EI (m/z): 206 (M⁺−1), CI (m/z): 207 (MH⁺)

Reference Example 41

Synthesis of (4-benzoylphenylethynyl)(triphenylphosphine)gold [Au(PPh₃) (4Bz-PE)]

Under an argon atmosphere, Au(PPh₃)Cl (445 mg, 0.90 mmol), 4-benzoylphenylethyne (278 mg, 1.35 mmol) and ethanol (18 ml) were added to a 30 mL Schlenk tube, and then sodium ethoxide (371 μl, 0.945 mmol: 2.55 mol/L (liter) in ethanol solution) was added dropwise thereto and the mixture was stirred at room temperature for 23 hours. After completion of the reaction, the resulting white precipitate was filtered and successively washed with ethanol (12 ml×three times), water (12 ml×three times) and ethanol (6 ml×three times), followed by drying under vacuum to give 0.56 g of the desired compound as a yellow powder (yield: 94%).

¹H-NMR (400 MHz, CDCl₃) δ: 7.71-7.80 (m, 4H), 7.43-7.61 (m, 20H)

(FAB-MS) (M/Z): 665 (M+H)⁺

Luminescence analysis: (CHCl₃, 77K, Ex250 nm) λ (nm): 468, 502

Elemental Analysis:

| Found | C: 59.63, H: 3.44 |
| Theoretical | C: 59.65, H: 3.64 |

Reference Example 42

Synthesis of Pyrazylethyne (First Step)

A 30 mL Schlenk tube was replaced with Ar, 1.54 mL (17.5 mmol) of chloropyrazine, 404 mg (0.35 mmol) of tetrakis(triphenylphosphine)palladium, 17.5 mL of 1-methylpiperidine and 3.4 mL (5.5 mmol) of 2-methyl-3-butyn-2-ol were added thereto and the mixture was stirred at 100° C. for 1.5 hours.

A saturated aqueous ammonium chloride solution was added to the reaction mixture, and then the mixture was extracted with diethyl ether. The extract was dried over magnesium sulfate, followed by distilling off of the solvent under reduced pressure by an evaporator. The crude reaction product was purified by column chromatography (Hexane/AcOEt=5/1-4/1) using silica gel to give dimethylhydroxymethylpyrazylacetylene, i.e., the desired compound as a pale yellow liquid. Yield: 1.94 g (yield: 68%).

$^1$H-NMR (300 MHz, CDCl$_3$) δ: 8.66 (s, 1H), 8.54 (d, 1H), 8.49 (d, 1H), 2.98 (s, 1H), 1.66 (s, 6H)

[MS] EI (m/z): 162 (M$^+$), CI (m/z): 163 (MH$^+$)

(Second Step)

1.94 g (11.96 mmol) of pyrazylacetylene and 502 mg (12.56 mmol) of NaOH (KISHIDA CHEMICAL CO., Ltd., 0.7 mm granular, 98%) were placed in a 100 mL two-neck flask equipped with a reflux condenser and the air inside the flask was replaced with Ar. 60 mL of toluene was added thereto and the mixture was refluxed at 120° C. for 0.33 hour. Toluene was added to the reaction mixture and the mixture was washed with a saturated aqueous ammonium chloride solution and dried over magnesium sulfate, followed by distilling off of the solvent under reduced pressure. Then, 20 mL of hexane was added to the crude reaction product and the mixture was cooled to give pyrazylethyne, i.e., the desired compound as a yellow solid. (0.63 g, yield: 50%).

$^1$H-NMR (300 MHz, CDCl$_3$) δ: 8.71 (s, 1H), 8.56 (d, 1H), 8.52 (d, 1H), 3.35 (s, 1H)

[MS] EI (m/z): 104 (M$^+$), CI (m/z): 105 (MH$^+$)

Reference Example 43

Synthesis of (pyrazylethynyl)(triphenylphosphine)gold [Au(PPh$_3$)(PzE)]

Under an argon atmosphere, Au(PPh$_3$)Cl (297 mg, 0.6 mmol), pyrazylethyne (94 mg, 0.9 mmol) and ethanol (12 ml) were added to a 20 mL Schlenk tube, and then sodium ethoxide (247 μl, 0.63 mmol: 2.55 mol/L (liter) in ethanol solution) was added dropwise thereto and the mixture was stirred at room temperature for 17 hours. After completion of the reaction, the resulting white precipitate was filtered and successively washed with ethanol (8 ml×three times), water (8 ml×three times) and ethanol (6 ml×twice), followed by drying under vacuum to give 0.27 g of the desired compound as a white powder (yield: 81%).

$^1$H-NMR (400 MHz, CDCl$_3$) δ: 8.65 (d, 1H), 8.47 (dd, 1H), 8.33 (d, 1H), 7.57-7.45 (m, 15H)

(FAB-MS) (M/Z): 563 (MH$^+$)

Luminescence analysis: (CHCl$_3$, 77K, Ex250 nm) λ (nm): 449, 471

Elemental Analysis:

| Found | C: 51.18, H: 2.93, N: 4.97 |
|---|---|
| Theoretical | C: 51.26, H: 3.23, N: 4.98 |

Reference Example 44

Synthesis of 4-acetylphenylethyne (First Step)

A 30 mL Schlenk tube was replaced with Ar, 1.59 g (8 mmol) of p-bromoacetophenone, 92.4 mg (0.08 mmol) of tetrakis(triphenylphosphine)palladium, 8 mL of piperidine and 853 μL (8.8 mmol) of 2-methyl-3-butyn-2-ol were added and the mixture was stirred at 100° C. for 1 hour. A saturated aqueous ammonium chloride solution was added to the reaction mixture, and then the mixture was extracted with diethyl ether. The extract was dried over magnesium sulfate, followed by distilling off of the solvent under reduced pressure by an evaporator. The resulting crude reaction product was purified by column chromatography (Hexane/AcOEt=5/1) using silica gel to give dimethylhydroxymethyl-4-acetylphenylacetylene, i.e., the desired compound as a viscous yellow liquid. Yield: 1.5 g (yield: 93%).

$^1$H-NMR (300 MHz, CDCl$_3$) δ: 7.86-7.92 (m, 2H), 7.46-7.50 (m, 2H), 2.59 (s, 3H), 2.24 (s, 1H), 1.63 (s, 6H)

[MS] EI (m/z): 202 (M$^+$−1), CI (m/z): 203 (MH$^+$)

(Second Step)

1.45 g (7.17 mmol) of dimethylhydroxymethyl-4-acetylphenylacetylene and 301 mg (7.53 mmol) of NaOH (KISHIDA CHEMICAL CO., Ltd., 0.7 mm granular, 98%) were placed in a 100 mL two-neck flask equipped with a reflux condenser and the air inside the flask was replaced with Ar. 36 mL of toluene was added thereto and the mixture was refluxed at 120° C. for 15 minutes. Toluene was added to the reaction mixture and the mixture was washed with a saturated aqueous ammonium chloride solution and dried over magnesium sulfate, followed by distilling off of the solvent under reduced pressure by an evaporator. Then, 25 mL of hexane was added to the resulting crude reaction product and the mixture was cooled to give 4-acetylphenylethyne as a yellow solid. (0.74 g, yield: 56%).

$^1$H-NMR (300 MHz, CDCl$_3$) δ: 7.88-7.94 (m, 2H), 7.53-7.59 (m, 2H), 3.25 (s, 1H), 2.60 (s, 3H)

[MS] EI (m/z): 144 (M$^+$−1), CI (m/z): 145 (MH$^+$)

Reference Example 45

Synthesis of (4-acetylphenylethynyl)(triphenylphosphine)gold [Au(PPh$_3$) (4Ac-PE)]

Under an argon atmosphere, Au(PPh$_3$)Cl (297 mg, 0.60 mmol), 4-acetylphenylethyne (130 mg, 0.9 mmol) and ethanol (12 ml) were added to a 30 mL Schlenk tube, and then sodium ethoxide (247 μl, 0.63 mmol: 2.55 mol/L (liter) in ethanol solution) was added dropwise thereto and the mixture was stirred at room temperature for 17 hours. After completion of the reaction, the resulting white precipitate was filtered and successively washed with ethanol (12 ml×three times), water (12 ml×three times) and ethanol (6 ml×three times), followed by drying under vacuum to give 0.32 g of the desired compound as a white powder (yield: 89%).

$^1$H-NMR (300 MHz, CDCl$_3$) δ: 7.84-7.88 (m, 2H), 7.43-7.61 (m, 17H), 2.57 (s, 3H)

FAB-MS (M/Z): 603 (M+H)$^+$

Luminescence analysis: (CHCl$_3$, 77K, Ex250 nm) λ (nm): 465, 499

Elemental Analysis:

| Found | C: 55.86, H: 3.67 |
|---|---|
| Theoretical | C: 55.83, H: 3.68 |

Industrial Applicability

The present invention provides a substituted ethynyl gold-nitrogen containing heterocyclic carbene complex useful as a light emitting material for an electric field light-emitting element (organic electroluminescence device) and an organic electro-luminescence device emitting blue to green light using it.

The invention claimed is:

1. A substituted ethynyl gold-nitrogen containing heterocyclic carbene complex represented by the general formula (1):

(1)

wherein:

L represents a nitrogen containing heterocyclic carbene ligand represented by the following formula:

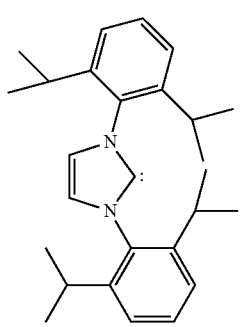

(4)

IPr

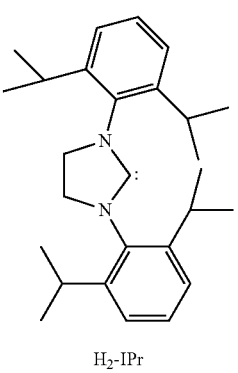

(5)

IMes

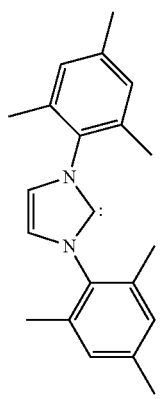

(6)

IAd

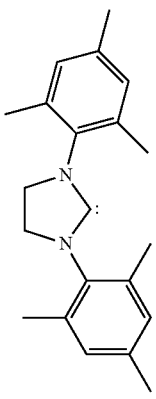

(7)

ItBu

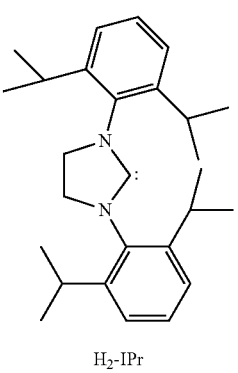

(8)

H₂-IPr

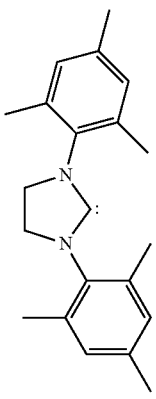

(9)

H₂-IMes

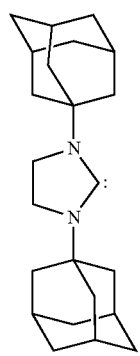

(10)

H₂-IAd

-continued

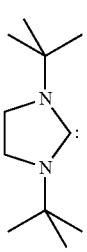

H₂-ItBu

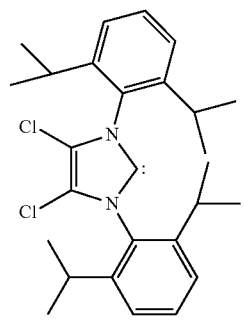

Cl₂-IPr or

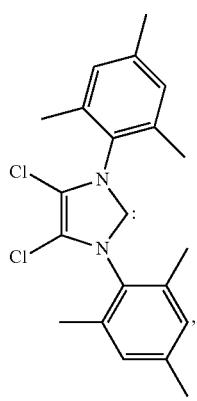

Cl₂-IMes

, and

X represents an alkyl group, a cycloalkyl group, an aryl group, an aralkyl group or a heterocyclic group; in which one or more hydrogen atoms on the carbon atom(s) of X may be replaced by a halogen atom, an alkyl group, a cycloalkyl group, an alkenyl group, an aryl group, an aralkyl group, an alkoxy group, an aryloxy group, a dialkylamino group, an acyl group or an arylcarbonyl group; and, when more than one hydrogen atom on the carbon atom(s) of X is replaced by the alkyl group, the alkenyl group, the aryl group, the aralkyl group, the alkoxy group, the aryloxy group, the dialkylamino group, the acyl group or the arylcarbonyl group, the adjacent groups may be bonded together to form a ring.

2. The substituted ethynyl gold-nitrogen containing heterocyclic carbene complex according to claim 1, wherein X is a group selected from the group consisting of an alkyl group having 1 to 12 carbon atoms, a cycloalkyl group having 3 to 12 carbon atoms, an aryl group having 6 to 18 carbon atoms, an aralkyl group having 7 to 20 carbon atoms and a heterocyclic group having 4 to 16 carbon atoms; in which one or more hydrogen atoms on the carbon atom(s) of X may be replaced by a fluorine atom, a chlorine atom, a bromine atom, an iodine atom, an alkyl group having 1 to 20 carbon atoms, a cycloalkyl group having 3 to 7 carbon atoms, an alkenyl group having 2 to 12 carbon atoms, an aryl group having 6 to 16 carbon atoms, an aralkyl group having 7 to 20 carbon atoms, an alkoxy group having 1 to 10 carbon atoms, an aryloxy group having 6 to 14 carbon atoms, a dialkylamino group having 2 to 10 carbon atoms, an acyl group having 2 to 10 carbon atoms or an arylcarbonyl group having 7 to 11 carbon atoms.

3. The substituted ethynyl gold-nitrogen containing heterocyclic carbene complex according to claim 1, wherein X is a group selected from the group consisting of a quinolyl group, a phenyl group, a fluorophenyl group, a difluorophenyl group, a methoxyphenyl group, a fluoroquinolyl group, a chloroquinolyl group, a pyridyl group, a fluoropyridyl group, a biphenyl group, a nitrophenyl group, a naphthyl group, a fluoronaphthyl group, an anthryl group, a phenanthryl group, a pyrenyl group, a fluorenyl group, a propyl-fluoroquinolyl group, a butyl-fluoroquinolyl group, a methyl-fluoroquinolyl group, a benzoylphenyl group, an acetylphenyl group, and a pyrazyl group.

4. An organic electroluminescent device comprising a light emitting layer or a plurality of organic compound thin layers comprising a light emitting layer formed between a pair of electrodes, wherein at least one organic compound thin layer contains the substituted ethynyl gold-nitrogen containing heterocyclic carbene complex according to claim 1.

5. A method for preparing the substituted ethynyl gold-nitrogen containing heterocyclic carbene complex according to claim 1, the method comprising reacting a substituted ethynyl gold phosphine complex with a nitrogen containing heterocyclic carbene ligand.

6. The method according to claim 5, wherein the nitrogen-containing heterocyclic carbene ligand is obtained by reacting a nitrogen containing heterocyclic hydrohalide with a base.

7. The method according to claim 5, wherein, in the reaction, the nitrogen containing heterocyclic carbene ligand is used in an amount of 1 to 3 mol, relative to 1 mol of the substituted ethynyl gold phosphine complex.

8. The method according to claim 5 or 7, wherein the reaction is conducted by mixing together the substituted ethynyl gold phosphine complex and the nitrogen containing heterocyclic carbene ligand and stirring the resulting mixture in the presence of a solvent at a temperature of 0 to 120° C.

9. The organic electroluminescent device according to claim 4, wherein the device comprises a glass with indium tin oxide as a transparent electrode substrate, a hole transport layer vacuum-vapor-deposited thereon, a light emitting layer vacuum-vapor-deposited thereon, a hole block layer vacuum-vapor-deposited thereon, an electron transport layer vacuum-vapor-deposited thereon and an aluminum electrode vacuum-vapor-deposited thereon.

10. The substituted ethynyl gold-nitrogen containing heterocyclic carbene complex according to claim 1, wherein the substituted ethynyl gold-nitrogen containing heterocyclic carbene complex is at least one selected from the group consisting of:

(15)
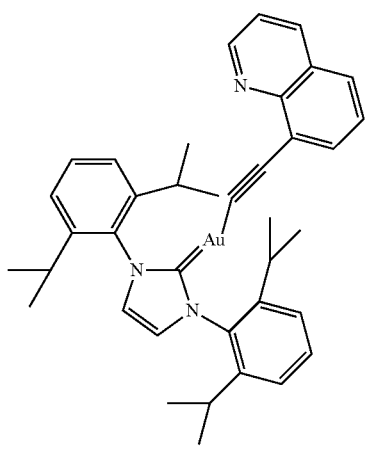
Au(IPr)(8QE)
(16)
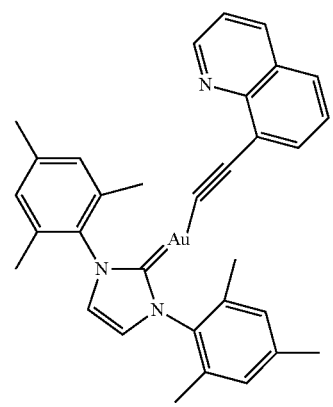
Au(IMes)(8QE)
(17)
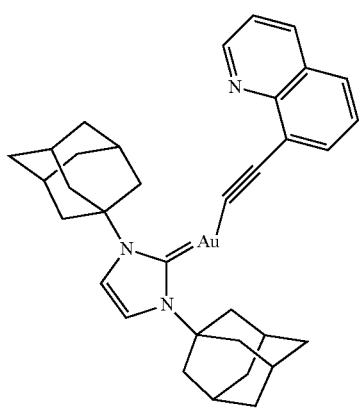
Au(IAd)(8QE)
-continued
(18)
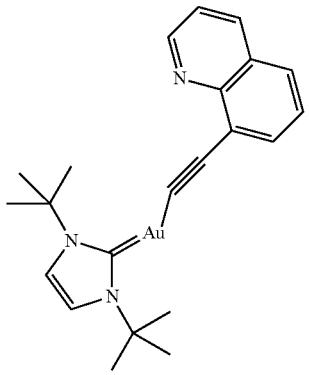
Au(ItBu)(8QE)
(19)
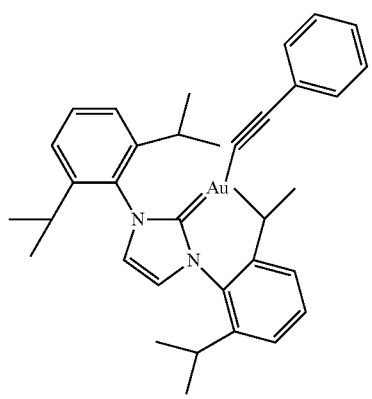
Au(IPr)(PE)
(20)
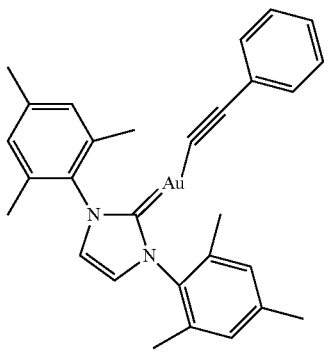
Au(IMes)(PE)

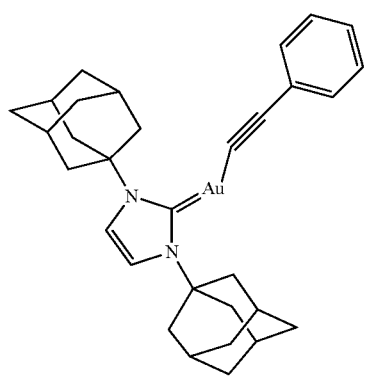
Au(IAd)(PE)
(21)
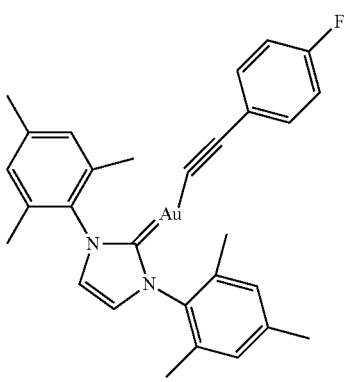
Au(IMes)(4F-PE)
(24)
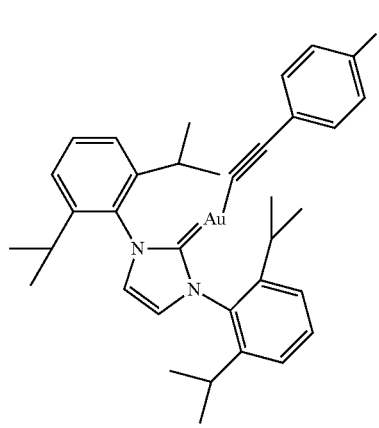
Au(ItBu)(PE)
(22)
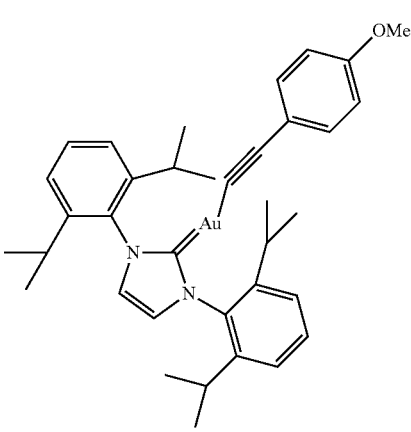
Au(IPr)(4MeO-PE)
(25)
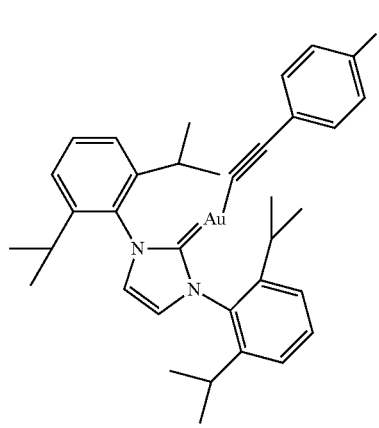
Au(IPr)(4F-PE)
(23)
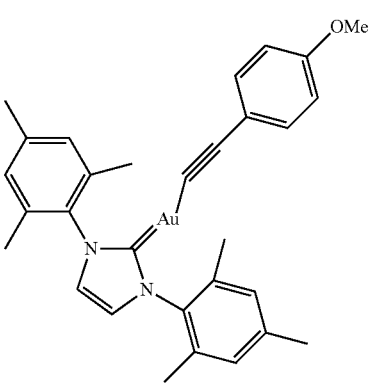
Au(IMes)(4MeO-PE)
(26)

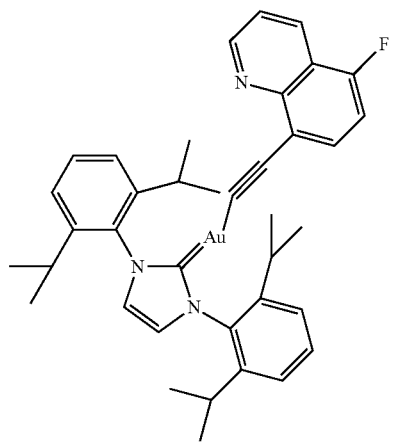
Au(IPr)(5F-8QE)
(27)
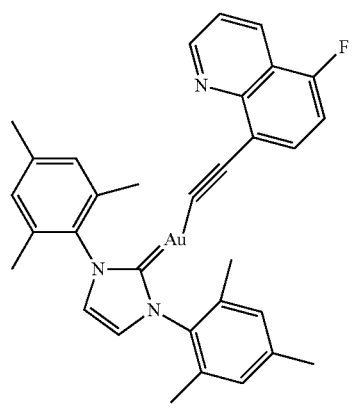
Au(IMes)(5F-8QE)
(28)
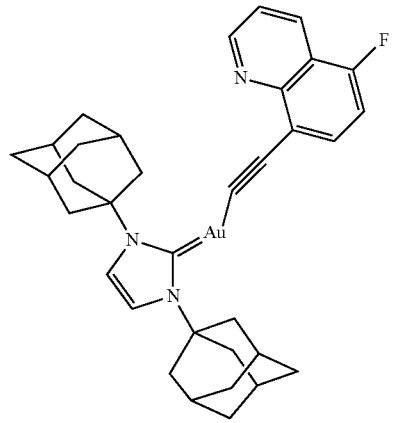
Au(IAd)(5F-8QE)
(29)
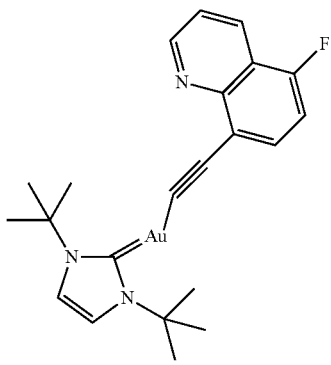
Au(ItBu)(5F-8QE)
(30)
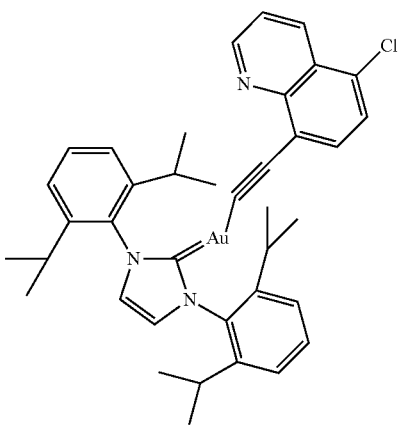
Au(IPr)(5Cl-8QE)
(31)
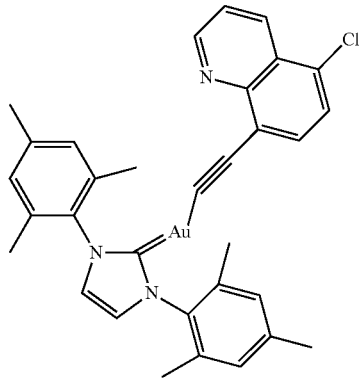
Au(IMes)(5Cl-8QE)
(32)

-continued
(33)
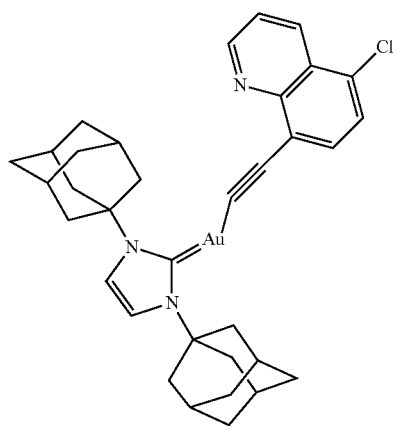
Au(IAd)(5Cl-8QE)
(34)
Au(ItBu)(5Cl-8QE)
(35)
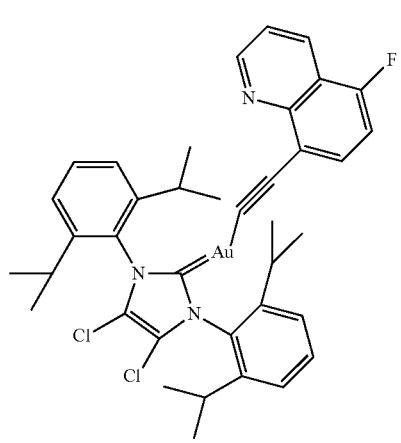
Au(Cl₂-IPr)(5F-8QE)
-continued
(36)
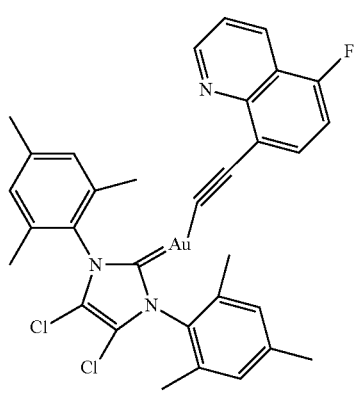
Au(Cl₂-IMes)(5F-8QE)
(37)
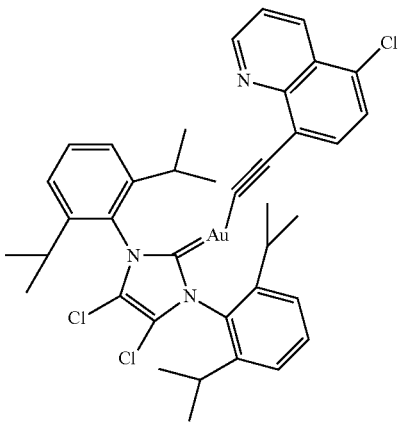
Au(Cl₂-IPr)(5Cl-8QE)
(38)
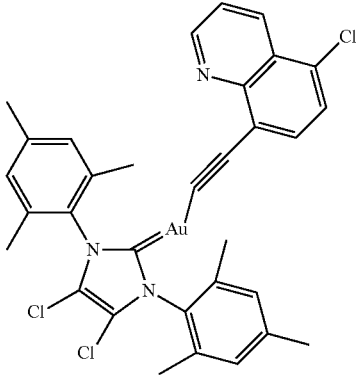
Au(Cl₂-IMes)(5Cl-8QE)

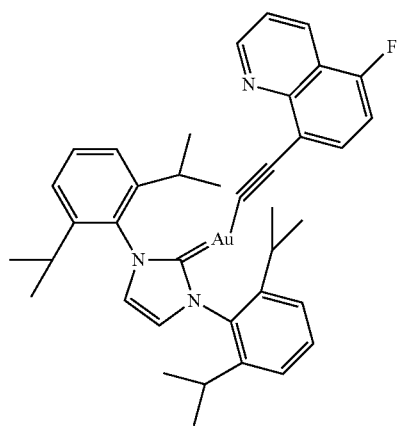
Au(H₂-IPr)(5F-8QE)  (39)
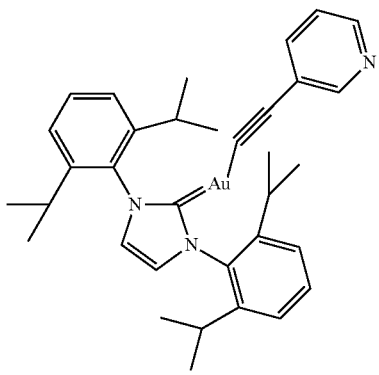
Au(IPr)(3PyE)  (42)
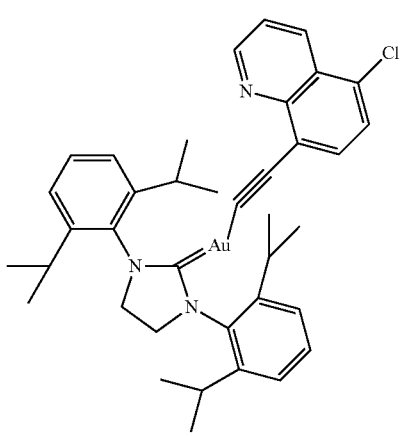
Au(H₂-IPr)(5Cl-8QE)  (40)
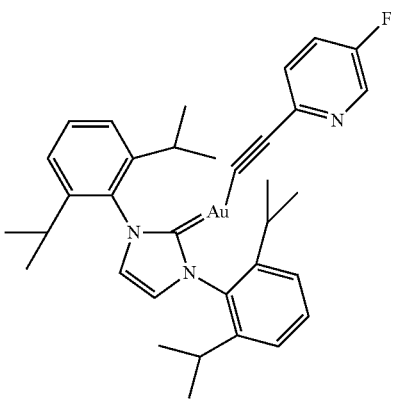
Au(IPr)(5F-2PyE)  (43)
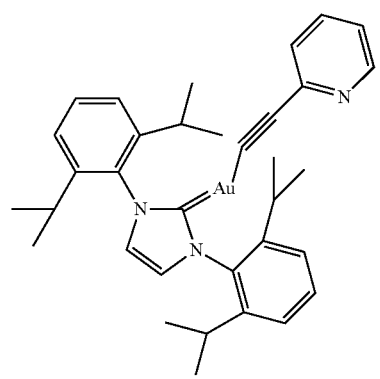
Au(IPr)(2PyE)  (41)
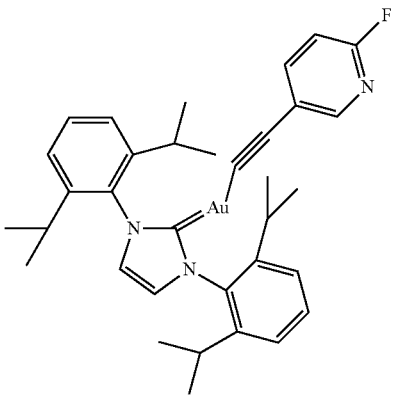
Au(IPr)(6F-3PyE)  (44)

-continued
(45)
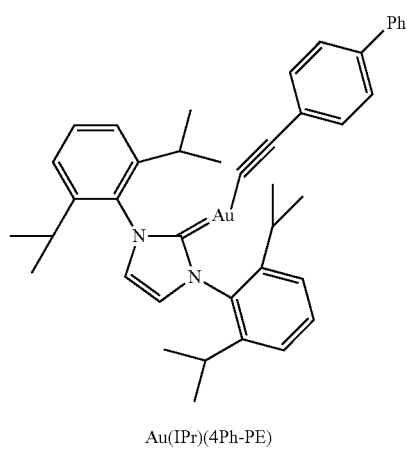
Au(IPr)(4Ph-PE)
(46)
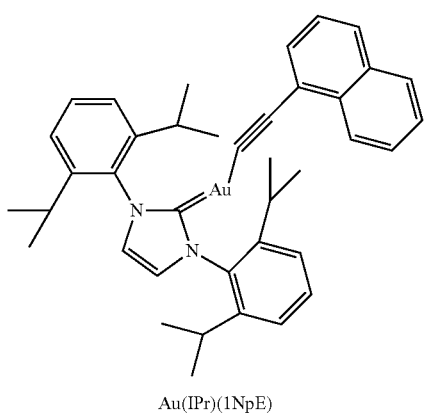
Au(IPr)(4NO₂-PE)
(47)
Au(IPr)(2,4-F₂-PE)
-continued
(48)
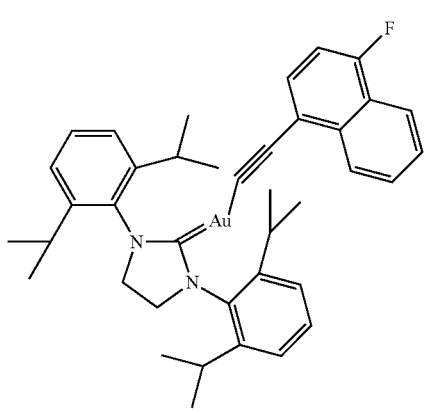
Au(IPr)(1NpE)
(49)
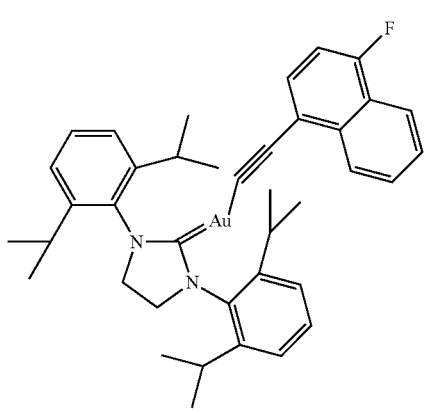
Au(H₂-IPr)(4F-1NpE)
(50)
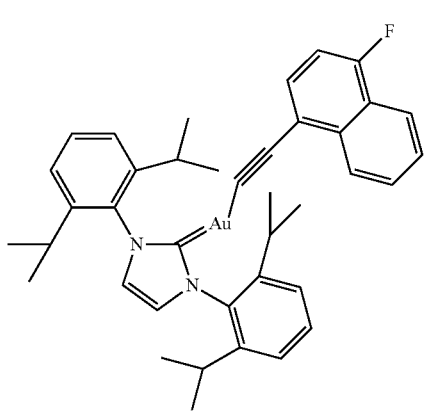
Au(IPr)(4F-1NpE)

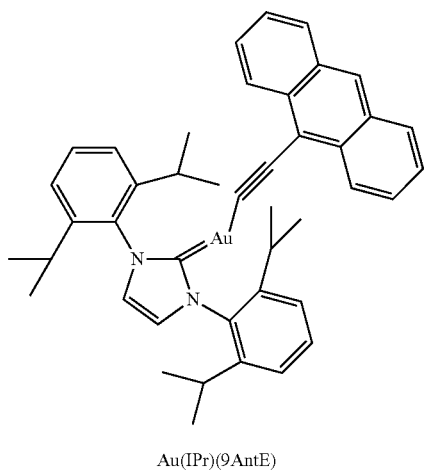
(51)
Au(IPr)(9AntE)
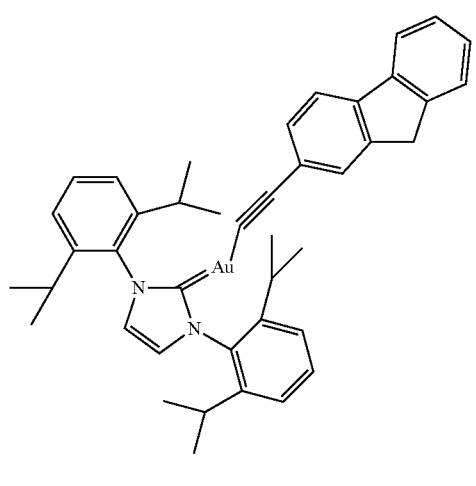
(54)
Au(IPr)(2FluorE)
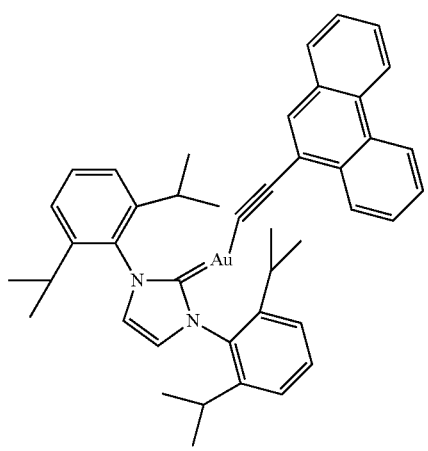
(52)
Au(IPr)(9PhenE)
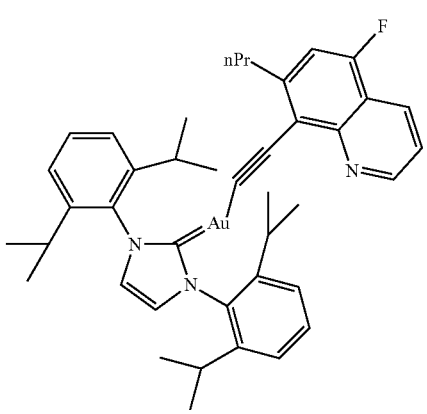
(55)
Au(IPr)(5F7Pr-8QE)
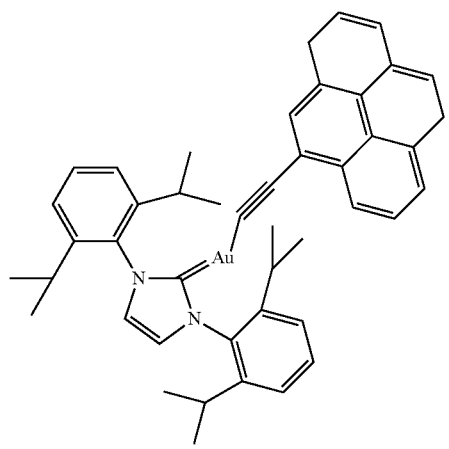
(53)
Au(IPr)(1PyrenE)
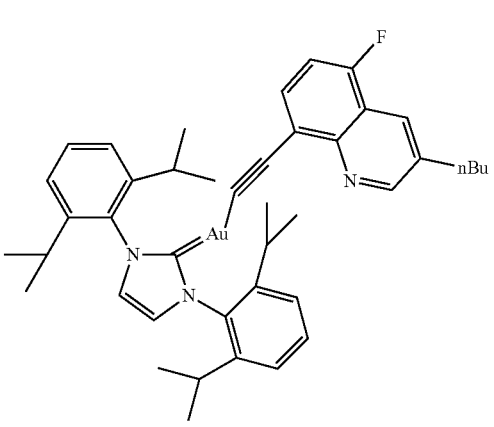
(56)
Au(IPr)(5F3Bu-8QE)

-continued
(57)
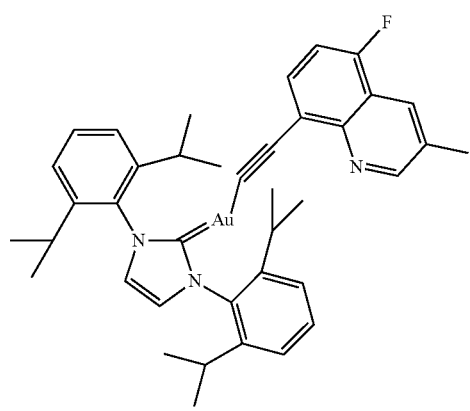
Au(IPr)(5F3Me-8QE)
(58)
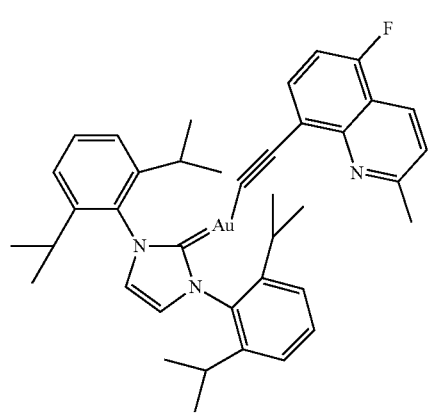
Au(IPr)(5F2Me-8QE)
(59)
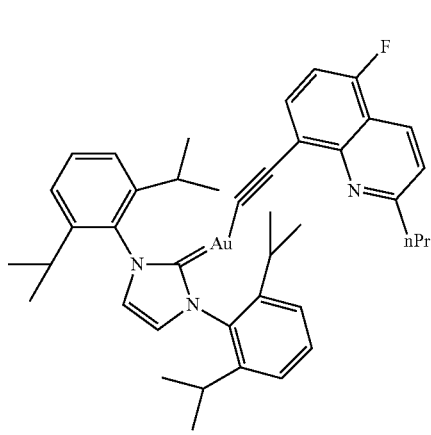
Au(IPr)(5F2Pr-8QE)
-continued
(60)
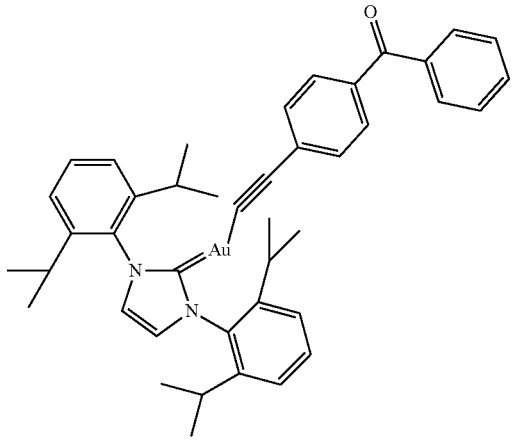
Au(IPr)(4Bz-PE)
(61)
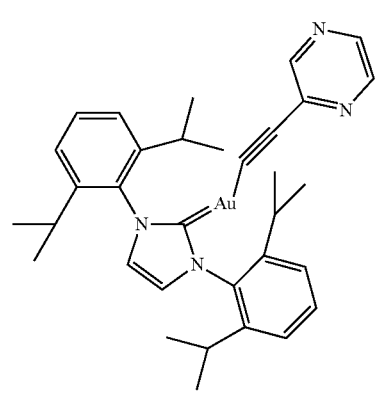
Au(IPr)(2PzE)
and
(62)
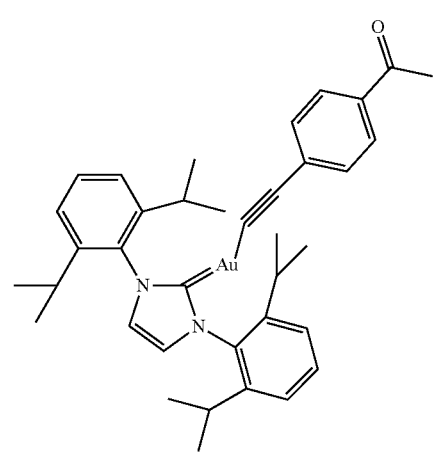
Au(IPr)(4Ac-PE)
* * * * *